US011137369B2

(12) United States Patent
Rothberg et al.

(10) Patent No.: US 11,137,369 B2
(45) Date of Patent: Oct. 5, 2021

(54) INTEGRATED SENSOR ARRAYS FOR BIOLOGICAL AND CHEMICAL ANALYSIS

(71) Applicant: Life Technologies Corporation, Carlsbad, CA (US)

(72) Inventors: Jonathan M. Rothberg, Guilford, CT (US); Mark James Milgrew, Branford, CT (US); Jonathan Schultz, Guilford, CT (US); David Marran, Durham, CT (US); Todd Rearick, Cheshire, CT (US); Kim L. Johnson, Carlsbad, CA (US); James Bustillo, Castro Valley, CA (US)

(73) Assignee: Life Technologies Corporation, Carlsbad, CA (US)

( * ) Notice: Subject to any disclaimer, the term of this patent is extended or adjusted under 35 U.S.C. 154(b) by 27 days.

(21) Appl. No.: 15/971,857

(22) Filed: May 4, 2018

(65) Prior Publication Data

US 2019/0011396 A1 Jan. 10, 2019

Related U.S. Application Data

(63) Continuation of application No. 14/862,930, filed on Sep. 23, 2015, now Pat. No. 9,964,515, which is a (Continued)

(51) Int. Cl.
*G01N 27/414* (2006.01)
*C12Q 1/6874* (2018.01)
(Continued)

(52) U.S. Cl.
CPC ....... *G01N 27/4145* (2013.01); *C12Q 1/6869* (2013.01); *C12Q 1/6874* (2013.01); *G01N 27/4148* (2013.01); *H01L 21/82* (2013.01)

(58) Field of Classification Search
CPC .................................................. G01N 27/4145
(Continued)

(56) References Cited

U.S. PATENT DOCUMENTS 3,531,258 A 9/1970 Merrifield et al.
4,008,736 A 2/1977 Wittmann-Liebold et al.
(Continued)

FOREIGN PATENT DOCUMENTS

CN 1582334 2/2005
CN 101676714 3/2010
(Continued)

OTHER PUBLICATIONS

Ahmadian et al., "Single-nucleotide polymorphism analysis by pyrosequencing", Analytical and Biochemistry, vol. 280, 2000, pp. 103-110.
(Continued)

*Primary Examiner* — Matthew E. Gordon

(57) ABSTRACT

An apparatus comprising a chemical field effect transistor array in a circuit-supporting substrate is disclosed. The transistor array has disposed on its surface an array of sample-retaining regions capable of retaining a chemical or biological sample from a sample fluid. The transistor array has a pitch of 10 μm or less and a sample-retaining region is positioned on at least one chemical field effect transistor which is configured to generate at least one output signal related to a characteristic of a chemical or biological sample in such sample-retaining region.

7 Claims, 13 Drawing Sheets

Related U.S. Application Data continuation of application No. 14/599,948, filed on Jan. 19, 2015, now abandoned, which is a continuation of application No. 13/125,133, filed as application No. PCT/US2009/005745 on Oct. 22, 2009, now Pat. No. 8,936,763, which is a continuation of application No. 12/474,897, filed on May 29, 2009, now abandoned, and a continuation of application No. 12/475,311, filed on May 29, 2009, now abandoned.

(60) Provisional application No. 61/205,626, filed on Jan. 22, 2009, provisional application No. 61/198,222, filed on Nov. 4, 2008, provisional application No. 61/196,953, filed on Oct. 22, 2008.

(51) Int. Cl.
*H01L 21/82* (2006.01)
*C12Q 1/6869* (2018.01)

(58) Field of Classification Search
USPC ............... 257/253, E23.08; 438/10; 422/407
See application file for complete search history.

(56) References Cited

U.S. PATENT DOCUMENTS 4,086,642 A 4/1978 Yoshida et al.
4,411,741 A 10/1983 Janata
4,437,969 A 3/1984 Covington et al.
4,438,354 A 3/1984 Haque et al.
4,444,644 A 4/1984 Hiramoto et al.
4,490,678 A 12/1984 Kuisl et al.
4,558,845 A 12/1985 Hunkapiller
4,641,084 A 2/1987 Komatsu
4,660,063 A 4/1987 Anthony
4,691,167 A 9/1987 Dvlekkert et al.
4,701,253 A 10/1987 Ligtenberg et al.
4,722,830 A 2/1988 Urie et al.
4,743,954 A 5/1988 Brown
4,764,797 A 8/1988 Shaw et al.
4,777,019 A 10/1988 Dandekar
4,822,566 A 4/1989 Newman
4,863,849 A 9/1989 Melamede
4,864,229 A 9/1989 Lauks et al.
4,874,499 A 10/1989 Smith et al.
4,893,088 A 1/1990 Myers et al.
4,927,736 A 5/1990 Mueller et al.
4,971,903 A 11/1990 Hyman
5,009,766 A 4/1991 Lauks
5,038,192 A 8/1991 Bonneau et al.
5,082,788 A 1/1992 Farnsworth et al.
5,110,441 A 5/1992 Kinlen et al.
5,113,870 A 5/1992 Rossenfeld
5,118,607 A 6/1992 Bignami et al.
5,126,022 A 6/1992 Soane et al.
5,126,759 A 6/1992 Small et al.
5,132,418 A 7/1992 Caruthers et al.
5,138,251 A 8/1992 Koshiishi et al.
5,140,393 A 8/1992 Hijikihigawa et al.
5,142,236 A 8/1992 Maloberti et al.
5,151,587 A 9/1992 MacHida et al.
5,151,759 A 9/1992 Vinal
5,164,319 A 11/1992 Hafeman et al.
5,202,576 A 4/1993 Liu et al.
5,284,566 A 2/1994 Cuomo et al.
5,313,984 A 5/1994 Garwood, Jr. et al.
5,317,407 A 5/1994 Michon
5,319,226 A 6/1994 Sohn et al.
5,407,854 A 4/1995 Baxter et al.
5,436,149 A 7/1995 Barnes
5,439,839 A 8/1995 Jang
5,466,348 A 11/1995 Holm-Kennedy
5,475,337 A 12/1995 Tatsumi
5,490,971 A 2/1996 Gifford et al.
5,498,392 A 3/1996 Wilding et al.
5,520,787 A 5/1996 Hanagan et al.
5,554,339 A 9/1996 Cozzette et al.
5,583,462 A 12/1996 Grasshoff
5,587,128 A 12/1996 Wilding et al.
5,587,894 A 12/1996 Naruo
5,593,838 A 1/1997 Zanzucchi et al.
5,600,451 A 2/1997 Maki
5,627,403 A 5/1997 Bacchetta et al.
5,631,704 A 5/1997 Dickinson et al.
5,637,469 A 6/1997 Wilding et al.
5,646,558 A 7/1997 Jamshidi
5,650,649 A 7/1997 Tsukiji
5,702,964 A 12/1997 Lee
5,793,230 A 8/1998 Chu et al.
5,830,645 A 11/1998 Pinkel et al.
5,846,708 A 12/1998 Hollis et al.
5,894,284 A 4/1999 Garrity et al.
5,895,274 A 4/1999 Lane et al.
5,907,765 A 5/1999 Lescouzeres et al.
5,911,873 A 6/1999 Mccarron et al.
5,912,560 A 6/1999 Pasternak
5,922,591 A 7/1999 Anderson et al.
5,923,421 A 7/1999 Rajic et al.
5,944,970 A 8/1999 Rosenblatt
5,958,703 A 9/1999 Dower et al.
5,965,452 A 10/1999 Kovacs
6,001,299 A 12/1999 Kawabe et al.
6,002,299 A 12/1999 Thomsen
6,010,607 A 1/2000 Ramsey
6,021,172 A 2/2000 Fossum et al.
6,033,546 A 3/2000 Ramsey
6,054,034 A 4/2000 Soane et al.
6,107,032 A 8/2000 Kilger et al.
6,191,444 B1 2/2001 Clampitt et al.
6,195,585 B1 2/2001 Karunasiri et al.
6,210,891 B1 4/2001 Nyren et al.
6,255,678 B1 7/2001 Sawada et al.
6,262,568 B1 7/2001 Komatsu et al.
6,274,320 B1 8/2001 Rothberg et al.
6,275,061 B1 8/2001 Tomita
6,280,586 B1 8/2001 Wolf et al.
6,294,133 B1 9/2001 Sawada et al.
6,327,410 B1 12/2001 Walt et al.
6,353,324 B1 3/2002 Uber, III et al.
6,355,431 B1 3/2002 Chee et al.
6,361,671 B1 3/2002 Mathies et al.
6,372,291 B1 4/2002 Hua et al.
6,376,256 B1 4/2002 Dunnington et al.
6,384,684 B1 5/2002 Redman-White
6,399,952 B1 6/2002 Maher et al.
6,403,957 B1 6/2002 Fodor et al.
6,406,848 B1 6/2002 Bridgham et al.
6,413,792 B1 7/2002 Sauer et al.
6,429,027 B1 8/2002 Chee et al.
6,432,360 B1 8/2002 Church
6,433,386 B1 8/2002 Yun et al.
6,459,398 B1 10/2002 Gureshnik et al.
6,465,178 B2 10/2002 Chappa et al.
6,475,728 B1 11/2002 Martin et al.
6,482,639 B2 11/2002 Snow et al.
6,485,944 B1 11/2002 Church et al.
6,490,220 B1 12/2002 Merritt et al.
6,499,499 B2 12/2002 Dantsker et al.
6,511,803 B1 1/2003 Church et al.
6,518,024 B2 2/2003 Choong et al.
6,518,146 B1 2/2003 Singh et al.
6,535,824 B1 3/2003 Mansky et al.
6,537,881 B1 3/2003 Rangarajan et al.
6,538,593 B2 3/2003 Yang et al.
6,545,620 B2 4/2003 Groeneweg
6,571,189 B2 5/2003 Jensen et al.
6,602,702 B1 8/2003 Mcdevitt et al.
6,605,428 B2 8/2003 Kilger et al.
6,613,513 B1 9/2003 Parce et al.
6,613,525 B2 9/2003 Nelson et al.
6,618,083 B1 9/2003 Chen et al.
6,624,637 B1 9/2003 Pechstein
6,627,154 B1 9/2003 Goodman et al.

(56) References Cited

U.S. PATENT DOCUMENTS

| | | | |
|---|---|---|---|
| 6,654,505 | B2 | 11/2003 | Bridgham et al. |
| 6,657,269 | B2 | 12/2003 | Migliorato et al. |
| 6,671,341 | B1 | 12/2003 | Kinget et al. |
| 6,682,899 | B2 | 1/2004 | Bryan et al. |
| 6,682,936 | B2 | 1/2004 | Kovacs |
| 6,686,638 | B2 | 2/2004 | Fischer et al. |
| 6,700,814 | B1 | 3/2004 | Nahas et al. |
| 6,703,660 | B2 | 3/2004 | Yitzchaik et al. |
| 6,716,629 | B2 | 4/2004 | Hess et al. |
| 6,762,022 | B2 | 7/2004 | Makarov et al. |
| 6,770,472 | B2 | 8/2004 | Manalis et al. |
| 6,780,591 | B2 | 8/2004 | Williams et al. |
| 6,787,111 | B2 | 9/2004 | Roach et al. |
| 6,795,006 | B1 | 9/2004 | Delight et al. |
| 6,806,052 | B2 | 10/2004 | Bridgham et al. |
| 6,828,100 | B1 | 12/2004 | Ronaghi |
| 6,831,994 | B2 | 12/2004 | Bridgham et al. |
| 6,841,128 | B2 | 1/2005 | Kambara et al. |
| 6,859,570 | B2 | 2/2005 | Walt et al. |
| 6,878,255 | B1 | 4/2005 | Wang et al. |
| 6,888,194 | B2 | 5/2005 | Yoshino |
| 6,898,121 | B2 | 5/2005 | Chien et al. |
| 6,906,524 | B2 | 6/2005 | Chung et al. |
| 6,919,211 | B1 | 7/2005 | Fodor et al. |
| 6,926,865 | B2 | 8/2005 | Howard |
| 6,927,045 | B2 | 8/2005 | Hadd et al. |
| 6,929,944 | B2 | 8/2005 | Matson |
| 6,939,451 | B2 | 9/2005 | Zhao et al. |
| 6,953,958 | B2 | 10/2005 | Baxter et al. |
| 6,958,216 | B2 | 10/2005 | Kelley et al. |
| 6,960,437 | B2 | 11/2005 | Enzelberger et al. |
| 6,969,488 | B2 | 11/2005 | Bridgham et al. |
| 6,998,274 | B2 | 2/2006 | Chee et al. |
| 7,008,550 | B2 | 3/2006 | Li et al. |
| 7,022,288 | B1 | 4/2006 | Boss |
| 7,033,754 | B2 | 4/2006 | Chee et al. |
| 7,037,687 | B2 | 5/2006 | Williams et al. |
| 7,045,097 | B2 | 5/2006 | Kovacs |
| 7,049,645 | B2 | 5/2006 | Sawada et al. |
| 7,060,431 | B2 | 6/2006 | Chee et al. |
| 7,067,886 | B2 | 6/2006 | Bonges, III et al. |
| 7,084,641 | B2 | 8/2006 | Brederlow et al. |
| 7,085,502 | B2 | 8/2006 | Shushakov et al. |
| 7,087,387 | B2 | 8/2006 | Gerdes et al. |
| 7,090,975 | B2 | 8/2006 | Shultz et al. |
| 7,091,059 | B2 | 8/2006 | Rhodes |
| 7,092,757 | B2 | 8/2006 | Larson et al. |
| 7,097,973 | B1 | 8/2006 | Zenhausern |
| 7,105,300 | B2 | 9/2006 | Parce et al. |
| 7,106,089 | B2 | 9/2006 | Nakano et al. |
| 7,129,554 | B2 | 10/2006 | Lieber et al. |
| 7,169,560 | B2 | 1/2007 | Lapidus et al. |
| 7,173,445 | B2 | 2/2007 | Fujii et al. |
| 7,190,026 | B2 | 3/2007 | Lotfi et al. |
| 7,192,745 | B2 | 3/2007 | Jaeger |
| 7,193,453 | B2 | 3/2007 | Wei et al. |
| 7,211,390 | B2 | 5/2007 | Rothberg et al. |
| 7,220,550 | B2 | 5/2007 | Keen |
| 7,223,371 | B2 | 5/2007 | Hayenga et al. |
| 7,223,540 | B2 | 5/2007 | Pourmand et al. |
| 7,226,734 | B2 | 6/2007 | Chee et al. |
| 7,229,799 | B2 | 6/2007 | Williams |
| 7,235,389 | B2 | 6/2007 | Lim et al. |
| 7,238,323 | B2 | 7/2007 | Knapp et al. |
| 7,239,188 | B1 | 7/2007 | Xu et al. |
| 7,244,559 | B2 | 7/2007 | Rothberg et al. |
| 7,244,567 | B2 | 7/2007 | Chen et al. |
| 7,264,929 | B2 | 9/2007 | Rothberg et al. |
| 7,264,934 | B2 | 9/2007 | Fuller |
| 7,265,929 | B2 | 9/2007 | Umeda et al. |
| 7,267,751 | B2 | 9/2007 | Gelbart et al. |
| 7,276,749 | B2 | 10/2007 | Martin et al. |
| 7,279,588 | B2 | 10/2007 | Hong et al. |
| 7,282,370 | B2 | 10/2007 | Bridgham et al. |
| 7,285,384 | B2 | 10/2007 | Fan et al. |
| 7,291,496 | B2 | 11/2007 | Holm-Kennedy |
| 7,297,518 | B2 | 11/2007 | Quake et al. |
| 7,298,475 | B2 | 11/2007 | Gandhi et al. |
| 7,303,875 | B1 | 12/2007 | Bock et al. |
| 7,317,216 | B2 | 1/2008 | Holm-Kennedy |
| 7,317,484 | B2 | 1/2008 | Dosluoglu et al. |
| 7,323,305 | B2 | 1/2008 | Leamon et al. |
| 7,335,526 | B2 | 2/2008 | Peters et al. |
| 7,335,762 | B2 | 2/2008 | Rothberg et al. |
| 7,359,058 | B2 | 4/2008 | Kranz et al. |
| 7,361,946 | B2 | 4/2008 | Johnson et al. |
| 7,363,717 | B2 | 4/2008 | Ekseth et al. |
| 7,381,936 | B2 | 6/2008 | Tan |
| 7,394,263 | B2 | 7/2008 | Pechstein et al. |
| 7,419,636 | B2 | 9/2008 | Aker et al. |
| 7,425,431 | B2 | 9/2008 | Church et al. |
| 7,455,971 | B2 | 11/2008 | Chee et al. |
| 7,462,452 | B2 | 12/2008 | Williams et al. |
| 7,462,709 | B2 | 12/2008 | Jaeger |
| 7,465,512 | B2 | 12/2008 | Wright et al. |
| 7,466,258 | B1 | 12/2008 | Akopyan et al. |
| 7,470,352 | B2 | 12/2008 | Eversmann et al. |
| 7,476,504 | B2 | 1/2009 | Turner |
| 7,482,153 | B2 | 1/2009 | Okada et al. |
| 7,482,677 | B2 | 1/2009 | Lee et al. |
| 7,499,513 | B1 | 3/2009 | Tetzlaff et al. |
| 7,515,124 | B2 | 4/2009 | Yaguma et al. |
| 7,534,097 | B2 | 5/2009 | Wong et al. |
| 7,538,827 | B2 | 5/2009 | Chou |
| 7,575,865 | B2 | 8/2009 | Leamon et al. |
| 7,576,037 | B2 | 8/2009 | Engelhardt et al. |
| 7,595,883 | B1 | 9/2009 | El Gamal et al. |
| 7,605,650 | B2 | 10/2009 | Forbes |
| 7,608,810 | B2 | 10/2009 | Yamada |
| 7,609,093 | B2 | 10/2009 | Sarig et al. |
| 7,609,303 | B1 | 10/2009 | Lee et al. |
| 7,612,369 | B2 | 11/2009 | Stasiak |
| 7,612,817 | B2 | 11/2009 | Tay |
| 7,614,135 | B2 | 11/2009 | Santini, Jr. et al. |
| 7,622,294 | B2 | 11/2009 | Walt et al. |
| 7,645,596 | B2 | 1/2010 | Williams et al. |
| 7,649,358 | B2 | 1/2010 | Toumazou et al. |
| 7,667,501 | B2 | 2/2010 | Surendranath et al. |
| 7,686,929 | B2 | 3/2010 | Toumazou et al. |
| 7,695,907 | B2 | 4/2010 | Miyahara et al. |
| 7,733,401 | B2 | 6/2010 | Takeda |
| 7,772,383 | B2 | 8/2010 | Chakrabarti et al. |
| 7,785,785 | B2 | 8/2010 | Pourmand et al. |
| 7,785,790 | B1 | 8/2010 | Church et al. |
| 7,794,584 | B2 | 9/2010 | Chodavarapu et al. |
| 7,821,806 | B2 | 10/2010 | Horiuchi |
| 7,824,900 | B2 | 11/2010 | Iwadate et al. |
| 7,838,226 | B2 | 11/2010 | Kamahori et al. |
| 7,842,377 | B2 | 11/2010 | Lanphere et al. |
| 7,842,457 | B2 | 11/2010 | Berka et al. |
| 7,859,029 | B2 | 12/2010 | Lee et al. |
| 7,859,291 | B2 | 12/2010 | Kim |
| 7,875,440 | B2 | 1/2011 | Williams et al. |
| 7,884,398 | B2 | 2/2011 | Levon et al. |
| 7,885,490 | B2 | 2/2011 | Heideman et al. |
| 7,888,013 | B2 | 2/2011 | Miyahara et al. |
| 7,888,015 | B2 | 2/2011 | Toumazou et al. |
| 7,888,708 | B2 | 2/2011 | Yazawa et al. |
| 7,890,891 | B2 | 2/2011 | Stuber et al. |
| 7,898,277 | B2 | 3/2011 | Weir |
| 7,923,240 | B2 | 4/2011 | Su |
| 7,927,797 | B2 | 4/2011 | Nobile et al. |
| 7,932,034 | B2 | 4/2011 | Esfandyarpour et al. |
| 7,948,015 | B2 | 5/2011 | Rothberg et al. |
| 7,955,995 | B2 | 6/2011 | Kakehata et al. |
| 7,960,776 | B2 | 6/2011 | Kim et al. |
| 7,972,828 | B2 | 7/2011 | Ward et al. |
| 7,981,362 | B2 | 7/2011 | Glezer et al. |
| 8,012,690 | B2 | 9/2011 | Berka et al. |
| 8,017,938 | B2 | 9/2011 | Gomez et al. |
| 8,035,175 | B2 | 10/2011 | Shim et al. |
| 8,052,863 | B2 | 11/2011 | Suzuki et al. |
| 8,067,731 | B2 | 11/2011 | Matyjaszczyk et al. |
| 8,072,188 | B2 | 12/2011 | Yorinobu et al. |

(56) References Cited

U.S. PATENT DOCUMENTS 8,114,591 B2 2/2012 Toumazou et al.
8,124,936 B1 2/2012 Lagna
8,133,698 B2 3/2012 Silver
8,138,496 B2 3/2012 Li et al.
8,154,480 B2 4/2012 Shishido et al.
8,199,859 B2 6/2012 Zerbe et al.
8,217,433 B1 7/2012 Fife
8,227,877 B2 7/2012 Lee et al.
8,231,831 B2 7/2012 Hartzell et al.
8,232,813 B2 7/2012 Burdett et al.
8,247,849 B2 8/2012 Fife et al.
8,248,356 B2 8/2012 Chen
8,262,900 B2 9/2012 Rothberg et al.
8,263,336 B2 9/2012 Rothberg et al.
8,264,014 B2 9/2012 Rothberg et al.
8,269,261 B2 9/2012 Rothberg et al.
8,277,628 B2 10/2012 Ronaghi et al.
8,293,082 B2 10/2012 Rothberg et al.
8,306,757 B2 11/2012 Rothberg et al.
8,313,625 B2 11/2012 Rothberg et al.
8,313,639 B2 11/2012 Rothberg et al.
8,317,999 B2 11/2012 Rothberg et al.
8,340,914 B2 12/2012 Gatewood et al.
8,343,856 B2 1/2013 Therrien et al.
8,349,167 B2 1/2013 Rothberg et al.
8,357,547 B2 1/2013 Lee et al.
8,361,713 B2 1/2013 Bridgham et al.
8,383,396 B2 2/2013 Kamahori et al.
8,415,716 B2 4/2013 Rothberg et al.
8,421,437 B2 4/2013 Levine
8,426,898 B2 4/2013 Rothberg et al.
8,426,899 B2 4/2013 Rothberg et al.
8,435,395 B2 5/2013 Rothberg et al.
8,441,044 B2 5/2013 Rothberg et al.
8,445,194 B2 5/2013 Drmanac et al.
8,445,945 B2 5/2013 Rothberg et al.
8,449,824 B2 5/2013 Sun
8,450,781 B2 5/2013 Rothberg et al.
8,470,164 B2 6/2013 Rothberg et al.
8,487,790 B2 7/2013 Fife et al.
8,492,800 B2 7/2013 Rothberg et al.
8,496,802 B2 7/2013 Rothberg et al.
8,502,278 B2 8/2013 Rothberg et al.
8,519,448 B2 8/2013 Rothberg et al.
8,524,057 B2 9/2013 Rothberg et al.
8,530,941 B2 9/2013 Rothberg et al.
8,535,513 B2 9/2013 Rothberg et al.
8,552,771 B1 10/2013 Jordan et al.
8,558,288 B2 10/2013 Rothberg et al.
8,575,664 B2 11/2013 Rothberg et al.
8,592,154 B2 11/2013 Rearick
8,653,567 B2 2/2014 Fife
8,658,017 B2 2/2014 Rothberg et al.
8,673,627 B2 3/2014 Nobile et al.
8,685,230 B2 4/2014 Rothberg et al.
8,685,298 B2 4/2014 Rockenschaub et al.
8,728,844 B1 5/2014 Liu et al.
8,731,847 B2 5/2014 Johnson et al.
8,742,469 B2 6/2014 Milgrew
8,742,472 B2 6/2014 Rothberg et al.
8,747,748 B2 6/2014 Li et al.
8,748,947 B2 6/2014 Milgrew
8,764,969 B2 7/2014 Rothberg et al.
8,766,327 B2 7/2014 Milgrew
8,766,328 B2 7/2014 Rothberg et al.
8,776,573 B2 7/2014 Rearick et al.
8,786,331 B2 7/2014 Jordan et al.
8,796,036 B2 8/2014 Fife et al.
8,821,798 B2 9/2014 Bustillo et al.
8,823,380 B2 9/2014 Levine et al.
8,841,217 B1 9/2014 Fife et al.
8,847,637 B1 9/2014 Guyton
8,912,005 B1 12/2014 Fife et al.
8,936,763 B2 * 1/2015 Rothberg ............. C12Q 1/6874
422/407
8,945,912 B2 2/2015 Bashir et al.
8,962,366 B2 2/2015 Putnam et al.
8,963,216 B2 2/2015 Fife et al.
8,983,783 B2 3/2015 Johnson et al.
9,023,674 B2 5/2015 Shen et al.
9,164,070 B2 10/2015 Fife
9,201,041 B2 12/2015 Dalton et al.
9,270,264 B2 2/2016 Jordan et al.
9,389,199 B2 7/2016 Cheng et al.
9,964,515 B2 5/2018 Rothberg et al.
2002/0012933 A1 1/2002 Rothberg et al.
2002/0042388 A1 4/2002 Cooper et al.
2002/0081714 A1 6/2002 Jain et al.
2002/0085136 A1 7/2002 Moon et al.
2002/0124663 A1 9/2002 Tokumoto et al.
2002/0150909 A1 10/2002 Stuelpnagel et al.
2002/0168678 A1 11/2002 Williams et al.
2003/0020334 A1 1/2003 Nozu
2003/0044833 A1 3/2003 Benchikh et al.
2003/0054396 A1 3/2003 Weiner
2003/0064366 A1 4/2003 Hardin et al.
2003/0068629 A1 4/2003 Rothberg et al.
2003/0108867 A1 6/2003 Chee et al.
2003/0119020 A1 6/2003 Stevens et al.
2003/0124572 A1 7/2003 Umek et al.
2003/0124599 A1 7/2003 Chen et al.
2003/0141928 A1 7/2003 Lee
2003/0141929 A1 7/2003 Casper et al.
2003/0148301 A1 8/2003 Aono et al.
2003/0152994 A1 8/2003 Woudenberg et al.
2003/0155942 A1 8/2003 Thewes
2003/0186262 A1 10/2003 Cailloux
2003/0211502 A1 11/2003 Sauer et al.
2003/0215791 A1 11/2003 Garini et al.
2003/0215857 A1 11/2003 Kilger et al.
2003/0224419 A1 12/2003 Corcoran et al.
2004/0002470 A1 1/2004 Keith et al.
2004/0023253 A1 2/2004 Kunwar et al.
2004/0079636 A1 4/2004 Hsia et al.
2004/0106211 A1 6/2004 Kauer et al.
2004/0121354 A1 6/2004 Yazawa et al.
2004/0130377 A1 7/2004 Takeda et al.
2004/0136866 A1 7/2004 Pontis et al.
2004/0146849 A1 7/2004 Huang et al.
2004/0185484 A1 9/2004 Costa et al.
2004/0185591 A1 9/2004 Hsiung et al.
2004/0197803 A1 10/2004 Yaku et al.
2004/0207384 A1 * 10/2004 Brederlow ....... G01N 33/48728
324/71.5
2005/0006234 A1 1/2005 Hassibi
2005/0009022 A1 1/2005 Weiner et al.
2005/0017190 A1 * 1/2005 Eversmann ........ G01N 27/4145
250/370.14
2005/0031490 A1 2/2005 Gumbrecht et al.
2005/0032075 A1 2/2005 Yaku et al.
2005/0058990 A1 3/2005 Guia et al.
2005/0093645 A1 5/2005 Watanabe et al.
2005/0095602 A1 5/2005 West et al.
2005/0100939 A1 5/2005 Namsaraev et al.
2005/0106587 A1 5/2005 Klapproth et al.
2005/0151181 A1 7/2005 Beintner et al.
2005/0156207 A1 7/2005 Yazawa et al.
2005/0156584 A1 7/2005 Feng
2005/0181440 A1 8/2005 Chee et al.
2005/0189960 A1 9/2005 Tajima
2005/0191698 A1 9/2005 Chee et al.
2005/0202582 A1 9/2005 Eversmann et al.
2005/0206548 A1 9/2005 Muramatsu et al.
2005/0212016 A1 9/2005 Brunner et al.
2005/0221473 A1 10/2005 Dubin et al.
2005/0230245 A1 10/2005 Morgenshtein et al.
2005/0230271 A1 * 10/2005 Levon ................ G01N 27/4148
205/789
2005/0239132 A1 10/2005 Klapproth
2005/0282224 A1 12/2005 Fouillet et al.
2006/0000772 A1 1/2006 Sano et al.
2006/0024711 A1 2/2006 Lapidus et al.
2006/0035400 A1 2/2006 Wu et al.
2006/0057025 A1 3/2006 Eversmann et al.

(56) References Cited

U.S. PATENT DOCUMENTS

| | | | |
|---|---|---|---|
| 2006/0057604 | A1 | 3/2006 | Chen et al. |
| 2006/0105373 | A1 | 5/2006 | Pourmand et al. |
| 2006/0141474 | A1 | 6/2006 | Miyahara et al. |
| 2006/0154399 | A1 | 7/2006 | Sauer et al. |
| 2006/0166203 | A1 | 7/2006 | Tooke |
| 2006/0182664 | A1 | 8/2006 | Peck et al. |
| 2006/0197118 | A1 | 9/2006 | Migliorato et al. |
| 2006/0199193 | A1 | 9/2006 | Koo et al. |
| 2006/0199493 | A1 | 9/2006 | Hartmann, Jr. et al. |
| 2006/0205061 | A1 | 9/2006 | Roukes |
| 2006/0219558 | A1 | 10/2006 | Hafeman et al. |
| 2006/0228721 | A1 | 10/2006 | Leamon et al. |
| 2006/0246497 | A1 | 11/2006 | Huang et al. |
| 2006/0269927 | A1 | 11/2006 | Lieber et al. |
| 2006/0289726 | A1 | 12/2006 | Paulus et al. |
| 2007/0087401 | A1 | 4/2007 | Neilson et al. |
| 2007/0092872 | A1 | 4/2007 | Rothberg et al. |
| 2007/0095663 | A1 | 5/2007 | Chou et al. |
| 2007/0096164 | A1 | 5/2007 | Peters et al. |
| 2007/0099173 | A1 | 5/2007 | Spira et al. |
| 2007/0138132 | A1 | 6/2007 | Barth |
| 2007/0172865 | A1 | 7/2007 | Hardin et al. |
| 2007/0212681 | A1 | 9/2007 | Shapiro et al. |
| 2007/0217963 | A1 | 9/2007 | Elizarov et al. |
| 2007/0231824 | A1 | 10/2007 | Chee et al. |
| 2007/0233477 | A1 | 10/2007 | Halowani et al. |
| 2007/0247170 | A1 | 10/2007 | Barbaro et al. |
| 2007/0250274 | A1 | 10/2007 | Volkov et al. |
| 2007/0262363 | A1 | 11/2007 | Tao et al. |
| 2007/0278111 | A1 | 12/2007 | Boussaad et al. |
| 2007/0278488 | A1 | 12/2007 | Hirabayashi et al. |
| 2008/0003142 | A1 | 1/2008 | Link et al. |
| 2008/0014589 | A1 | 1/2008 | Link et al. |
| 2008/0047836 | A1 | 2/2008 | Strand et al. |
| 2008/0063566 | A1 | 3/2008 | Matsumoto et al. |
| 2008/0085219 | A1 | 4/2008 | Beebe et al. |
| 2008/0096216 | A1 | 4/2008 | Quake |
| 2008/0111161 | A1 | 5/2008 | Sorge et al. |
| 2008/0121946 | A1 | 5/2008 | Youn et al. |
| 2008/0136933 | A1 | 6/2008 | Dosluoglu et al. |
| 2008/0164917 | A1 | 7/2008 | Floyd et al. |
| 2008/0178692 | A1 | 7/2008 | Jung et al. |
| 2008/0185616 | A1 | 8/2008 | Johnson et al. |
| 2008/0204048 | A1 | 8/2008 | Stasiak et al. |
| 2008/0205559 | A1 | 8/2008 | Iida |
| 2008/0210931 | A1 | 9/2008 | Truong et al. |
| 2008/0230386 | A1 | 9/2008 | Srinivasan et al. |
| 2008/0302672 | A1 | 12/2008 | Sandvik et al. |
| 2009/0030293 | A1 | 1/2009 | Cooper et al. |
| 2009/0048124 | A1 | 2/2009 | Leamon et al. |
| 2009/0062132 | A1 | 3/2009 | Borner |
| 2009/0075283 | A1 | 3/2009 | Liu et al. |
| 2009/0079414 | A1 | 3/2009 | Levon et al. |
| 2009/0120905 | A1 | 5/2009 | Kohl et al. |
| 2009/0121258 | A1 | 5/2009 | Kumar |
| 2009/0127689 | A1 | 5/2009 | Ye et al. |
| 2009/0149607 | A1 | 6/2009 | Karim et al. |
| 2009/0156425 | A1 | 6/2009 | Walt et al. |
| 2009/0170728 | A1 | 7/2009 | Walt et al. |
| 2009/0194416 | A1 | 8/2009 | Hsiung et al. |
| 2009/0273386 | A1 | 11/2009 | Korobeynikov et al. |
| 2010/0007326 | A1 | 1/2010 | Nakazato |
| 2010/0026814 | A1 | 2/2010 | Shimoda |
| 2010/0039146 | A1 | 2/2010 | Park et al. |
| 2010/0052765 | A1 | 3/2010 | Makino |
| 2010/0133547 | A1 | 6/2010 | Kunze et al. |
| 2010/0137143 | A1 | 6/2010 | Rothberg et al. |
| 2010/0176463 | A1 | 7/2010 | Koizumi et al. |
| 2010/0244106 | A1 | 9/2010 | Parker et al. |
| 2010/0273166 | A1 | 10/2010 | Garcia |
| 2010/0301398 | A1 | 12/2010 | Rothberg et al. |
| 2011/0037121 | A1 | 2/2011 | Lee et al. |
| 2011/0062972 | A1 | 3/2011 | Je et al. |
| 2011/0114827 | A1 | 5/2011 | Yamaoka et al. |
| 2011/0165557 | A1 | 7/2011 | Ah et al. |
| 2011/0169056 | A1 | 7/2011 | Wey et al. |
| 2011/0181253 | A1 | 7/2011 | Isham et al. |
| 2011/0236263 | A1 | 9/2011 | Sawada et al. |
| 2011/0262903 | A1 | 10/2011 | Davidson et al. |
| 2011/0275522 | A1 | 11/2011 | Rothberg et al. |
| 2011/0281737 | A1 | 11/2011 | Rothberg et al. |
| 2011/0281741 | A1 | 11/2011 | Rothberg et al. |
| 2011/0287945 | A1 | 11/2011 | Rothberg et al. |
| 2011/0299337 | A1 | 12/2011 | Parris et al. |
| 2012/0000274 | A1 | 1/2012 | Fife |
| 2012/0001056 | A1 | 1/2012 | Fife et al. |
| 2012/0001236 | A1 | 1/2012 | Fife |
| 2012/0001237 | A1 | 1/2012 | Fife et al. |
| 2012/0001615 | A1 | 1/2012 | Levine |
| 2012/0001646 | A1 | 1/2012 | Bolander et al. |
| 2012/0013392 | A1 | 1/2012 | Rothberg et al. |
| 2012/0034607 | A1 | 2/2012 | Rothberg et al. |
| 2012/0045368 | A1 | 2/2012 | Hinz et al. |
| 2012/0045844 | A1 | 2/2012 | Rothberg et al. |
| 2012/0055811 | A1 | 3/2012 | Rothberg et al. |
| 2012/0055813 | A1 | 3/2012 | Rothberg et al. |
| 2012/0056248 | A1 | 3/2012 | Fife |
| 2012/0060587 | A1 | 3/2012 | Babcock et al. |
| 2012/0129703 | A1 | 5/2012 | Rothberg et al. |
| 2012/0129732 | A1 | 5/2012 | Rothberg et al. |
| 2012/0135870 | A1 | 5/2012 | Rothberg et al. |
| 2012/0143531 | A1 | 6/2012 | Davey et al. |
| 2012/0154018 | A1 | 6/2012 | Sugiura |
| 2012/0161207 | A1 | 6/2012 | Homyk et al. |
| 2012/0168307 | A1 | 7/2012 | Fife |
| 2012/0173159 | A1 | 7/2012 | Davey et al. |
| 2012/0249192 | A1 | 10/2012 | Matsushita |
| 2012/0261274 | A1 | 10/2012 | Rearick et al. |
| 2012/0286771 | A1 | 11/2012 | Rothberg et al. |
| 2012/0326213 | A1 | 12/2012 | Bustillo et al. |
| 2012/0326767 | A1 | 12/2012 | Milgrew |
| 2012/0329043 | A1 | 12/2012 | Milgrew |
| 2012/0329192 | A1 | 12/2012 | Bustillo et al. |
| 2013/0001653 | A1 | 1/2013 | Milgrew et al. |
| 2013/0009214 | A1 | 1/2013 | Bustillo et al. |
| 2013/0056353 | A1 | 3/2013 | Nemirovsky et al. |
| 2013/0105868 | A1 | 5/2013 | Kalnitsky et al. |
| 2013/0135018 | A1 | 5/2013 | Kuo et al. |
| 2013/0210128 | A1 | 8/2013 | Rothberg et al. |
| 2013/0210182 | A1 | 8/2013 | Rothberg et al. |
| 2013/0210641 | A1 | 8/2013 | Rothberg et al. |
| 2013/0217004 | A1 | 8/2013 | Rothberg et al. |
| 2013/0217587 | A1 | 8/2013 | Rothberg et al. |
| 2013/0281307 | A1 | 10/2013 | Li et al. |
| 2013/0324421 | A1 | 12/2013 | Rothberg et al. |
| 2013/0341734 | A1 | 12/2013 | Merz |
| 2014/0080717 | A1 | 3/2014 | Li et al. |
| 2014/0148345 | A1 | 5/2014 | Li et al. |
| 2014/0234981 | A1 | 8/2014 | Zarkesh-Ha et al. |
| 2014/0235452 | A1 | 8/2014 | Rothberg et al. |
| 2014/0235463 | A1 | 8/2014 | Rothberg et al. |
| 2014/0308752 | A1 | 10/2014 | Chang et al. |
| 2015/0097214 | A1 | 4/2015 | Chen et al. |
| 2015/0197797 | A1 | 7/2015 | Rothberg et al. |
| 2016/0178568 | A1 | 6/2016 | Cheng et al. |

FOREIGN PATENT DOCUMENTS

| | | | |
|---|---|---|---|
| DE | 4232532 | | 4/1994 |
| DE | 4430811 | C1 | 9/1995 |
| DE | 102004044299 | | 3/2006 |
| DE | 102008012899 | | 9/2009 |
| EP | 1243925 | | 9/2002 |
| EP | 1371974 | | 12/2003 |
| EP | 1460130 | | 9/2004 |
| EP | 1557884 | | 7/2005 |
| EP | 1669749 | | 6/2006 |
| EP | 1870703 | | 12/2007 |
| EP | 1975246 | | 10/2008 |
| JP | S58-70155 | | 4/1983 |
| JP | S62-237349 | | 10/1987 |
| JP | H02-250331 | | 10/1990 |
| JP | H02-310931 | | 12/1990 |
| JP | H05-80115 | | 4/1993 |

(56) References Cited

FOREIGN PATENT DOCUMENTS

| | | | |
|---|---|---|---|
| JP | H10-78827 | | 3/1998 |
| JP | 2000-055874 | | 2/2000 |
| JP | 2002-221510 | | 8/2002 |
| JP | 2002-272463 | | 9/2002 |
| JP | 2003-279532 | | 10/2003 |
| JP | 2003-322633 | | 11/2003 |
| JP | 2004500033 | | 1/2004 |
| JP | 2004-343441 | | 12/2004 |
| JP | 2005-515475 | | 5/2005 |
| JP | 2005269646 | A | 9/2005 |
| JP | 2006138846 | | 6/2006 |
| JP | 2006-284225 | | 10/2006 |
| JP | 2007-512810 | | 5/2007 |
| JP | 2007-243003 | | 9/2007 |
| JP | 2008091556 | A | 4/2008 |
| JP | 2008-215974 | | 9/2008 |
| TW | 200510714 | | 3/2005 |
| TW | 200946904 | | 11/2009 |
| WO | WO-1999019717 | | 4/1999 |
| WO | WO-2002024322 | | 3/2002 |
| WO | WO-2004040291 | | 5/2004 |
| WO | WO-2004048962 | | 6/2004 |
| WO | WO-2004081234 | | 9/2004 |
| WO | WO-2005015156 | | 2/2005 |
| WO | WO-2005054431 | | 6/2005 |
| WO | WO-2005062049 | | 7/2005 |
| WO | WO-2005084367 | | 9/2005 |
| WO | WO-2005090961 | | 9/2005 |
| WO | WO-2006056226 | | 6/2006 |
| WO | WO-2007002204 | | 1/2007 |
| WO | 2007135161 | A1 | 11/2007 |
| WO | WO-2008058282 | | 5/2008 |
| WO | WO-2008107014 | | 9/2008 |
| WO | WO-2009041917 | | 4/2009 |
| WO | WO-2010047804 | | 4/2010 |
| WO | WO-2010138186 | | 12/2010 |
| WO | WO-2012046137 | | 4/2012 |
| WO | WO-2012152308 | | 11/2012 |
| WO | WO-2014/077783 | | 5/2014 |

OTHER PUBLICATIONS

Akiyama et al., "Ion-Sensitive Field-Effect Transistors with Inorganic Gate Oxide for pH Sensing", IEEE Transactions on Electron Devices, vol. 29, No. 12, 1982, pp. 1936-1941.
Anderson, et al., "A system for multiplexed direct electrical detection of DNA synthesis", Sensors and Actuators B: Chemical, vol. 129, No. 1, Jan. 2008, pp. 79- 86.
AU2011226767, Search Information Statement, Oct. 26, 2011, pp. 1-3.
Bandettini et al., "Processing Strategies for Time-Course Data Sets in Functional MRI of the Human Brain," MRM, vol. 30, 1993, pp. 161-172.
Bandiera et al., "A fully electronic sensor for the measurement of cDNA hybridization kinetics", Biosensors & Bioelectronics, vol. 22, Nos. 9-10, Apr. 15, 2007, pp. 2108-2114.
Barbaro et al., "A Charge-Modulated FET for Detection of Biomolecular Processes: Conception, Modeling, and Simulation", IEEE Transactions on Electron Devices, vol. 53, No. 1, 2006, pp. 158-166.
Barbaro et al., "A CMOS, Fully Integrated Sensor for Electronic Detection of DNA Hybridization", IEEE Electronic Device Letters, vol. 27, No. 7, 2006, pp. 595-597.
Barbaro et al., "Fully electronic DNA hybridization detection by a standard CMOS biochip", Sensors and Actuators B: Chemical, vol. 118, 2006, pp. 41-46.
Bashford et al., "Automated bead-trapping apparatus and control system for single-molecule DNA sequencing", Optics Express, vol. 16, No. 5, Mar. 3, 2008, pp. 34453455.
Baumann et al., "Microelectronic sensor system for microphysiological application on living cells", Sensors and Actuators B: Chemical, vol. 55, No. 1, Apr. 1999, pp. 77-89.
Bausells et al., "Ion-sensitive field-effect transistors fabricated in a commercial CMOS technology", Sensors and Actuators B: Chemical, vol. 57, Nos. 1-3, 1999, pp. 56-62.
Beer et al., "Anion Recognition and Sensing: The State of the Art and Future Perspectives", Angewandte Chemie International Edition, vol. 40, No. 3, Feb. 2001, pp. 487-516.
Bergveld, "ISFET, Theory and Practice", IEEE Sensor Conference, Toronto, Oct. 2003, pp. 1-26.
Bergveld, "Thirty years of ISFETOLOGY What happened in the past 30 years and what may happen in the next 30 years", Sensors and Actuators B: Chemical, vol. 88, No. 1, Jan. 2003, pp. 1-20.
Besselink et al., "ISFET Affinity Sensor", Chapter 12 in Methods in Biotechnology, Affinity Biosensors: Techniques and Protocols, vol. 7, 1998, pp. 173-185.
Bobrov et al., "Chemical sensitivity of an ISFET with Ta2O5 membrane in strong acid and alkaline solutions", Sensors and Actuators B: Chemical, vol. 3, No. 1, Jan. 1991, pp. 75-81.
Bockelmann et al., "Detecting DNA by field effect transistor arrays", Proceedings of the 2006 IFIP International Conference on Very Large Scale Integration, 2006, pp. 164-168.
Bousse et al., "A process for the combined fabrication of ion sensors and CMOS circuits", IEEE Electron Device Letters, vol. 9, No. 1, Jan. 1988, pp. 44-46.
Bousse et al., "Zeta potential measurements of Ta2O5 and SiO2 thin films" Journal of Colloid and Interface Science, vol. 147, No. 1, Nov. 1991, pp. 22-32.
Brenner, et al., "Gene expression analysis by massively parallel signature sequencing (MPSS) on microbead arrays", Nature Biotechnology, vol. 18, No. 6, Jun. 2000, pp. 630-634.
Brzozka et al., "Enhanced performance of potassium CHEMFETs by optimization of a polysiloxane membrane", Sensors and Actuators B: Chemical, 18-19, 1994, pp. 38-41.
Chan et al., "An Integrated ISFETs Instrumentation System in Standard CMOS Technology", IEEE Journal of Solid-State Circuits, vol. 45, No. 9, Sep. 2010, pp. 1923-1934.
Chen et al., "Nanoscale field effect transistor for biomolecular signal amplification", Applied Physics Letter, vol. 91, No. 24, Nov. 2007, pp. 243511-1-243511-3.
Chen et al., "Silicon-based nanoelectronic field-effect pH sensor with local gate control", Applied Physics Letter, vol. 89, Nov. 2006, pp. 223512-1-223512-3.
Chin et al., "Titanium Nitride Membrane Application to Extended Gate Field Effect Transistor pH Sensor Using VLSI Technology", Japanese Journal of Applied Physics, vol. 40, Part 1, No. 11, Nov. 2001, pp. 6311-6315.
Chou et al., "Letter to the Editor on Simulation of Ta2O5-gate ISFET temperature characteristics", Sensors and Actuators B: Chemical, vol. 80, 2001, pp. 290-291.
Chou et al., "Simulation of Ta2O5-gate ISFET temperature characteristics", Sensor and Actuators B: Chemical, vol. 71, Nos. 1-2, Nov. 2000, pp. 73-76.
Chung et al., "ISFET interface circuit embedded with noise rejection capability", Electronics Letters, vol. 40, No. 18, e-pub, 2 Pages, Sep. 2, 2004, pp. 1115-1116.
Chung et al., "ISFET performance enhancement by using the improved circuit techniques", Sensors and Actuators B: Chemical, vol. 113, No. 1, Jan. 2006, pp. 555-562.
Chung et al., "New ISFET interface circuit design with temperature Compensation", CiteSeerx—URL: http://citeseerx.ist.psu.edu/viewdoc/download?doi=10.1.1.95.2321&rep=rep1-&type=pdf, 2006, pp. 1.
Chung et al., "New ISFET Interface Circuit Design with Temperature Compensation", Microelectronics Journal, vol. 37, No. 10, Oct. 1, 2006, pp. 1105-1114.
Chung et al., "Temperature compensation electronics for ISFET readout applications", Biomedical Circuits and Systems, IEEE International Workshop Singapore, Dec. 1, 2004, pp. 305-308.
Cobben et al., "Transduction of Selective Recognition of Heavy Metal Ions by Chemically Modified Field Effect Transistors (CHEMFETs)",Journal of the American Chemical Society, vol. 114, No. 26, Dec. 1992, pp. 10573-10582.

(56) References Cited

OTHER PUBLICATIONS

Dahl et al., "Circle-to-circle amplification for precise and sensitive DNA analysis," Proceedings of the National Academy of Sciences, vol. 101, No. 13, Mar. 2004, pp. 4548-4553.
Dazhong et al., "Research of CMOS Biosensor IC for Extracellular Electrophysiological Signal Recording and pH value Measuring", Solid-State and Integrated-Circuit Technology, 9th International Conference, NJ USA, Oct. 20, 2008, pp. 2557-2560.
Dorf, "The Electrical Engineering Handbook", University of California, Davis, CRC Press, 2 edition, Chapter 3—Linear Circuit Analysis, Jun. 25, 2004, pp. 3-1 to 3-66.
Eastman Kodak Company, "Image Sensor Solutions-Full-Frame CCD Image Sensor Performance Specification", http://www.physics.csbsju.edu/370/photometry/manuals/kaf-1001e.pdf, Feb. 19, 2001.
Eijkel et al., "Measuring Donnan-related phenomena using a solid-state ion sensor and a concentration-step method", Journal of Membrane Science, vol. 127, May 1997, pp. 203-221.
Eijkel, "Potentiometric detection and characterization of adsorbed protein using stimulus-response measurement techniques", Thesis, Sep. 3, 1955, pp. 1-147; pp. 160-192.
Eltoukhy et al., "A 0.18um CMOS 10-6 lux bioluminescence detection system-on-chip", 2004 IEEE Inti Solid States Conference. Digest of Technical Papers. Session 12, Microsystems/12.3, Feb. 17, 2004. pp. 1-3.
Eltoukhy et al., "A. 0.18-um CMOS Bioluminescence Detection Lab-on-Chip", IEEE Journal of Solid-State Circuits, vol. 41, No. 3, Apr. 2006, pp. 651-662.
EP09798251.6, Extended Search Report, dated Aug. 27, 2013, 6 pages.
EP09822323.3, Extended Search Report, dated May 27, 2015, 8 pages.
EP10780930.3, Search Report, dated Jun. 15, 2015, 3 pages.
EP10780935.2, Search Report dated Jun. 9, 2015, 5 pages.
EP10780935.2, Supplementary Search Report, dated Sep. 30, 2015.
EP10857377.5, Search Report, dated Jun. 26, 2015, 3 pages.
EP11801437.2, Extended Search Report, dated Jul. 25, 2013, 10 pages.
EP11801439.8, Extended Search Report, dated Mar. 7, 2014, 9 pages.
EP11804218.3, Extended Search Report, dated Jul. 11, 2013, 3 pages.
EP11827128.7, Search Report, dated Aug. 1, 2013, 5 pages.
EP13161312.7, Extended Search Report, dated Oct. 15, 2013, 8 pages.
EP13163995.7, "EP Office Action dated Jul. 9, 2014".
EP13163995.7, Extended Search Report, dated Aug. 20, 2013, 6 pages.
EP13164768.7, Extended Search Report, dated Aug. 20, 2013, 6 pages.
EP13174555.6, Extended Search Report, dated Dec. 4, 2013, 8 pages.
EP13174555.6, Search Report, dated Nov. 21, 2013, 5 pages.
EP13177039.8, Search Report, dated Nov. 21, 2013, 9 pages.
EP13177590.0, Search Report, dated Nov. 20, 2013, 5 pages.
EP14152861.2, Search Report, dated Jul. 7, 2014, 5 pages.
EP15170247.9, Search Report, dated Nov. 10, 2015, 4 pages.
EP17167536.6, Search Report, dated Nov. 7, 2017, 13 pages.
Eriksson et al., "Pyrosequencing™ Technology at Elevated Temperature" Electrophoresis, vol. 25, No. 1, Jan. 2004, pp. 20-27.
Esfandyarpour et al., "Gate-controlled microfluidic chamber with magnetic bead for DNA sequencing-by-synthesis technology", Proc 5th Intl Conf Nanochannels, Microchannels and Minichannels, Puebla, Mexico, Jun. 18-20, 2007, pp. 1-5.
Eversmann et al., "A 128.times.128 CMOS Biosensor Array for Extracellular Recording of Neural Activity", IEEE J. Solid-State Circ., vol. 38, No. 12, Dec. 12, 2003, pp. 2306-2317.
Faramarzpour et al., "CMOS-Based Active Pixel for Low-Light Level Detection: Analysis and Measurements", IEEE Trans Electron Devices, vol. 54, No. 12, Dec. 2007, pp. 3229-3237.
Finn et al., "Towards an Optimization of FET-Based Bio-Sensors", European Cells and Materials, vol. 4, Sup 2, 2002, pp. 21-23.
Fraden, "Handbook of Modern Sensors-Physics, Designs, and Applications", 17.3.2 CHEMFET Sensors, 1996, pp. 499-501.
Fritz et al., "Electronic detection of DNA by its intrinsic molecular charge", Proceedings of the National Academy of Sciences, vol. 99, No. 22, Oct. 29, 2002, pp. 14142-14146.
Gardner et al., "Enhancing electronic nose performance by sensor selection using a new integer-based genetic algorithm approach", Sensors and Actuators B: Chemical, vol. 106, No. 1, Apr. 2005, pp. 114-121.
GB0811656.8, Search Report, dated Mar. 12, 2010.
GB0811656.8, Search Report, dated Sep. 21, 2009.
GB0811657.6, Search Report, dated Oct. 26, 2009.
Gracia et al., "Test Structures for ISFET Chemical Sensors", IEEE Proceedings of the 1992 International Conference on Microelectronic Test Structures, vol. 5, 1992, pp. 156-159.
Hammond et al., "A System-on-Chip Digital pH Meter for Use in a Wireless Diagnostic Capsule", IEEE Transactions on Biomedical Engineering, vol. 52, No. 4, May 2005, pp. 687-694.
Hammond et al., "Design of a Single-Chip pH Sensor Using a Conventional 0.6-.mu.m CMOS Process", IEEE Sensors Journal, vol. 4, No. 6, 2004, pp. 706-712.
Hammond et al., "Encapsulation of a liquid-sensing microchip using SU-8 photoresist", MicroElectronic Engineering, vols. 73-74, Jun. 2004, pp. 893-897.
Hammond et al., "Genomic sequencing and analysis of a Chinese Hamster ovary cell line using Illumina sequencing technology", BMC Genomics, vol. 12, No. 67, Jan. 2011, pp. 1-8.
Hammond et al., "Performance and system-on-chip integration of an unmodified CMOS ISFET", Sensors and Actuators B: Chemical, vols. 111-112, Nov. 2005, pp. 254-258.
Han "Label-free detection of biomolecules by a field-effect transistor microarray biosensor with bio-functionalized gate surfaces," Masters Dissertation, RWTH Aachen University, 2006, pp. 1-63.
Han et al., "Detection of DNA hybridization by a field-effect transistor with covalently attached catcher molecules", Surface and Interface Analysis, vol. 38, No. 4,, Apr. 2006, pp. 176-181.
Hanshaw et al., "An indicator displacement system for fluorescent detection of phosphate oxyanions under physiological conditions", Tetrahedron Letters, vol. 45, No. 47, Nov. 15, 2004, pp. 8721-8724.
Hara et al., "Dynamic response of a Ta2O5-gate pH-sensitive field-effect transistor", Sensors Actuators B: Chemical, vol. 32, No. 2, May 1996, pp. 115-119.
Hermon et al., "Miniaturized bio-electronic hybrid for chemical sensing applications", Tech Connect News, Apr. 22, 2008, pp. 1.
Hideshima et al., "Detection of tumor marker in blood serum using antibody-modified field effect transistor with optimized BSA blocking", Sensors and Actuations B: Chemical, vol. 161, No. 1, Jan. 2012, pp. 146-150.
Hijikata et al., "Identification of a Single Nucleotide Polymorphism in the MXA Gene Promoter (T/T at nt-88) Correlated with the Response of Hepatitis C Patients to Interferon", Intervirology, vol. 43, No. 2, 2000, pp. 124-127.
Hizawa et al., "32.times.32 pH Image Sensors for Real Time Observation of Biochemical Phenomena", Transducers & Eurosensors '07, 14th Intl. Conf. on Solid-State, Actuators and Microsystems, Lyon, France, Jun. 10-14, 2007, pp. 1311-1312.
Hizawa et al., "Fabrication of a two-dimensional pH image sensor using a charge transfer technique", Sensors and Actuators B: Chemical, vol. 117, No. 2, Oct. 2006, pp. 509-515.
Hizawa, et al., "Sensing Characteristics of Charge Transfer Type pH Sensor by Accumulative Operation", IEEE Sensors, EXCO, Daegu, Korea, Oct. 22-25, 2006, pp. 144-147.
Ingebrandt et al., "Label-free Detection of DNA using Field-Effect Transistors", Physica status solidi A, vol. 203, No. 14, Nov. 2006, pp. 3399-3411.
Izuru, "Kojien", published by Owanami, Fourth Edition, 1991, pp. 2683.
Jakobson et al., "Ion-Sensitive Field-Effect Transistors in Standard CMOS Fabricated by Post Processing", IEEE Sensors Journal, vol. 2, No. 4, Aug. 2002, pp. 279-287.

(56) References Cited

OTHER PUBLICATIONS

Jakobson et al., "Low frequency noise and drift in Ion Sensitive Field Effect Transistors", Sensors Actuators B: Chemical, vol. 68, Nos. 1-3, Aug. 2000, pp. 134-139.
Ji et al., "A CMOS contact imager for locating individual cells", IEEE International Symposium on Circuits and Systems, 2006, pp. 3357-3360.
Ji et al., "Contact Imaging: Simulation and Experiment", IEEE Trans Circuits Systems-I: Regular Papers, vol. 54, No. 8, 2007, pp. 1698-1710.
Kim et al., "An FET-type charger sensor for highly sensitive detection of DNA sequence", Biosensors & Bioelectronics, vol. 20, No. 1, Jul. 30, 2004, pp. 69-74.
Klein, "Time effects of ion-sensitive field-effect transistors", Sensors and Actuators, vol. 17, Nos. 1-2, May 1989, pp. 203-208.
Koch et al., "Protein detection with a novel ISFET-based zeta potential analyzer", Biosensors & Bioelectronics, vol. 14, No. 4, Apr. 1999, pp. 413-421.
Krause et al., "Extended Gate Electrode Arrays for Extracellular Signal Recordings", Sensors and Actuators B: Chemical, vol. 70, Nos. 1-3, Nov. 2000, pp. 101-107.
Kruise et al., "Detection of protein concentrations using a pH-step titration method", Sensors Actuators B: Chemical, vol. 44, Nos. 1-3, Oct. 1997, pp. 297-303.
Leamon et al., "A Massively Parallel PicoTiterPlate Based Platform for Discrete Picoliter-Scale Polymerase Chain Reactions", Electrophoresis, vol. 24, No. 21, Nov. 24, 2003, pp. 3769-3777.
Leamon et al., "Cramming More Sequencing Reactions onto Microreactor Chips", Chemical Reviews, vol. 107, No. 8, Aug. 2007, pp. 3367-3376.
Lee et al. "An Enhanced Glucose Biosensor Using Charge Transfer Techniques" Biosensors & Bioelectronics, vol. 24, No. 4, Dec. 2008, pp. 650-656.
Lee et al., "Ion-sensitive Field-Effect Transistor for Biological Sensing", Sensors, vol. 9, No. 9, 2009, pp. 7111-7131.
Li et al., "Sequence-Specific Label-Free DNA Sensors based on Silico Nanowires", Nano Letters, vol. 4, No. 2, Jan. 2004, pp. 245-247.
Ligler et al., "Array biosensor for detection of toxins", Analytical and Bioanalytical Chemistry, vol. 377, No. 3, Oct. 2003, pp. 469-477.
Lin et al., "Practicing the Novolac deep-UV portable conformable masking technique", Journal of Vacuum Science and Technology, vol. 19, No. 4, 1981, pp. 1313-1319.
Liu et al., "An ISFET based sensing array with sensor offset compensation and pH sensitivity enhancement", IEEE International Symposium on Circuits and Systems, Jun. 2, 2010, pp. 2283-2286.
Lohrengel et al., "A new microcell or microreactor for material surface investigations at large current densities", Electrochimica Acta, vol. 49, Nos. 17-18, Jul. 2004, pp. 2863-2870.
Lui et al., "A Test Chip for ISFET/CMNOS Technology Development", IEEE International Conference on Microelectronic Test Structures, vol. 9, 1996, pp. 123-128.
Maki et al., "Nanowire-transistor based ultra-sensitive DNA methylation detection", Biosensors & Bioelectronics, vol. 23, No. 6, Jan. 2008, pp. 780-787.
Margulies et al., "Genome Sequencing in Microfabricated High-Density Picolitre Reactors", Nature, vol. 437, No. 7057, Sep. 15, 2005, pp. 376-380. (Epub Jul. 31, 2005.).
Marshall et al., "DNA chips: an array of possibilities", Nature Biotechnology, vol. 16, No. 1, Jan. 1998, pp. 27-31.
Martel et al., "Single and multi-wall carbon nanotube field effect transistors", Applied Physics Letters, vol. 73, No. 17, Oct. 1998, pp. 2447-2449.
Martinoia et al., "A behavioral macromodel of the ISFET in SPICE", Sensors and Actuators B: Chemical, vol. 62, No. 3, Mar. 2000, pp. 182-189.
Martinoia et al., "Development of ISFET Array-Based Microsystems for Bioelectrochemical measurements of cell populations", Biosensors & Bioelectronics, vol. 16, Nos. 9-12, Dec. 2001, pp. 1043-1050.
Matsuo et al. "Charge Transfer Type pH Sensor with Super High Sensitivity" 14th International Conference on Solid-State Sensors Actuators and Microsystems, France, Jun. 10-14, 2007, pp. 1881-1884.
Matula, "Electrical Resistivity of Copper, Gold, Palladium, and Silver", Journal of Physical and Chemical Reference Data, vol. 8, No. 4, 1979, pp. 1147-1298.
Medoro et al., "A Lab-on-Chip for Cell Detection and Manipulation", IEEE Sensors Journal, vol. 3, No. 3, 2003, pp. 317-325.
Meyburg et al., "N-Channel field-effect transistors with floating gates for extracellular recordings", Biosensors and Bioelectronics, vol. 21, No. 7, Jan. 15, 2006, pp. 1037-1044.
Milgrew et al., "A 16×16 CMOS proton camera array for direct extracellular imaging of hydrogen-ion activity", IEEE Inti Solid-State Circuits Conference, Session 32:24, 2008, pp. 590-591,638.
Milgrew et al., "A large transistor-based sensor array chip for direct extracellular imaging", Sensors and Actuators B: Chemical, vols. 111-112, Nov. 2005, pp. 347-353.
Milgrew et al., "A Proton Camera Array Technology for Direct Extracellular Ion Imaging", IEEE International Symposium on Industrial Electronics, 2008, pp. 2051-2055.
Milgrew et al., "Matching the transconductance characteristics of CMOS ISFET arrays by removing trapped charge", IEEE Transactions on Electronic Devices, vol. 55, No. 4, 2008, pp. 1074-1079.
Milgrew et al., "Microsensor Array Technology for Direct Extracellular Imaging", Dept Electronic and EE, University of Glasgow, Apr. 5, 2006, pp. 1-23.
Milgrew et al., "The Development of Scalable Sensor Arrays Using Standard CMOS Technology", Sensors and Actuators B: Chemical, vol. 103, Nos. 1-2, Sep. 2004, pp. 37-42.
Milgrew et al., "The fabrication of scalable multi-sensor arrays using standard CMOS technology", IEEE Custom Integrated Circuits Conference, 2003, pp. 513-516.
Miyahara et al., "Biochip Using Micromachining Technology", Journal of Institute of Electrostatics, Japan, vol. 27, No. 6, 2003, pp. 268-272.
Miyahara et al., "Direct Transduction of Primer Extension into Electrical Signal Using Genetic Field Effect Transistor", Micro Total Analysis Systems, vol. 1, Proceedings of UTAS 2004, 8th International Conference on Miniaturized Systems for Chemistry and Life Sciences, Malmo, Sweden, Sep. 26-30, 2004, pp. 303-305.
Miyahara et al., "Potentiometric Detection of DNA Molecules Using Field Effect Transistor", The Japan Society of Applied Physics, No. 3, 2003, pp. 1180, 30A-S2.
Morgenshtein et al., "Wheatstone-Bridge readout interface for ISFET/REFET applications", Sensors and Actuators B: Chemical, vol. 98, No. 1, Mar. 2004, pp. 18-27.
Moriizumi, "Biosensors", Oyo Buturi (monthly publication of the Japan Society of Applied Physics), vol. 54, No. 2, Feb. 10, 1985, pp. 98-114.
Naidu et al., "Introduction to Electrical Engineering", Chapter 1—Fundamental Concepts of Electricity, McGraw Hill Education (India) Private Limited, 1995, pp. 1-10.
Nakazato et al., "28p-Y-7 ISFET sensor array integrated circuits based on the standard CMOS process", The 55th annual meeting of the Japan Society of Applied Physics, Book of Abstracts, Mar. 27, 2008, p. 70.
Nakazato, "An Integrated ISFET Sensor Array", Sensors, Nov. 2009, vol. 9, No. 11, ISSN:1424-8220, [online], Internet, URL, http://www.mdpi.com/1424-8220/9/11/8831/pdf, Nov. 2009, pp. 8831-8851.
Neaman, "Electronic Circuit Analysis and Design", McGraw Hill Higher Education, 2nd Edition, Chapter 6—Basic FET Amplifiers, (reference will be uploaded in 2 parts due to size) part 1 of 2, Dec. 1, 2000, pp. 313-345.
Neaman, "Electronic Circuit Analysis and Design", McGraw Hill Higher Education, 2nd Edition, Chapter 6—Basic FET Amplifiers, (reference will be uploaded in 2 parts due to size) part 2 of 2, Dec. 1, 2000, pp. 346-381.

(56) References Cited

OTHER PUBLICATIONS

Nishiguchi et al., "Si nanowire ion-sensitive field-effect transistors with a shared floating gate", Applied Physics Letters, vol. 94, Apr. 2009, pp. 163106-1 to 163106-3.
Nyren et al., "Enzymatic Method for Continuous Monitoring of Inorganic Pyrophosphate Synthesis", Analytical Biochemistry, vol. 151, No. 2, Dec. 1985, pp. 504-509.
Oelßner et al., "Encapsulation of ISFET sensor chips", Sensors Actuators B: Chemical, vol. 105, No. 1, Feb. 2005, pp. 104-117.
Oelßner et al., "Investigation of the dynamic response behavior of ISFET pH sensors by means of laser Doppler velocimetry (LDV)", Sensors and Actuators B: Chemical, vol. 27, Nos. 1-3, Jun. 1995, pp. 345-348.
Offenhausser et al., "Field-Effect transistor array for monitoring electrical activity from mammalian neurons in culture", Biosensors & Bioelectronics, vol. 12, No. 8, Jan. 1997, pp. 819-826.
Ohno et al., "Electrolyte-Gated Graphene Field-Effect Transistors for Detecting pH and Protein Adsorption", Nano Letters, vol. 9, No. 9, Jul. 28, 2009, pp. 3318-3322.
Palan et al., "New ISFET sensor interface circuit for biomedical applications", Sensors and Actuators B: Chemical, vol. 57, Nos. 1-3, Sep. 1999, pp. 63-68.
Park et al., "ISFET glucose sensor system with fast recovery characteristics by employing electrolysis", Sensors and Actuators B: Chemical, vol. 83, Nos. 1-3, Mar. 15, 2002, pp. 90-97.
Patolsky et al., "Nanowire-Based Biosensors", Analytical Chemistry, vol. 78, No. 13, Jul. 1, 2006, pp. 4261-4269.
PCT/JP2005/001987, Search Report, dated Apr. 5, 2005.
PCT/JP2005/015522, Search Report, dated Sep. 27, 2005.
PCT/US2007/025721 Written Opinion dated Jun. 16, 2009.
PCT/US2007/025721, Declaration of Non-Establishment of International Search Report.
PCT/US2009/003766, Search Report and Written Opinion, dated Apr. 8, 2010.
PCT/US2009/003797, Search Report and Written Opinion, dated Mar. 12, 2010.
PCT/US2009/005745 Search Report and Written Opinion, dated Dec. 11, 2009.
PCT/US2010/001543, Search Report and Written Opinion, dated Oct. 13, 2010.
PCT/US2010/001547, Search Report and Written Opinion, dated Aug. 5, 2010.
PCT/US2010/001553, Search Report and Written Oiion, dated Jul. 28, 2010.
PCT/US2010/048835, Search Report and Written Opinion, dated Dec. 16, 2010.
PCT/US2011/042655, Search Report and Written Opinion, dated Oct. 21, 2011.
PCT/US2011/042660, Search Report, dated Nov. 2, 2011.
PCT/US2011/042665. Search Report dated Nov. 2, 2011.
PCT/US2011/042668, Search Report, dated Oct. 28, 2011.
PCT/US2011/042669, Search Report and Written Opinion, dated Jan. 9, 2012.
PCT/US2011/042683, Search Report and Written Opinion, dated Feb. 16, 2012.
PCT/US2012/058996. Search Report and Written Opinion dated Jan. 22, 2013.
PCT/US2012/071471, Search Report and Written Opinion, dated Apr. 24, 2013.
PCT/US2012/071482, Search Report and Written Opinion, dated May 23, 2013.
PCT/US2013/022129, Search Report and Written Opinion, dated Aug. 9, 2013.
PCT/US2013/022140, Search Report and Written Opinion, dated May 2, 2013.
PCT/US2014/020887, Search Report and Written Opinion, dated May 30, 2014.
PCT/US2014/020892, Search Report and Written Opinion, dated Jun. 3, 2014.
PCT/US2014/040923, Search Report and Written Opinion, dated Sep. 1, 2014.
PCT/US2015/066052, Search Report and Written Opinion, dated Apr. 7, 2016.
Poghossian et al., "Functional testing and characterization of ISFETs on wafer level by means of a micro-droplet cell", Sensors, vol. 6, No. 4, Apr. 2006, pp. 397-404.
Pollack et al., "Genome-wide analysis of DNA copy-number changes using cDNA microarrays", Nature Genetics, vol. 23, No. 1, Sep. 1999, pp. 41-46.
Pourmand et al., "Direct electrical detection of DNA synthesis", Proceedings of the National Academy of Sciences, vol. 103, No. 17, Apr. 2006, pp. 6466-6470.
Pouthas et al., "Spatially resolved electronic detection of biopolymers", Physical Review, vol. 70, No. 3, Sep. 2004, pp. 031906-1-031906-8.
Premanode et al., "A composite ISFET readout circuit employing current feedback", Sensors Actuators B: Chemical, vol. 127, No. 2, Nov. 2007, pp. 486-490.
Premanode et al., "A novel, low power biosensor for real time monitoring of creatinine and urea in peritoneal dialysis", Sensors and Actuators B: Chemical, vol. 120, No. 2, Jan. 2007, pp. 732-735.
Premanode et al., "Drift Reduction in Ion-Sensitive FETs using correlated double sampling", Electronics Letters, vol. 43, No. 16, Aug. 2, 2007, pp. 857-859.
Premanode et al., "Ultra-low power precision ISFET readout using global current feedback", Electronic Letters, vol. 42, No. 22, Oct. 26, 2006, pp. 1264-1265.
Purushothaman et al., "Protons and single nucleotide polymorphism detection: A simple use for the Ion Sensitive Field Effect Transistor", Sensors and Actuators B: Chemical, vol. 114, No. 2, Apr. 2006, pp. 964-968.
Purushothaman et al., "Towards Fast Solid State DNA Sequencing", IEEE ISCAS Proceedings, Circuits and Systems, vol. 4, 2002, pp. IV-169-IV-172.
Rodriguez-Villegas, "Solution to trapped charge in FGMOS transistors", Electronics Letters, vol. 39, No. 19, Oct. 2003, pp. 1416-1417.
Ronaghi et al., "A Sequencing Method Based on Real-Time Pyrophosphate", Science, vol. 281, No. 5375, Jul. 1998, pp. 363-365.
Rothberg et al., "An integrated semiconductor device enabling non-optical genome sequencing", Nature, vol. 475, No. 7356, Jul. 21, 2011, pp. 348-352.
Rowe et al., "An Array Immunosensor for Simultaneous Detection of Clinical Analytes", Analytical Chemistry, vol. 71, No. 2, 1999, pp. 433-439.
Sakata et al, "DNA Sequencing Using Genetic Field Effect Transistor", 13th International Conference on Solid-State sensors, Actuators and Microsystems, vol. 2, Jun. 5-9, 2005, Seoul, Korea, pp. 1676-1679.
Sakata et al., "Cell-based field effect devices for cell adhesion analysis", Intl. Conf. on Microtechnologies in Medicine and Biology, May 9-12, 2006, Okinawa, Japan, 2006, pp. 177-179.
Sakata et al., "Detection of DNA recognition events using multi-well field effect transistor", Biosensors & Bioelectronics, vol. 21, 2005, pp. 827-832.
Sakata et al., "Detection sensitivity of genetic field effect transistor combined with charged nanoparticle-DNA conjugate", Intl. Conf. on Microtechnologies in Medicine and Biology, May 9-12, 2005, Okinawa, Japan, 2006, pp. 97-100.
Sakata et al., "Direct detection of single nucleotide polymorphism using genetic field effect transistor", International Microprocesses and Nanotechnology Conference. Oct. 26-29, 2004. Osaka, Japan. Digest of Papers Microprocesses and Nanotechnology 2004. pp. 226-227.
Sakata et al., "Direct Detection of Single-Base Extension Reaction Using Genetic Field Effect Transistor", Proc. of 3rd Ann. Intl. IEEE EMBS Special Topic Conf. on Microtechnologies in Medicine and Biology, Kahuku, Oahu, HI, May 12-15, 2005, pp. 219-222.
Sakata et al., "Direct transduction of allele-specific primer extension into electrical signal using genetic field effect transistor", Biosensors & Bioelectronics, vol. 22, 2007, pp. 1311-1316.

(56) References Cited

OTHER PUBLICATIONS

Sakata et al., "DNA Analysis Chip Based on Field-Effect Transistors", Japanese Journal of Applied Physics, vol. 44, No. 4B, 2005, pp. 2854-2859.
Sakata et al., "DNA Sequencing Based on Intrinsic Molecular Charges", Angewandte Chemie International, vol. 118, 2006, pp. 2283-2286.
Sakata et al., "DNA Sequencing Based on Intrinsic Molecular Charges", Angewandte Chemie International, vol. 45, No. 14, Mar. 27, 2006, pp. 2225-2228.
Sakata et al., "Immobilization of oligonucleotide probes on Si3N4 surface and its application to genetic field effect transistor", Materials Science and Engineering: C, vol. 24, Nos. 6-8, Dec. 2004, pp. 827-832.
Sakata et al., "Potential Behavior of Biochemically Modified Gold Electrode for Extended-Gate Field-Effect Transistor", Japanese Journal of Applied Physics, vol. 44, Part 1, No. 4S, Apr. 2005, pp. 2860-2863.
Sakata et al., "Potential response of genetic field effect transistor to charged nanoparticle-DNA conjugate", International Microprocesses and Nanotechnology Conference. Oct. 25-28, 2005. Tokyo, Japan. Digest of Papers Microprocesses and Nanotechnology 2005. pp. 42-43.
Sakata et al., "Potentiometric Detection of Allele Specific Oligonucleotide Hybridization Using Genetic Field Effect Transistor", Micro Total Analysis Systems, vol. 1,8th Intl. Conf. on Miniaturized Systems for Chemistry and Life Sciences, Sep. 26-30, 2004, Malmo, Sweden, pp. 300-302.
Sakata et al., "Potentiometric Detection of DNA Molecules Hybridization Using Gene Field Effect Transistor and Intercalator", Materials Research Society Symposium Proceedings, vol. 782, Micro- and Nanosystems, Boston, Massachusetts, Jan. 2003, pp. 393-398.
Sakata et al., "Potentiometric Detection of DNA Using Genetic Transistor", Denki Gakkai Kenkyukai Shiryo Chemical Sensor Kenkyukai, CHS-03-51-55, 2003, pp. 1-5.
Sakata et al., "Potentiometric Detection of Single Nucleotide Polymorphism by Using a Genetic Field-effect transistor", ChemBioChem, vol. 6, No. 4, Apr. 2005, pp. 703-710.
Sakurai et al., "Real-Time Monitoring of DNA Polymerase Reactions by a Micro ISFET pH Sensor", Analytical Chemistry, vol. 64, No. 17, Sep. 1992, pp. 1996-1997.
Salama, "CMOS luminescence detection lab-on-chip: modeling, design, and characterization", Thesis, Presented at Stanford University, 2005, pp. ii-78.
Salama, "Modeling and simulation of luminescence detection platforms", Biosensors & Bioelectronics, vol. 19, No. 11, Jun. 15, 2004, pp. 1377-1386.
Sawada et al., "A novel fused sensor for photo- and ion-sensing", Sensors and Actuators B: Chemical, vol. 106, No. 2, May 2005, pp. 614-618.
Sawada et al., "Highly sensitive ion sensors using charge transfer technique", Sensors and Actuators B: Chemical, vol. 98, No. 1, Mar. 2004, pp. 69-72.
Schasfoort et al., "A new approach to immunoFET operation", Biosensors & Bioelectronics, vol. 5, No. 2, 1990, pp. 103-124.
Schasfoort et al., "Field-effect flow control for microfabricated fluidic networks", Science, vol. 286. No. 5441, Oct. 29, 1999, pp. 942-945.
Schoning et al., "Bio FEDs (Field-Effect Devices): State-of-thert and New Directions", Electroanalysis, vol. 18, Nos. 19-20, Sep. 2006, pp. 1893-1900.
Schoning et al., "Recent advances in biologically sensitive field-effect transistors (BioFETs)", Analyst, vol. 127, No. 9, 2002, pp. 1137-1151.
Schroder, "6. Oxide and Interface Trapped Charges, Oxide Thickness", Semiconductor Material and Device Characterization, John Wiley & Sons, ISBN: 978-0-471-73906-7, Feb. 2006, pp. 319-387.
Seong-Jin et al. "Label-Free CMOS DNA Quantification With On-Chip Noise Reduction Schemes" Solid-State Sensors, Actuators and Microsystems Conference, IEEE, Jun. 10, 2013, pp. 947-950.
SG200903992-6, Search and Examination Report, dated Jan. 20, 2011, pp. 12.
Shah, "Microfabrication of a parellelrray DNA pyrosequencing chip", NNIN REU Research Accomplishments, 2005, pp. 130-131.
Shepherd et al., "A biochemical translinear principle with weak inversion ISFETs", IEEE Trans Circuits Syst-I, vol. 52, No. 12, Dec. 2005, pp. 2614-2619.
Shepherd et al., "A novel voltage-clamped CMOS ISFET sensor interface", IEEE, 2007, pp. 3331-3334.
Shepherd et al., "Towards direct biochemical analysis with weak inversion ISFETS", Intl Workshop on Biomedical, 2004, pp. 51.5-5-51.5-8.
Shepherd et al., "Weak inversion ISFETs for ultra-low power biochemical sensing and real-time analysis", Sensors Actuators B, vol. 107, 2005, pp. 468-473.
Shi et al., "Radical Capillary Array Electrophoresis Microplace and Scanner for High-Performance Nucleic Acid Analysis", Analytical Chemistry, vol. 71, No. 23, 1999, pp. 5354-5361.
Sia, et al., "Microfluidic devices fabricated in poly(dimethylsiloxane) for biological studies", Electrophoresis, vol. 24, 2003, pp. 3563-3576.
Sibbald et al., "A miniature flowthrough cell with a four-function ChemFET integrated circuit for simultaneous measurements of potassium, hydrogen, calcium and sodium ions", Analytica chimica acta., 159, 1984, pp. 47-62.
Simonian et al., "FET based biosensors for the direct detection of organophosphate neurotoxins", Electroanalysis, vol. 16, No. 22, 2004, pp. 1896-1906.
Souteyrand et al., "Direct detection of the hybridization of synthetic homo-oligomer DNA sequences by field effect", Journal of Physical Chemistry B, vol. 101, No. 15, 1997, pp. 2980-2985.
Starodub et al., "Immunosensor for the determination of the herbicide simazine based on an ion-selective field-effect transistor", Analytica Chimica Acta, vol. 424, No. 1, Nov. 2000, pp. 37-43.
Takenaka et al., "DNA Sensing on a DNA Probe-Modified Electrode Using Ferrocenylnaphthalene Dimide as the Electrochemically Active Ligand", Analytical Chemistry, vol. 72. No. 6, 2000, pp. 1334-1341.
Temes et al., "A Tutorial Discussion of the Oversampling Method for A/D and D/A Conversion", IEEE International Symposium on Circuits and Systems, vols. 2 of 4, 1990, 5 pages.
Thewes et al., "CMOS-based Biosensor Arrays", Proceedings of the Design, Automation and Test in Europe Conference and Exhibition, 2005, 2 pages.
Tokuda et al., "A CMOS image sensor with optical and potential dual imaging function for on-chip bioscientific applications", Sensors and Actuators A: Physical, vol. 125, No. 2, Jan. 2006, pp. 273-280.
Tomaszewski et al., "Electrical characterization of ISFETs", Journal of Telecommunications and Information Technology, Mar. 2007, pp. 55-60.
Toumazou et al., "Using transistors to linearise biochemistry," Electronics Letters, vol. 43, No. 2, Jan. 18, 2007, 3 pages.
Truman et al. "Monitoring liquid transport and chemical composition in lab on a chip systems using ion sensitive FET devices", Lab on a Chip, vol. 6, No. 9, Jul. 2006, pp. 1220-1228.
Unger et al., "Monolithic Microfabricated Valves and Pumps by Multilayer Soft Lithography", Science, vol. 288, No. 5463, Apr. 2000, pp. 113-116.
Unknown, "ISFET Wikipedia article", Wikipedia, Last modified Nov. 7, 2006.
Unknown, "OV5640 Datasheet Product Specification", 1/4" color CMOS QSXGA (5 megapixel) image sensor with OmniBSI technology. May 1, 2011, p. 1, line 9 and pp. 2-7, paragraph 1.
Uslu et al., "Labelfree fully electronic nucleic acid detection system based on a field-effect transistor device", Biosensors and Bioelectronics, vol. 19. No. 12, Jul. 2004, pp. 1723-1731.
Van Der Schoot et al., "The Use of a Multi-ISFET Sensor Fabricated in a Single Substrate", Sensors and Actuators, vol. 12, No. 4, Nov.-Dec. 1987, pp. 463-468. 0.
Van Der Wouden et al., "Directional flow induced by synchronized longitudinal and zeta-potential controlling AC-electrical fields", Lab Chip, vol. 6, No. 10, Oct. 2006, pp. 1300-1305.

(56) References Cited

OTHER PUBLICATIONS

Van Hal et al., "A general model to describe the electrostatic potential at electrolyte oxide interfaces", Advances in Colloid and Interface Science, vol. 69, Nos. 1-3, Dec. 1996, pp. 31-62.
Van Kerkhof et al., "ISFET Responses on a stepwise change in electrolyte concentration at constant pH", Sensors Actuators B: Chemical, vol. 18-19, Mar. 1994, pp. 56-59.
Van Kerkhof et al., "The development of an ISFET-based heparin sensor," Thesis 1994. Published Aug. 10, 1965.
Van Kerkhof et al., "The ISFET based heparin sensor with a monolayer of protamine as affinity ligand", Biosensors & Bioelectronics, vol. 10, Nos. 3-4, 1995, pp. 269-282.
Van Kerkhof, "Development of an ISFET based heparin sensor using the ion-step measuring method", Biosensors & Bioelectronics, vol. 8, Nos. 9-10, 1993, pp. 463-472.
Vardalas, "Twists and Turns in the Development of the Transistor", IEEE-USA Today's Engineer Online, May 2003, 6 pages.
Voigt et al., "Diamond-like carbon-gate pH-ISFET", Sensors and Actuators B: Chemical, vol. 44, Nos. 1-3, Oct. 1997, pp. 441-445.
Wagner et al., "All-in-one solid-state device based on a lightddressable potentiometric sensor platform", Sensors and Actuators B: Chemical, vol. 117, No. 2, Oct. 2006, pp. 472-479.
Wang et al., "Label-free detection of small-molecule-protein interactions by using nanowire nanosensors", Proceedings of the National Academy of Sciences, vol. 102, No. 9, Mar. 2005, pp. 3208-3212.
Wilhelm et al., "pH Sensor Based on Differential Measurements on One pH-FET Chip", Sensors and Actuators B: Chemical, vol. 4, Nos. 1-2, May 1991, pp. 145-149.
Woias et al., "Slow pH response effects of silicon nitride ISFET sensors", Sensors and Actuators B: Chemical, vol. 48, Nos. 1-3, May 1998, pp. 501-504.
Woias, "Modelling the short time response of ISFET sensors", Sensors and Actuators B: Chemical, vol. 24, Nos. 1-3, Mar. 1995, pp. 211-217.
Wood et al., "Base composition-independent hybridization in tetramethylammonium chloride: a method for oligonucleotide screening of highly complex gene libraries", Proceedings of the National Academy of Sciences, vol. 82, No. 6, Mar. 1985, pp. 1585-1588.
Wu et al., "DNA and protein microarray printing on silicon nitride waveguide surfaces", Biosensensors & Bioelectronics, vol. 21, No. 7, Jan. 2006, pp. 1252-1263.
Xu et al., "Analytical Aspects of FET-Based Biosensors", Frontiers in Bioscience, vol. 10, Jan. 2005, pp. 420-430.
Yeow et al., "A very large integrated pH-ISFET sensor array chip compatible with standard CMOS processes", Sensor and Actuators B: Chemical, vol. 44, Nos. 1-3, Oct. 1997, pp. 434-440.
Yoshida et al., "Development of a Wide Range pH Sensor based on Electrolyte-Insulator-Semiconductor Structure with Corrosion-Resistant Al2O3—Ta2O5 and Al2O3—ZrO2", Journal of the Electrochemical Society, vol. 151, No. 3, 2004, pp. H53-H58.
Yuqing et al., "Ion sensitive field effect transducer-based biosensors", Biotechnology Advances, vol. 21, No. 6, Sep. 2003, pp. 527-534.
Zhang et al., "32-Channel Full Customized CMOS Biosensor Chip for Extracellular neural Signal Recording", Proc. of the 2nd Intl. IEEE EMBs Conf. on Neural Engineering, Arlington, Virginia, Mar. 16-19, 2005, pp. v-viii.
Zhao et al., "Floating-Gate Ion Sensitive Field-Effect Transistor for Chemical and Biological Sensing", MRS Proceedings, vol. 828, 2005, pp. 349-354.
Zhou et al., "Quantitative detection of single nucleotide polymorphisms for a pooled sample by a bioluminometric assay coupled with modified primer extension reactions (BAMPER)", Nucleic Acids Research, vol. 29, No. 19, Oct. 2001, (e93), 1-11.
Cohen A, et al., "Depletion type floating gate p-channel MOS transistor for recording action potentials generated by cultured neurons", Biosensors and Bioelectronics, 2004, vol. 19, No. 12, pp. 1703-1709.
Jakobson C G et al., "Capacitance-voltage characteristics of floating gate electrolyte-insulator-semiconductor capacitors", IEEE, 2000, pp. 61-64.
EP Extended Search Report dated Nov. 27, 2020 for EP Application No. 09 822 323.3.
EP Extended Search Report dated Dec. 7, 2020 for EP Application No. 10 780 930.3.
JP Office action dated May 27, 2021, for JP Patent Application No. 2020-97451.

* cited by examiner

154

162
159,156,158

159
156,158

166
164

332
334
336
338
340
330

322
324
326
328
118₁

318
320

316
112₁
114₁
118₁

312

308

306

304

INTEGRATED SENSOR ARRAYS FOR BIOLOGICAL AND CHEMICAL ANALYSIS

RELATED APPLICATIONS

This application is a continuation of U.S. application Ser. No. 14/862,930 filed Sep. 23, 2015. U.S. application Ser. No. 14/862,930 is a continuation of U.S. application Ser. No. 14/599,948 filed Jan. 19, 2015. U.S. application Ser. No. 14/599,948 is a continuation of U.S. application Ser. No. 13/125,133 filed Jul. 1, 2011, which issued as U.S. Pat. No. 8,936,763 on Jan. 20, 2015. U.S. Pat. No. 8,936,763 is a 371 filing of International Application No. PCT/US2009/005745 filed Oct. 22, 2009. PCT/US2009/005745 claims priority to U.S. application Ser. No. 12/475,311 and to U.S. application Ser. No. 12/474,897; both filed on May 29, 2009. U.S. Ser. No. 12/474,897 claims the benefit of U.S. Provisional Application Nos. 61/196,953 filed Oct. 22, 2008, 61/198,222 filed Nov. 4, 2008, and 61/205,626 filed Jan. 22, 2009. All applications listed in this section are incorporated by reference herein, each in their entirety.

FIELD OF THE DISCLOSURE

The present disclosure is directed generally to semiconductor chips for making chemical measurements, and more particularly, to single chip ISFET arrays (and arrays of single chip ISFET arrays) for monitoring one or more analytes.

BACKGROUND

Rapid and accurate measurement of biological and chemical analytes is important in many fields, ranging from diagnostics, to industrial process control, to environmental monitoring, to scientific research. Chemically sensitive, and in particular, ion-sensitive field effect transistors ("chemFETs" and "ISFETs" respectively) have been used for such measurements for many years, e.g. Bergveld, Sensors and Actuators, 88: 1-20 (2003); Yuqing et al., Biotechnology Advances, 21: 527-534 (2003); and the like. More recently, attempts have been made to fabricate arrays of such sensors using integrated circuit technologies to obtain spatially distributed and multi-analyte measurements using a single device, e.g., Yeow et al., Sensors and Actuators B 44: 434-440 (1997); Martinoia et al., Biosensors & Bioelectronics, 16: 1043-1050 (2001); Milgrew et al., Sensors and Actuators B 103: 37-42 (2004); Milgrew et al., Sensors and Actuators B, 111-112: 347-353 (2005); Hizawa et al., Sensors and Actuators B, 117: 509-515 (2006); Heer et al., Biosensors and Bioelectronics, 22: 2546-2553 (2007); and the like. Such efforts face several difficult technical challenges, particularly when ISFET sensor arrays have scales in excess of thousands of sensor elements and densities in excess of many hundreds of sensor elements per $mm^2$ Such challenges include making large-scale arrays with sensor elements having uniform performance characteristics from sensor to sensor within the array, and making sensor elements with footprints on the order of microns which are capable of generating signals detectable against a background of many noise sources from both the sensor array itself and a fluidics system that conveys reactants or analyte-containing samples to the array, For ISFET arrays comprising sensor elements with charge-sensitive components, such as floating gates, the former challenge is exacerbated by the accumulation of trapped charge in or adjacent to such components, which is a common side product of semiconductor fabrication technologies. The latter challenge is exacerbated by the requirement that analytes of interest directly or indirectly generate a charged species that accumulates at or on a charge-sensitive component of the ISFET sensor. In very dense arrays, diffusion, reactivity of the analyte or its surrogate, cross-contamination from adjacent sensors, as well as electrical noise in the sample fluid can all adversely affect measurements. The availability of large-scale ISFET array that overcome these challenges would be highly useful in the above fields, particularly where ever highly parallel multiplex chemical measurements are required, such as in the large scale genetic analysis of genomes.

SUMMARY

Aspects of the invention relate in part to large arrays of chemFETs or more specifically ISFETs for monitoring reactions, including for example nucleic acid (e.g., DNA) sequencing reactions, based on monitoring analytes present, generated or used during a reaction. More generally, arrays including large arrays of chemFETs may be employed to detect and measure static and/or dynamic amounts or concentrations of a variety of analytes (e.g., hydrogen ions, other ions, non-ionic molecules or compounds, etc.) in a variety of chemical and/or biological processes (e.g., biological or chemical reactions, cell or tissue cultures or monitoring, neural activity, nucleic acid sequencing, etc.) in which valuable information may be obtained based on such analyte measurements. Such arrays may be employed in methods that detect analytes and/or methods that monitor biological or chemical processes via changes in charge at the surfaces of sensors in the arrays, either by direct accumulation of charged products or by indirect generation or capture of charged species related to the concentration or presence of an analyte of interest. The present invention is exemplified in a number of implementations and applications, some of which are summarized below.

In one aspect the invention is directed to an apparatus comprising a chemical field effect transistor array in a circuit-supporting substrate, such transistor array having disposed on its surface an array of sample-retaining regions capable of retaining a chemical or biological sample from a sample fluid, wherein such transistor array has a pitch of 10 μm or less and each sample retaining region is positioned on at least one chemical field effect transistor which is configured to generate at least one output signal related to a characteristic of a chemical or biological sample in such sample-retaining region. In one embodiment, the characteristic of said chemical or biological sample is a concentration or an amount of a charged species and wherein each of said chemical field effect transistors is an ion-sensitive field effect transistor having a floating gate with a dielectric layer on a surface thereof, the dielectric layer contacting said sample fluid and being capable of accumulating charge in proportion to a concentration of the charged species in said sample fluid. In one embodiment, such charged species is a hydrogen ion such that the sensors measure changes in pH of the sample fluid in or adjacent to the sample-retaining region thereof. In an aspect of such embodiment, the dielectric layer has a thickness selected to maximize capacitance thereacross, consistent with other requirements. Such thickness may be selected in the range of from 1 to 1000 nanometers (nm), or in a range of from 10 to 500 nm, or in a range of from 20 to 100 nm.

In another aspect, the invention is directed to an integrated sensor array that comprises a plurality of sensors formed in a circuit-supporting substrate, each sensor comprising a chemical field effect transistor, the sensors being in a planar array of greater than 256 sensors at a density greater than 100 sensors per $mm^2$, each sensor of the array being configured to provide at least one output signal related to a concentration or presence of a chemical or biological sample proximate thereto, such output signal being substantially the same for each sensor of the array in response to the same concentration or presence of the same chemical or biological sample. In one embodiment of this aspect, the integrated sensor array further includes a plurality of sample-retaining regions in said circuit-supporting substrate, each sample-retaining region on (or alternatively below or beside) and operationally associated with at least one of said sensors. In another embodiment, such sample retaining regions are each microwells configured to hold a sample within a volume of sample fluid. In another embodiment, sensors of the integrated sensor array detect or measure a concentration of a charged species and each of the sensors is an ion-sensitive field effect transistor having a floating gate with a dielectric layer on a surface thereof, the dielectric layer contacting a sample fluid containing said chemical or biological sample and being capable of accumulating charge in proportion to a concentration of the charged species in the sample fluid adjacent thereto. The dielectric layer has a thickness selected to maximize capacitance thereacross, consistent with other requirements.

In a further aspect, the invention is directed to a single chip chemical assay device that comprises: (a) a sensor array formed in a circuit supporting substrate, each sensor of the array comprising a chemical field-effect transistor and being configured to provide at least one output signal related to a concentration or presence of a chemical or biological sample proximate thereto, such output signal being substantially the same for each sensor of the array in response to the same concentration or presence of the same chemical or biological sample; (b) a plurality of sample retaining regions in the circuit supporting substrate, each sample-retaining region disposed on at least one sensors; and (c) control circuitry in the circuit supporting substrate coupled to the sensor array to receive samples of the output signals from said chemical field effect transistors at a rate of at least one frame per second.

In still another aspect the invention is directed to a single chip nucleic acid assay device that comprises: (a) a sensor array formed in a circuit supporting substrate, each sensor of the array comprising a chemical field-effect transistor and being configured to provide at least one output signal related to a concentration or presence of a chemical or biological sample proximate thereto, such output signal being substantially the same for each sensor of the array in response to the same concentration or presence of the same chemical or biological sample; (b) a plurality of sample retaining regions in the circuit supporting substrate, each sample-retaining region disposed on at least one sensors; (c) supports, including solid supports such as particulate solid supports, disposed on the sample-retaining regions, each support having a concatemerized template attached thereto; and (d) control circuitry in the circuit supporting substrate coupled to the sensor array to receive samples of the output signals from said chemical field effect transistors at a rate of at least one frame per second. Supports may include beads, including beads having solid or porous cores and/or solid or porous surfaces, microspheres, microparticles, gel microdroplets and other separable particulate supports for attaching DNA templates, particularly as clonal populations. Such supports may be on the order of microns or nanometers, depending on the application. For example, the beads may be microbeads or they may be nanobeads.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the present invention.

BRIEF DESCRIPTION OF THE DRAWINGS

In the drawings, like reference characters generally refer to the same parts throughout the different views. Also, the drawings are not necessarily to scale, emphasis instead being placed upon generally illustrating the various concepts discussed herein.

DETAILED DESCRIPTION

Figure 1:
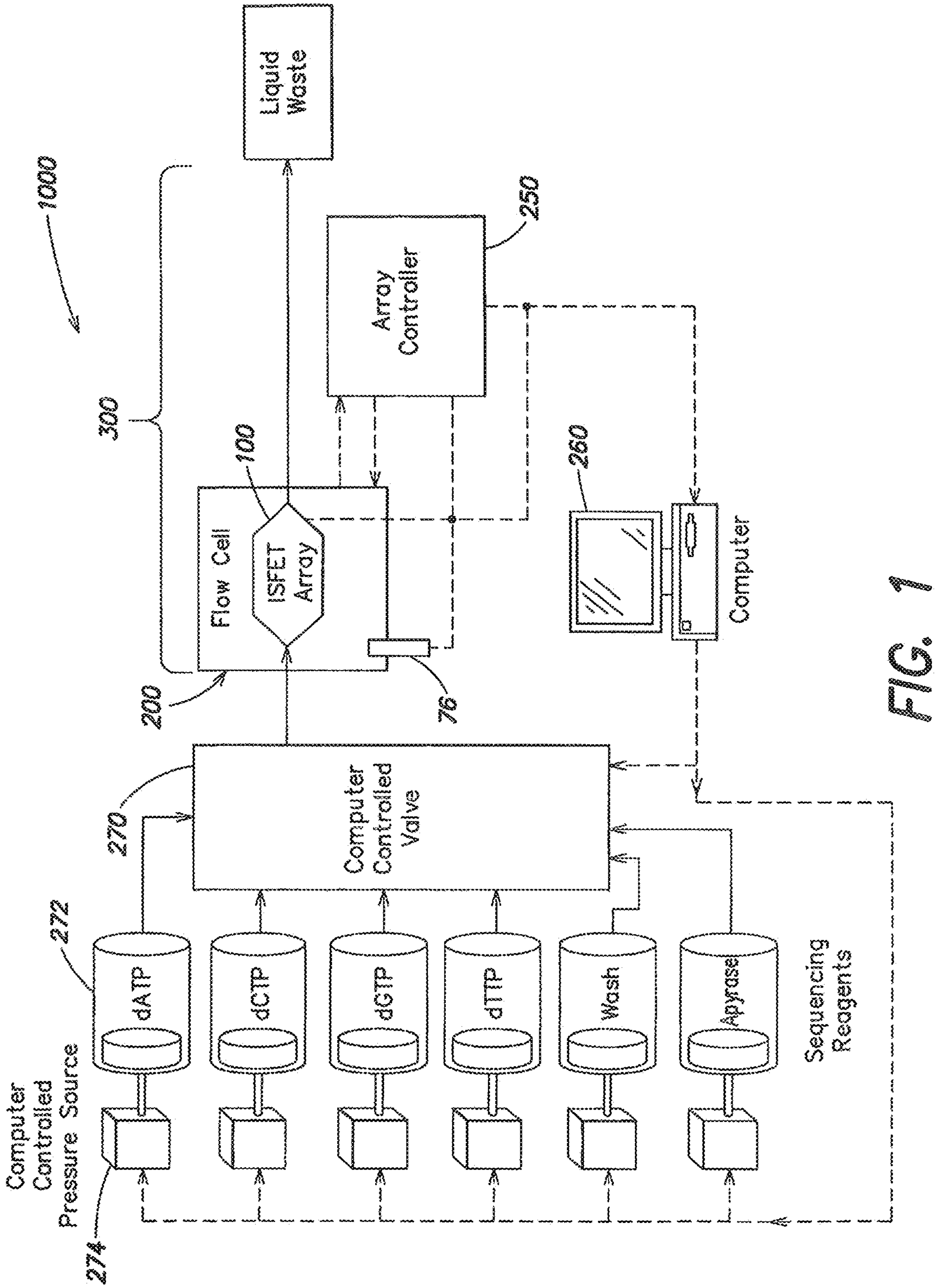
FIG. 1 generally illustrates a nucleic acid processing system comprising a large scale chemFET array, according to one inventive embodiment of the present disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention. For example, the microelectronics portion of the apparatus and array is implemented in CMOS technology for purposes of illustration. It should be appreciated, however, that the disclosure is not intended to be limiting in this respect, as other semiconductor-based technologies may be utilized to implement various aspects of the microelectronics portion of the systems discussed herein. Guidance for making arrays of the invention is found in many available references and treatises on integrated circuit design and manufacturing and micromachining, including, but not limited to, Allen et al., CMOS Analog Circuit Design (Oxford University Press, 2"d Edition, 2002); Levinson, Principles of Lithography, Second Edition (SPIE Press, 2005); Doering and Nishi, Editors, Handbook of Semiconductor Manufacturing Technology, Second Edition (CRC Press, 2007); Baker, CMOS Circuit Design, Layout, and Simulation (IEEE Press, Wiley-Interscience, 2008); Veendrick, Deep-Submicron CMOS ICs (Kluwer-Deventer, 1998); Cao, Nanostructures & Nanomaterials (Imperial College Press, 2004); and the like, which relevant parts are hereby incorporated by reference.

In one aspect the invention is directed to integrated sensor arrays (e.g., a two-dimensional array) of chemically-sensitive field effect transistors (chemFETs), where the individual chemFET sensor elements or "pixels" of the array are configured to detect analyte presence (or absence), analyte levels (or amounts), and/or analyte concentration in a sample fluid. "Sample fluid" means a fluid which is used to deliver sample or reagents to a sample-retaining region or to remove products or reactants from sample-retaining regions, such as a wash fluid of a multi-step reaction. Sample fluids may remain the same or may change in the course of an analytical process, or processes, taking place on an array. Analytical processes detected or monitored by arrays of the invention include chemical and/or biological processes (e.g., chemical reactions, cell cultures, neural activity, nucleic acid sequencing reactions, etc.) occurring in proximity to the array. Examples of chemFETs contemplated by various embodiments discussed in greater detail below include, but are not limited to, ion-sensitive field effect transistors (ISFETs) and enzyme-sensitive field effect transistors (EnFETs). In one exemplary implementation, one or more microfluidic structures is/are fabricated above the chemFET sensor array to provide for retention, containment and/or confinement of a biological or chemical reaction in which an analyte of interest may be captured, produced, or consumed, as the case may be. Such structures define regions on an array referred to herein as "sample-retaining regions." For example, in one implementation, the microfluidic structure (s) may be configured as one or more wells (or microwells, or reaction chambers, or reaction wells as the terms are used interchangeably herein) disposed above one or more sensors of the array, such that the one or more sensors over which a given well is disposed detect and measure analyte presence, level, and/or concentration in the given well. Preferably, there is a 1:1 ratio of wells and sensors.

A chemFET array according to various inventive embodiments of the present disclosure may be configured for sensitivity to any one or more of a variety of analytes. In one embodiment, one or more chemFETs of an array may be particularly configured for sensitivity to one or more analytes, and in other embodiments different chemFETs of a given array may be configured for sensitivity to different analytes. For example, in one embodiment, one or more sensors (pixels) of the array may include a first type of chemFET configured to be sensitive to a first analyte, and one or more other sensors of the array may include a second type of chemFET configured to be sensitive to a second analyte different from the first analyte. In one embodiment, the first and second analytes may be related to each other. As an example, the first and second analytes may be byproducts of the same biological or chemical reaction/process and therefore they may be detected concurrently to confirm the occurrence of a reaction (or lack thereof). Such redundancy is preferable in some analyte detection methods. Of course, it should be appreciated that more than two different types of chemFETs may be employed in any given array to detect and/or measure different types of analytes, and optionally to monitor biological or chemical processes such as binding events. In general, it should be appreciated in any of the embodiments of sensor arrays discussed herein that a given sensor array may be "homogeneous" and thereby consist of chemFETs of substantially similar or identical type that detect and/or measure the same analyte (e.g., pH or other ion concentration), or a sensor array may be "heterogeneous" and include chemFETs of different types to detect and/or measure different analytes. In another embodiment, the sensors in an array may be configured to detect and/or measure a single type (or class) of analyte even though the species of that type (or class) detected and/or measured may be different between sensors. As an example, all the sensors in an array may be configured to detect and/or measure nucleic acids, but each sensor detects and/or measures a different nucleic acid.

As used herein, an array is a planar arrangement of elements such as sensors or wells. The array may be one or two dimensional. A one dimensional array is an array having one column (or row) of elements in the first dimension and a plurality of columns (or rows) in the second dimension. An example of a one dimensional array is a 1×5 array. A two dimensional array is an array having a plurality of columns (or rows) in both the first and the second dimensions. The number of columns (or rows) in the first and second dimensions may or may not be the same. An example of a two dimensional array is a 5×10 array.

Accordingly, one embodiment is directed to an apparatus, comprising an array of CMOS-fabricated sensors, each sensor comprising one chemically-sensitive field effect transistor (chemFET) and occupying an area on a surface of the array of 10 $\mu m^2$ or less, 9 $\mu m^2$ or less, 8 $\mu m^2$ or less, 7 $\mu m^2$ or less, 6 $\mu m^2$ or less, 5 $\mu m^2$ or less, 4 $\mu m^2$ or less 3 $\mu m^2$ or less, or 2 $\mu m^2$ or less. Another embodiment of the invention is directed to an apparatus comprising a planar array of CMOS-fabricated sensors in a density of at least 100 sensors/$mm^2$, or at least 250 sensors/$mm^2$, or at least 1000 sensors/$mm^2$, or at least 5000 sensors/$mm^2$, or at least 10000 sensors/$mm^2$.

Another embodiment is directed to an apparatus, comprising an array of CMOS fabricated sensors, each sensor comprising one chemically-sensitive field effect transistor (chemFET). The array of CMOS-fabricated sensors includes more than 256 sensors, and a collection of chemFET output signals from all chemFETs of the array constitutes a frame of data. The apparatus further comprises control circuitry coupled to the array and configured to generate at least one array output signal to provide multiple frames of data from the array at a frame rate of at least 1 frame per second. In one aspect, the frame rate may be at least 10 frames per second. In another aspect, the frame rate may be at least 20 frames per second. In yet other aspects, the frame rate may be at least 30, 40, 50, 70 or up to 100 frames per second. Chemical or biological phenomena measured by the sensors may result in electrical signals, usually current or voltage level changes, having a wide variety of durations and amplitudes. In some embodiments, such signals may have a duration in the range of a few milliseconds, e.g. 10 msec, to many seconds, e.g. 10-20 sec. For cyclical or sequential processes monitored by arrays, such signals may be substantially repeated over an interval of minute, hours, or days. Moreover, the signal may have superimposed various types of noise, including flicker noise from the array itself, and thermal noise, particularly from the sample fluid. The control circuitry of the apparatus is configured to sample each signal from each sensor in the array for a complete frame of data. Such sampling may be for a short duration, e.g. 1-100 μsec, or the like, so that complete frames of data may be readout in the frame per second values listed above.

As explained more fully below, arrays of the invention have been fabricated in a manner that reduces the effects of trapped charge, which includes lack of stability and uniformity of sensor-to-sensor responses to the same or similar sensing conditions by sensor in the same array. In one embodiment, such responses may be measured by exposing sensors of an array to predefined changes in pH. In one embodiment, responses of at least 95 percent of the sensors in an array are substantially linear over a range of from 7 to 9 pH and has a voltage output signal with a sensitivity of at least 40 m V/pH unit. In another embodiment, at least 98 percent of sensor of an array have such performance. "Substantially linear" means that measured pH values over such pH range has a coefficient of variation of deviation from linearity of at least 10 percent, or at least 5 percent, or at least 2 percent. In another embodiment, at least 95 percent of sensors of such arrays each have a response time to a change of pH of less than 200 msec.

Another embodiment is directed to a sensor array, comprising a plurality of electronic sensors arranged in a plurality of rows and a plurality of columns. Each sensor comprises one chemically-sensitive field effect transistor (chemFET) configured to provide at least one and in some instances at least two output signals representing a presence and/or a concentration of an analyte proximate to a surface of the array. For each column of the plurality of columns, the array further comprises column circuitry configured to provide a constant drain current and a constant drain-to-source voltage to respective chemFETs in the column, the column circuitry including two operational amplifiers and a diode-connected FET arranged in a Kelvin bridge configuration with the respective chemFETs to provide the constant drain-to-source voltage.

Another embodiment is directed to a sensor array, comprising a plurality of electronic sensors arranged in a plurality of rows and a plurality of columns. Each sensor comprises one chemically-sensitive field effect transistor (chemFET) configured to provide at least one output signal and in some instances at least two output signals representing a concentration of ions in a solution proximate to a surface of the array. The array further comprises at least one row select shift register to enable respective rows of the plurality of rows, and at least one column select shift register to acquire chemFET output signals from respective columns of the plurality of columns.

The apparatus and devices of the invention can be used to detect and/or monitor interactions between various entities. These interactions include biological and chemical reactions and may involve enzymatic reactions and/or non-enzymatic interactions such as but not limited to binding events. As an example, the invention contemplates monitoring enzymatic reactions in which substrates and/or reagents are consumed and/or reaction intermediates, byproducts and/or products are generated. An example of a reaction that can be monitored according to the invention is a nucleic acid synthesis method such as one that provides information regarding nucleic acid sequence. This reaction will be discussed in greater detail herein.

Apparatus

Apparatus of the invention can vary widely depending on the analyte being detected, whether assay reactions with auxiliary reagents are required, and whether sequential or cyclical reactions are required. In one aspect, apparatus of the invention comprises a sensor array and an array of sample-retaining regions on a surface thereof for retaining biological or chemical analytes delivered to the surface by a sample fluid. In one embodiment, sample-retaining regions are integral with the sensor array and may have a wide variety of formats. Such regions may be defined by chemically reactive group on the surface of the sensor array, by binding compounds attached to the surface of the sensor array which are specific for predetermined analytes, by regions of hydrophobicity or hydrophilicity, or by spatial features such as microwells, cavities, weirs, dams, reservoirs, or the like. In additional embodiments, apparatus of the invention may comprise sample carriers, such as beads, particles, gel microdroplets, or other supports, structures or substances which hold analytes of interest and which may be delivered to sample-retaining regions by a sample fluid. Such sample carriers may include binding moieties or reactive groups to permit attachment to sample-retaining regions. Such attachment may be specific wherein such binding moieties or reactive groups form linkages with only complementary binding compounds or functionalities, or the attachment may be random where a sample carrier has a substantially equal likelihood of being retained in any sample-retaining region of an array. As described more fully below, in one embodiment, sample-retaining regions are arrays of microwells that each have walls and an interior for physically retaining sample, analyte and/or one or more sample carriers.

As is exemplified below, sample fluid and samples or analytes may be delivered to retaining regions of a sensor array in several ways. Where sensor arrays are employed as one-use sample characterization devices, such as with process, environmental or cellular monitoring, sample may be delivered by emersion, pipetting, pouring, or by other direct methods. Where sensor arrays are employed in sequential or cyclical reactions, such as in DNA sequencing, sample fluidic, including nucleic acid templates, reagents, wash solutions, and the like, may be delivered by a fluidic system under computer control. For such latter applications, embodiments of the invention may further include a flow cell integrated with the sample-retaining regions and sensor array. As described more fully below, in one embodiment, such flow cell delivers sample fluids (including assay reactants, buffers, and the like) to sample-retaining regions under controlled conditions, which may include laminar flow, constant flow rate at each sample-retaining region, controlled temperature, minimization of bubbles or other flow disruptions, and the like. In one aspect, a flow cell of an apparatus of the invention comprises an inlet, an outlet, and an interior space, which when the flow cell is in communication with, for example sealingly bonded to, the arrays of sample retaining regions and sensors forms a chamber that is closed except for the inlet and outlet. In some embodiments, the device is manufactured such that the flow cell and one or both the arrays are integral to each other. In other embodiments, the flow cell is sealingly bonded to the arrays. Either embodiment will prevent fluid leakage, which, among other possible hazards, would introduce electrical noise into the sample fluid. In one aspect, the apparatus of the invention includes a reference electrode in fluid contact with the sample fluid so that during operation an electrical potential difference is established between the reference electrode and the sensors of the array.

An exemplary apparatus is shown in FIG. 1 which is adapted for nucleic acid sequencing. In the discussion that follows, the chemFET sensors of the array are described for purposes of illustration as ISFETs configured for sensitivity to static and/or dynamic ion concentration, including but not limited to hydrogen ion concentration. However, it should be appreciated that the present disclosure is not limited in this respect, and that in any of the embodiments discussed herein in which ISFETs are employed as an illustrative example, other types of chemFETs may be similarly employed in alternative embodiments, as discussed in further detail below. Similarly it should be appreciated that various aspects and embodiments of the invention may employ ISFETs as sensors yet detect one or more ionic species that are not hydrogen ions.

The system 1000 includes a semiconductor/microfluidics hybrid structure 300 comprising an ISFET sensor array 100 and a microfluidics flow cell 200. In one aspect, the flow cell 200 may comprise a number of wells (not shown in FIG. 1) disposed above corresponding sensors of the ISFET array 100. In another aspect, the flow cell 200 is configured to facilitate the sequencing of one or more identical template nucleic acids disposed in the flow cell via the controlled and ordered introduction to the flow cell of a number of sequencing reagents 272 (e.g., dATP, dCTP, dGTP, dTTP (generically referred to herein as dNTP), divalent cations such as but not limited to $Mg^{2+}$, wash solutions, and the like).

As illustrated in FIG. 1, the introduction of the sequencing reagents to the flow cell 200 may be accomplished via one or more valves 270 and one or more pumps 274 that are controlled by a computer 260. A number of techniques may be used to admit (i.e., introduce) the various processing materials (i.e., solutions, samples, reaction reagents, wash solutions, and the like) into the wells of such a flow cell. As illustrated in FIG. 1, reagents including dNTP may be admitted to the flow cell (e.g., via the computer controlled valve 270 and pumps 274) from which they diffuse into the wells, or reagents may be added to the flow cell by other means such as an ink jet. In yet another example, the flow cell 200 may not contain any wells, and diffusion properties of the reagents may be exploited to limit cross-talk between respective sensors of the ISFET array 100, or nucleic acids may be immobilized on the surfaces of sensors of the ISFET array 100.

The flow cell 200 in the system of FIG. 1 may be configured in a variety of manners to provide one or more analytes (or one or more reaction solutions) in proximity to the ISFET array 100. For example, a template nucleic acid may be directly attached or applied in suitable proximity to one or more pixels of the sensor array 100, or in or on a support material (e.g., one or more "beads") located above the sensor array but within the reaction chambers, or on the sensor surface itself. Processing reagents (e.g., enzymes such as polymerases) can also be placed on the sensors directly, or on one or more solid supports (e.g., they may be bound to the capture beads or to other beads) in proximity to the sensors, or they may be in solution and free-flowing. It is to be understood that the device may be used without wells or beads.

In the system 1000 of FIG. 1, according to one embodiment the ISFET sensor array 100 monitors ionic species, and in particular, changes in the levels/amounts and/or concentration of ionic species, including hydrogen ions. In important embodiments, the species are those that result from a nucleic acid synthesis or sequencing reaction.

Via an array controller 250 (also under operation of the computer 260), the ISFET array may be controlled so as to acquire data (e.g., output signals of respective ISFETs of the array) relating to analyte detection and/or measurements, and collected data may be processed by the computer 260 to yield meaningful information associated with the processing (including sequencing) of the template nucleic acid.

With respect to the ISFET array 100 of the system 1000 shown in FIG. 1, in one embodiment the array 100 is implemented as an integrated circuit designed and fabricated using standard CMOS processes (e.g., 0.35 micrometer process, 0.18 micrometer process), comprising all the sensors and electronics needed to monitor/measure one or more analytes and/or reactions. With reference again to FIG. 1, one or more reference electrodes 76 to be employed in connection with the ISFET array 100 may be placed in the flow cell 200 (e.g., disposed in "unused" wells of the flow cell) or otherwise exposed to a reference (e.g., one or more of the sequencing reagents 172) to establish a baseline against which changes in analyte concentration proximate to respective ISFETs of the array 100 are compared. The reference electrode(s) 76 may be electrically coupled to the array 100, the array controller 250 or directly to the computer 260 to facilitate analyte measurements based on voltage signals obtained from the array 100; in some implementations, the reference electrode(s) may be coupled to an electric ground or other predetermined potential, or the reference electrode voltage may be measured with respect to ground, to establish an electric reference for ISFET output signal measurements, as discussed further below.

More generally, a chemFET array according to various embodiments of the present disclosure may be configured for sensitivity to any one or more of a variety of analytes. In one embodiment, one or more chemFETs of an array may be particularly configured for sensitivity to one or more analytes and/or one or more binding events, and in other embodiments different chemFETs of a given array may be configured for sensitivity to different analytes. For example, in one embodiment, one or more sensors (pixels) of the array may include a first type of chemFET configured to be sensitive to a first analyte, and one or more other sensors of the array may include a second type of chemFET configured to be sensitive to a second analyte different from the first analyte. In one exemplary implementation, both a first and a second analyte may indicate a particular reaction such as for example nucleotide incorporation in a sequencing-by-synthesis method. Of course, it should be appreciated that more than two different types of chemFETs may be employed in any given array to detect and/or measure different types of analytes and/or other reactions. In general, it should be appreciated in any of the embodiments of sensor arrays discussed herein that a given sensor array may be "homogeneous" and include chemFETs of substantially similar or identical types to detect and/or measure a same type of analyte (e.g., hydrogen ions), or a sensor array may be "heterogeneous" and include chemFETs of different types to detect and/or measure different analytes.

In other aspects of the system shown in FIG. 1, one or more array controllers 250 may be employed to operate the ISFET array 100 (e.g., selecting/enabling respective pixels of the array to obtain output signals representing analyte measurements). In various implementations, one or more components constituting one or more array controllers may be implemented together with pixel elements of the arrays themselves, on the same integrated circuit (IC) chip as the array but in a different portion of the IC chip, or off-chip. In connection with array control, analog-to-digital conversion of ISFET output signals may be performed by circuitry implemented on the same integrated circuit chip as the ISFET array, but located outside of the sensor array region (locating the analog to digital conversion circuitry outside of the sensor array region allows for smaller pitch and hence a larger number of sensors, as well as reduced noise). In various exemplary implementations discussed further below, analog-to-digital conversion can be 4-bit, 8-bit, 12-bit, 16-bit or other bit resolutions depending on the signal dynamic range required.

In general, data may be removed from the array in serial or parallel or some combination thereof. On-chip controllers (or sense amplifiers) can control the entire chip or some portion of the chip. Thus, the chip controllers or signal amplifiers may be replicated as necessary according to the demands of the application. The array may, but need not be, uniform. For instance, if signal processing or some other constraint requires instead of one large array multiple smaller arrays, each with its own sense amplifiers or controller logic, that is quite feasible.

Having provided a general overview of the role of a chemFET (e.g., ISFET) array 100 in an exemplary system 1000 for measuring one or more analytes, following below are more detailed descriptions of exemplary chemFET arrays according to various inventive embodiments of the present disclosure that may be employed in a variety of applications. Again, for purposes of illustration, chemFET arrays according to the present disclosure are discussed below using the particular example of an ISFET array, but other types of chemFETs may be employed in alternative embodiments. Also, again, for purposes of illustration, chemFET arrays are discussed in the context of nucleic acid sequencing applications, however, the invention is not so limited and rather contemplates a variety of applications for the chemFET arrays described herein.

Sensor Layout and Array Fabrication

Figure 2:
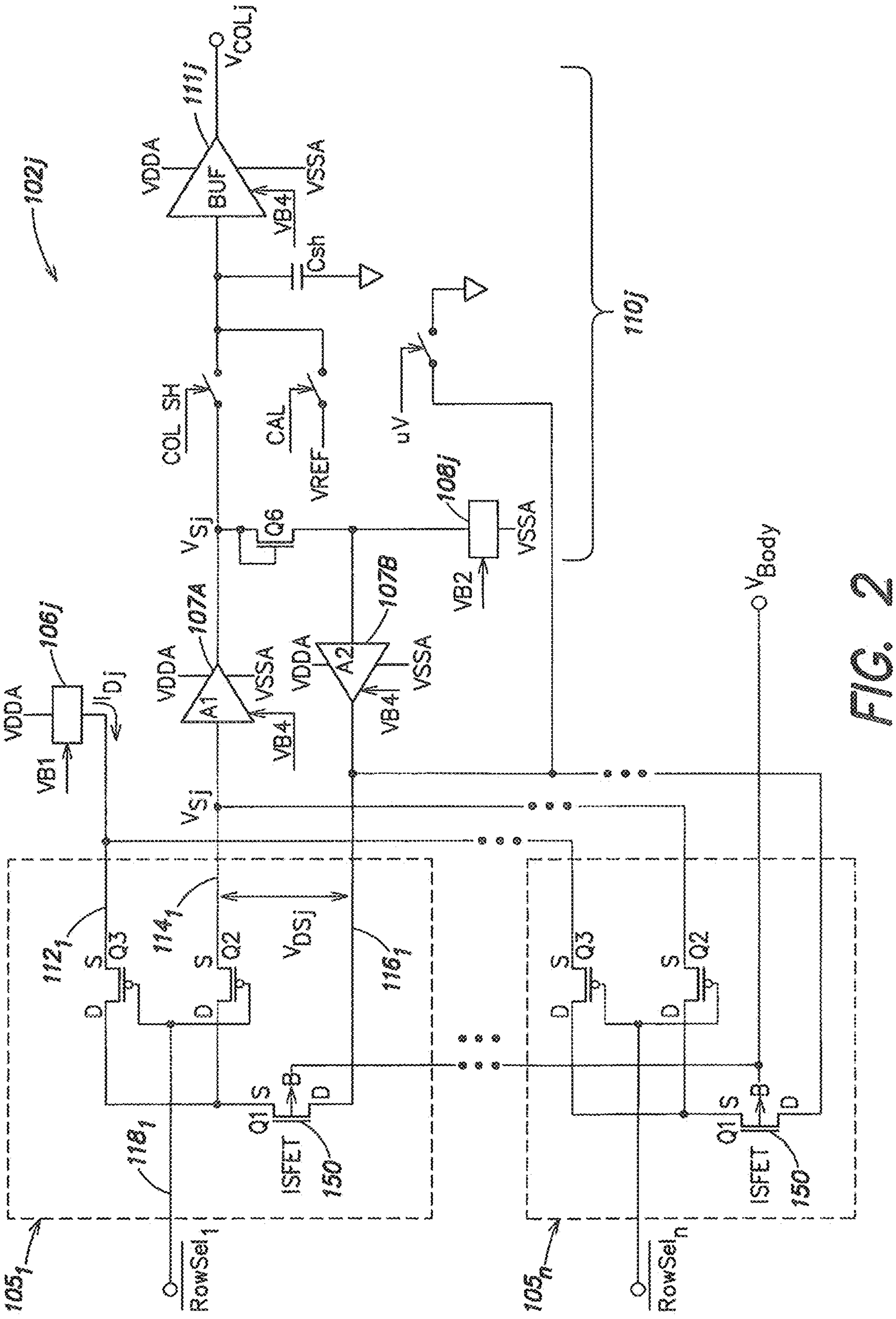
FIG. 2 illustrates one column of an chemFET array similar to that shown in FIG. 1, according to one inventive embodiment of the present disclosure.

Methods of sensor layout design and array fabrication are described in Rothberg et al., U.S. patent publications 2009/0026082 and 2009/0127589. In particular, techniques are disclosed for reducing or eliminating trapped charged during; accordingly, these references are incorporated by reference. In one aspect, the sensor design and signal readout circuitry may be employed in the present invention. For example, in one embodiment shown in FIG. 2, each chemFET of an array comprises a floating gate structure, and a source and a drain having a first semiconductor type and fabricated in a region having a second semiconductor type, wherein there is no electrical conductor that electrically connects the region having the second semiconductor type to either the source or the drain. Each sensor consists of three field effect transistors (FETs) including the chemFET, and each sensor includes a plurality of electrical conductors electrically connected to the three FETs. The three FETs are arranged such that the plurality of electrical conductors includes no more than four conductors traversing an area occupied by each sensor and interconnecting multiple sensors of the array. All of the FETs in each sensor are of a same channel type and implemented in a single semiconductor region of an array substrate. A collection of chemFET output signals from all chemFETs of the array constitutes a frame of data. The apparatus further comprises control circuitry coupled to the array and configured to generate at least one array output signal to provide multiple frames of data from the array at a frame rate of at least 20 frames per second.

Figure 3:
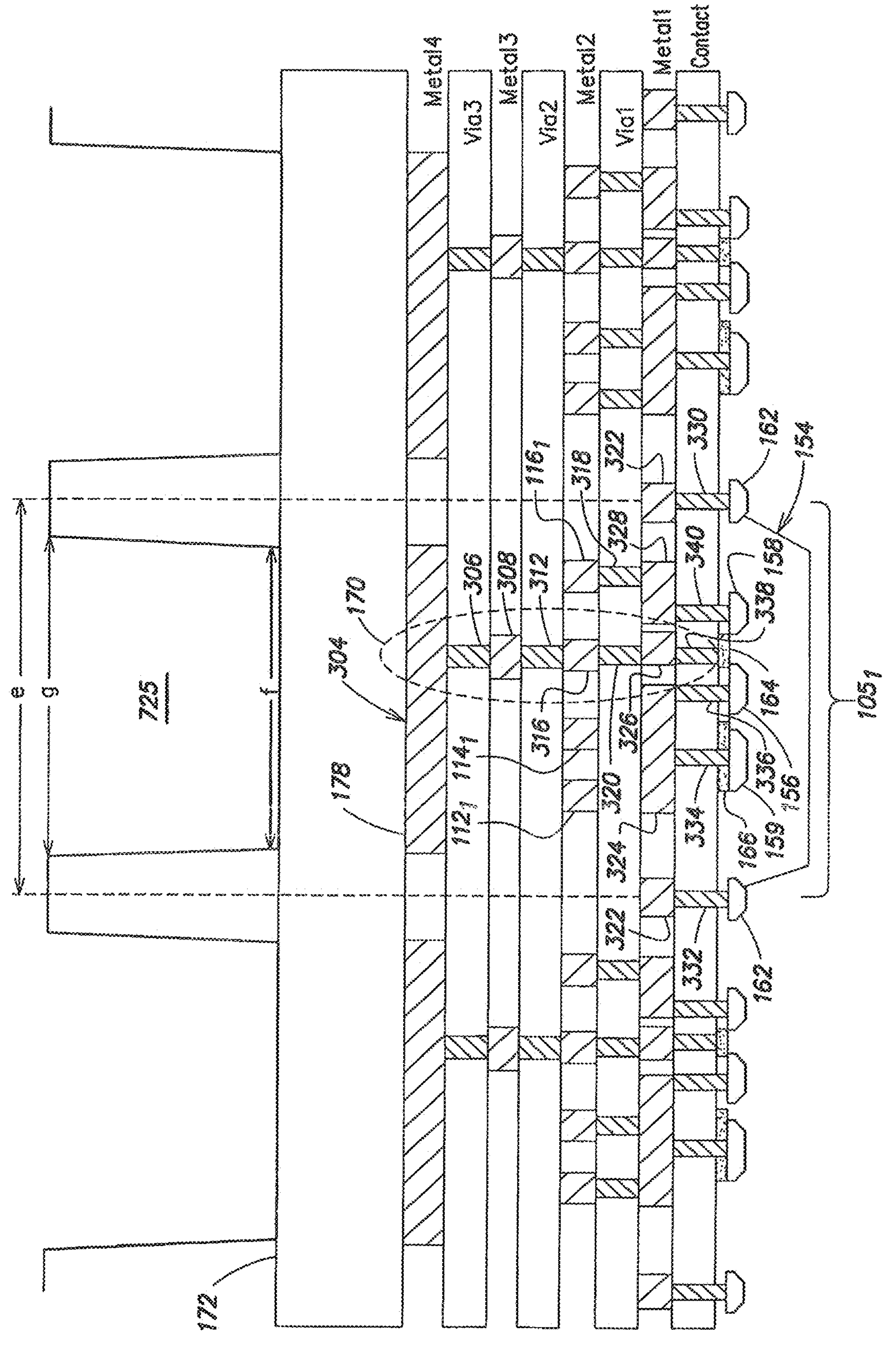
FIG. 3 shows a composite cross-sectional view of multiple neighboring pixels illustrating a layer-by-layer view of pixel fabrication according to another inventive embodiment of the present disclosure.
Figures 4A, 4B, 4C, 4D, 4E, 4F, 4G, 4H, 4I, 4J, 4K, 4L:
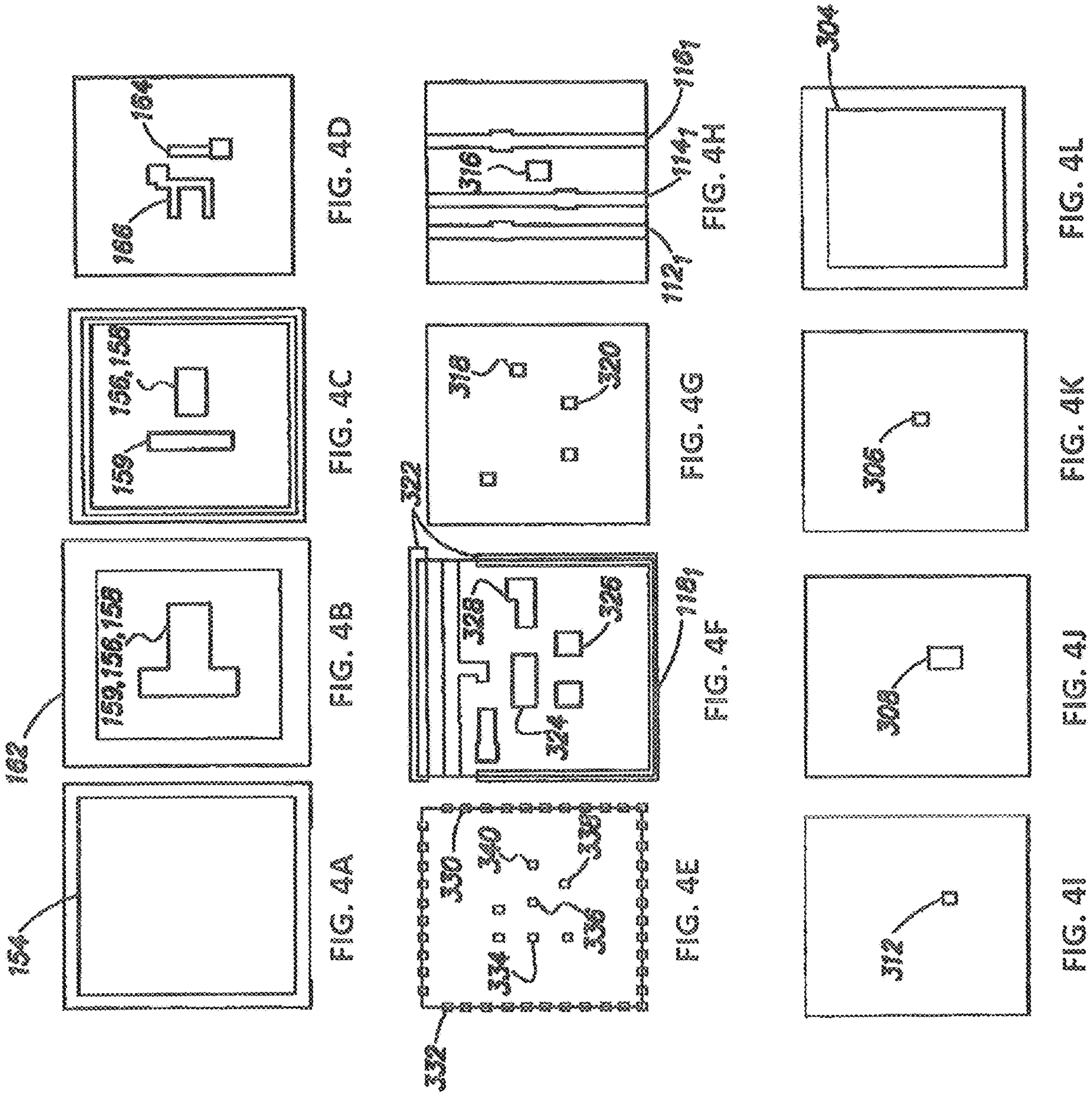
FIGS. 4A-4L are top views of patterns corresponding layers of material laid down in the fabrication of sensors shown in FIG. 3.

As an example of the integration of microwell and sensor arrays, FIG. 3 shows a composite cross-sectional view of neighboring pixels illustrating a layer-by-layer view of the pixel fabrication and relative positions of floating gates and microwells. Three adjacent pixels are shown in cross-section. All of the FET components of the pixel 1051 are fabricated asp-channel FETs in the single n-type well 154. Additionally, in the composite cross-sectional view of FIG. 3 the highly doped p-type region 159 is also visible corresponding to the shared drain (D) of the MOSFETs Q2 and Q3. For purposes of illustration, the polysilicon gate 166 of the MOSFET Q3 also is visible in FIG. 3. However, for simplicity, the respective sources of the MOSFETs Q2 and Q3 shown in FIG. 2, as well as the gate of Q2, are not visible in FIG. 3, as they lie along the same axis (i.e., perpendicular to the plane of the figure) as the shared drain. The topmost metal layer 304 corresponds to the ISFETs sensitive area 178, above which is disposed an analyte-sensitive passivation layer 172. The topmost metal layer 304, together with the ISFET polysilicon gate 164 and the intervening conductors 306, 308, 312, 316, 320, 326 and 338, form the ISFETs floating gate structure 170. However, an electrical connection to the ISFETs drain is provided by the conductors 340, 328, and 318, coupled to the line $\mathbf{116}_1$ which is formed in the Metal2 layer rather than the Metal3 layer. Additionally, the lines $\mathbf{112}_1$ and $\mathbf{114}_1$ also are shown in FIG. 3 as formed in the Metal2 layer rather than the Meta13 layer. The configuration of these lines, as well as the line $\mathbf{118}_1$, may be further appreciated from the respective images of FIGS. 4A through 4L; in particular, it may be observed in FIG. 4F that the line $\mathbf{118}_1$, together with the metal conductor 322, is formed in the Metal 1 layer, and it may be observed that the lines $\mathbf{112}_1$, $\mathbf{114}_1$ and $\mathbf{116}_1$ are formed in the Metal2 layer, leaving only the jumper 308 of the floating gate structure 170 in the Meta13 layer shown in FIG. 4J.

Accordingly, by consolidating the signal lines $\mathbf{112}_1$, $\mathbf{114}_1$, $\mathbf{116}_1$, and $\mathbf{118}_1$, to the Metal1 and Metal2 layers and thereby increasing the distance between these signal lines and the topmost layer 304 of the floating gate structure 170 in the Metal4 layer, parasitic capacitances in the ISFET may be at least partially mitigated. It should be appreciated that this general concept (e.g., including one or more intervening metal layers between signal lines and topmost layer of the floating gate structure) may be implemented in other fabrication processes involving greater numbers of metal layers. For example, distance between pixel signal lines and the topmost metal layer may be increased by adding additional metal layers (more than four total metal layers) in which only jumpers to the topmost metal layer are formed in the additional metal layers. In particular, a six-metal-layer fabrication process may be employed, in which the signal lines are fabricated using the Metal 1 and Metal2 layers, the topmost metal layer of the floating gate structure is formed in the Metal6 layer, and jumpers to the topmost metal layer are formed in the Metal3, Metal4 and Metal 5 layers, respectively (with associated vias between the metal layers).

In yet another aspect relating to reduced capacitance, a dimension "f" of the topmost metal layer 304 (and thus the ISFET sensitive area 178) may be reduced so as to reduce cross-capacitance between neighboring pixels. As may be observed in FIG. 4 (and as discussed further below in connection with other embodiments directed to well fabrication above an ISFET array), the well 725 may be fabricated so as to have a tapered shape, such that a dimension "g" at the top of the well is smaller than the pixel pitch "e" but yet larger than a dimension "f" at the bottom of the well. Based on such tapering, the topmost metal layer 304 also may be designed with the dimension "f" rather than the dimension "g" so as to provide for additional space between the top metal layers of neighboring pixels. In some illustrative non-limiting implementations, for pixels having a dimension "e" on the order of 9 micrometers the dimension "f" may be on the order of 6 micrometers (as opposed to 7 micrometers, as discussed above), and for pixels having a dimension "e" on the order of 5 micrometers the dimension "f" may be on the order of 3.5 micrometers.

Detection of hydrogen ions, and other analytes as determined by the invention, can be carried out using a passivation layer made of silicon nitride ($Si_3N_4$), silicon oxynitride ($Si_2N_2O$), silicon oxide ($SiO_2$), aluminum oxide ($Al_2O_3$), tantalum pentoxide ($Ta_2O_5$), tin oxide or stannic oxide ($SnO_2$), and the like.

When a dielectric layer is added over the floating gate structure of the ISFET sensor arrangement, the path from the analyte to the ISFET gate may be modeled as a series connection of three capacitances: (1) the capacitance attributable to the above-described charge double layer at the analyte-dielectric layer interface (labeled $C_{DL}$), (2) the capacitance due to the floating gate dielectric layer ($C_{FGD}$), and (3) the gate oxide capacitance ($C_{ox}$). (Note that in the text above, the floating gate dielectric layer is sometimes referred to as a "passivation" layer. Here, we refer more specifically to the layer as a floating gate dielectric layer in order to avoid any suggestion that the material composition of the layer is necessarily related to the so-called passivation material(s) often used in CMOS processing (e.g., PECVD silicon nitride) to coat and protect circuit elements.) The series capacitance string extends between the liquid analyte in the wells and the ISFET gate.

It is well known that capacitances in series form a capacitive voltage divider. Consequently, only a fraction of the signal voltage, $V_s$, generated by or in the analyte, is applied to the gate oxide as the voltage $V_G$ that drives the ISFET. If we define the gate gain as $V_G/V_S$, one would ideally like to have unity gain—i.e., no signal loss across any of the three capacitances. The value of $C_{DL}$ is a function of material properties and is typically on the order of about 10-40 $\mu F/cm^2$. The gate oxide capacitance is typically a very small value by comparison. Thus, by making $C_{FGD}$ much greater than the series combination of $C_{ox}$ and $C_{DL}$ (for short, $C_{FGD}>>C_{ox}$), the gate gain can be made to approach unity as closely as is practical.

To achieve the relationship $C_{FGD}>>C_{ox}$, one can minimize $C_{ox}$, maximize $C_{FGD}$, or both. Maximization of $C_{FGD}$ can be achieved by using a thin layer of high dielectric constant material, or by increasing the area of the floating gate metallization. The capacitance $C_{FGD}$ is essentially formed by a parallel plate capacitor having the floating gate dielectric layer as its dielectric. Consequently, for a given plate (i.e., floating gate metallization) area, the parameters principally available for increasing the value of $C_{FGD}$ are (1) the thickness of the dielectric layer and (2) the selection of the dielectric material and, hence, its dielectric constant. The capacitance of the floating gate dielectric layer varies directly with its dielectric constant and inversely with its thickness. Thus, a thin, high-dielectric-constant layer would be preferred, to satisfy the objective of obtaining maximum gate gain.

One candidate for the floating gate dielectric layer material is the passivation material used by standard CMOS foundry processes. The standard (typically, PECVD nitride or, to be more precise, silicon nitride over silicon oxynitride) passivation layer is relatively thick when formed (e.g., about 1.3 μm), and typical passivation materials have a limited dielectric constant. A first improvement can be achieved by thinning the passivation layer after formation. This can be accomplished by etching back the CMOS passivation layer, such as by using an over-etch step during microwell formation, to etch into and consume much of the nitride passivation layer, leaving a thinner layer, such as a layer only about 200-600 Angstroms thick.

Two approaches have been used for etching a standard CMOS passivation layer of silicon nitride deposited over silicon oxynitride. A first approach is referred to as the "partial etch" technique; it involves etching away the silicon nitride layer plus approximately half of the silicon oxynitride layer before depositing the thin-film metal oxide sensing layer. The second approach referred to as the "etch-to-metal" technique, involves etching away all of the silicon nitride and silicon oxynitride layers before depositing the thin-film metal oxide sensing layer. With an ALD $Ta_2O_s$ thin-film sensing layer deposited over a "partial etch," ISFET gains from about 0.37 to about 0.43 have been obtained empirically, with sensor sensitivities of about 15.02-17.08 mV/pH.

Figure 5A:
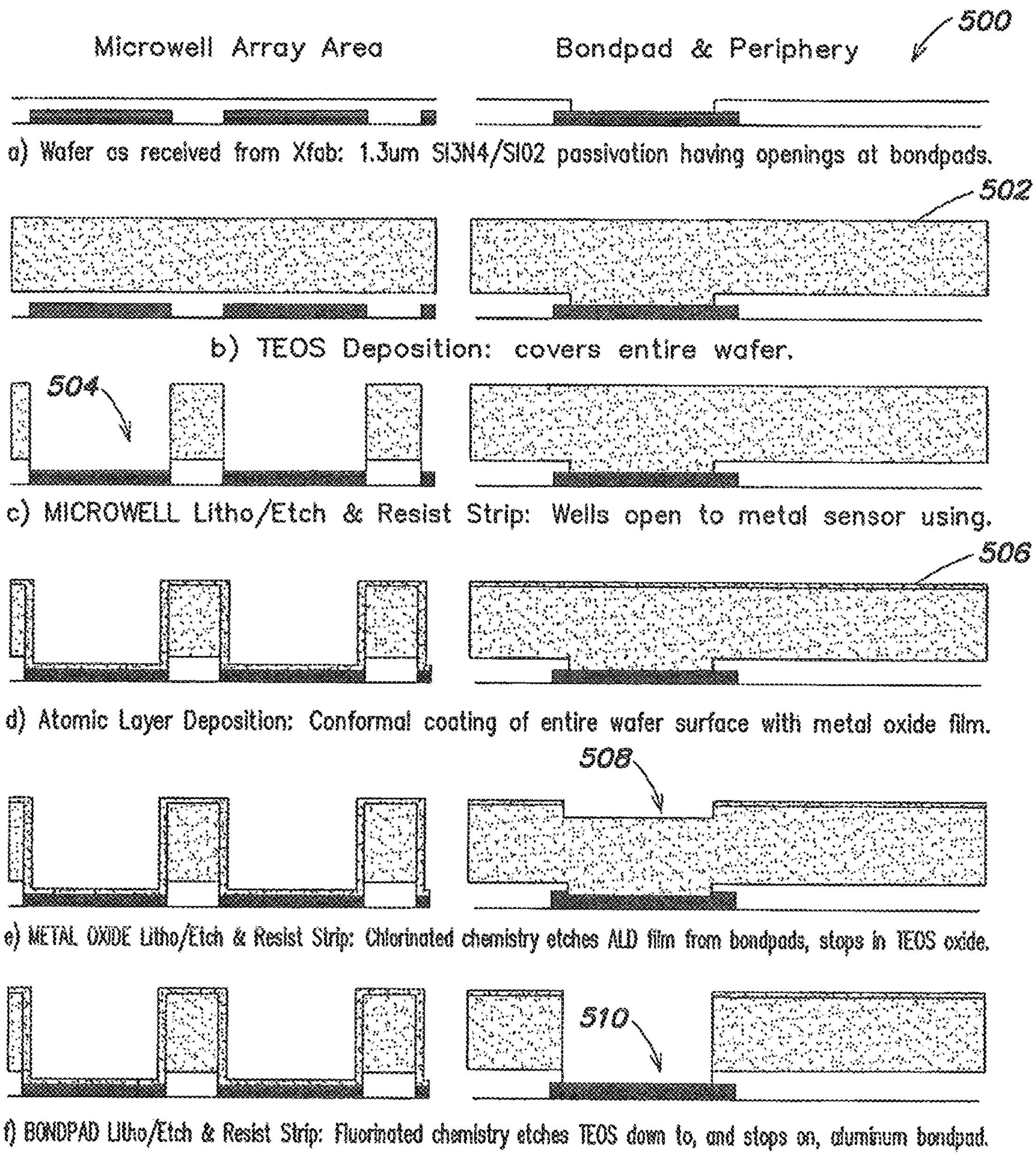
FIG. 5A-5B illustrates process steps for fabricating an array with thin dielectric layers on sensor floating gates, and a dielectric layer comprising a charge-sensitive layer and an adhesion layer.
Figure 5B:
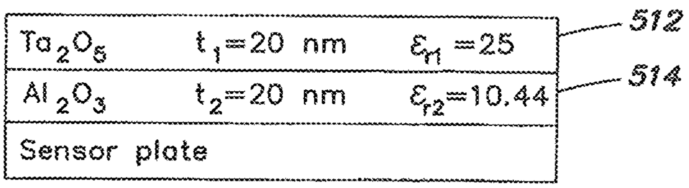

An alternative is to simply deposit a thinner layer of dielectric (passivation) material in the first place, such as the indicated 200-600 Angstroms instead of the 1.3 μm of the conventional CMOS passivation process. Materials useful for the floating gate dielectric layer are metal oxides such as tantalum oxide, tungsten oxide, aluminum oxide, and hafnium oxide, though other materials of dielectric constant greater than that of the usual silicon nitride passivation material may be substituted, provided that such material is, or can be rendered, sensitive to the ion of interest. The etch-to-metal approach is preferred, with the CMOS process' passivation oxide on the floating gate being etched completely away prior to depositing the floating gate dielectric material layer. That dielectric layer may be applied directly on the metal extended ISFET floating gate electrode. This will help maximize the value of the capacitance $C_{FGD}$. FIGS. 5A and 5B show steps using readily available fabrication techniques for generating a dielectric layer for high capacitive coupling to array sensor plates. Process steps additionally provide electrical access to bondpad structures for off-chip communication. Initially wafer (500) from a semiconductor manufacturer is treated to apply material layer (502) from which microwells are formed (in this example, TEOS), after which microwells are formed by etching to the metal of the senor plate (504). Dielectric layer (506) is added, for example, by atomic layer deposition. In one embodiment, as illustrated in FIG. 5B, dielectric layer (506) comprises a charge-sensitive layer (512) and an adhesion layer (514). Using alternative techniques and materials either single or multipli-component dielectric layers may be formed. Tantalum oxide and aluminum are exemplary charge-sensitive and adhesion layers of dielectric layer (506). As mentioned above, other materials from which dielectric layer (506) may be formed include $Ta_2O_5$ 5, $Al_2O_3$, $HfO_2$ or $WO_3$. In particular, such materials result in a larger signal in response to pH changes in a sample fluid. Iridium oxide may also be used, e.g. as described in D. O.

Wipf et al., "Microscopic Measurement of pH with Iridium Oxide Microelectrodes," Anal. Chem. 2000, 72, 4921-4927, and Y. J. Kim et al., "Configuration for Micro pH Sensor," Electronics Letters, Vol. 39, No. 21 (Oct. 16, 2003).

Chip Control and Readout Circuitry

Figure 6:
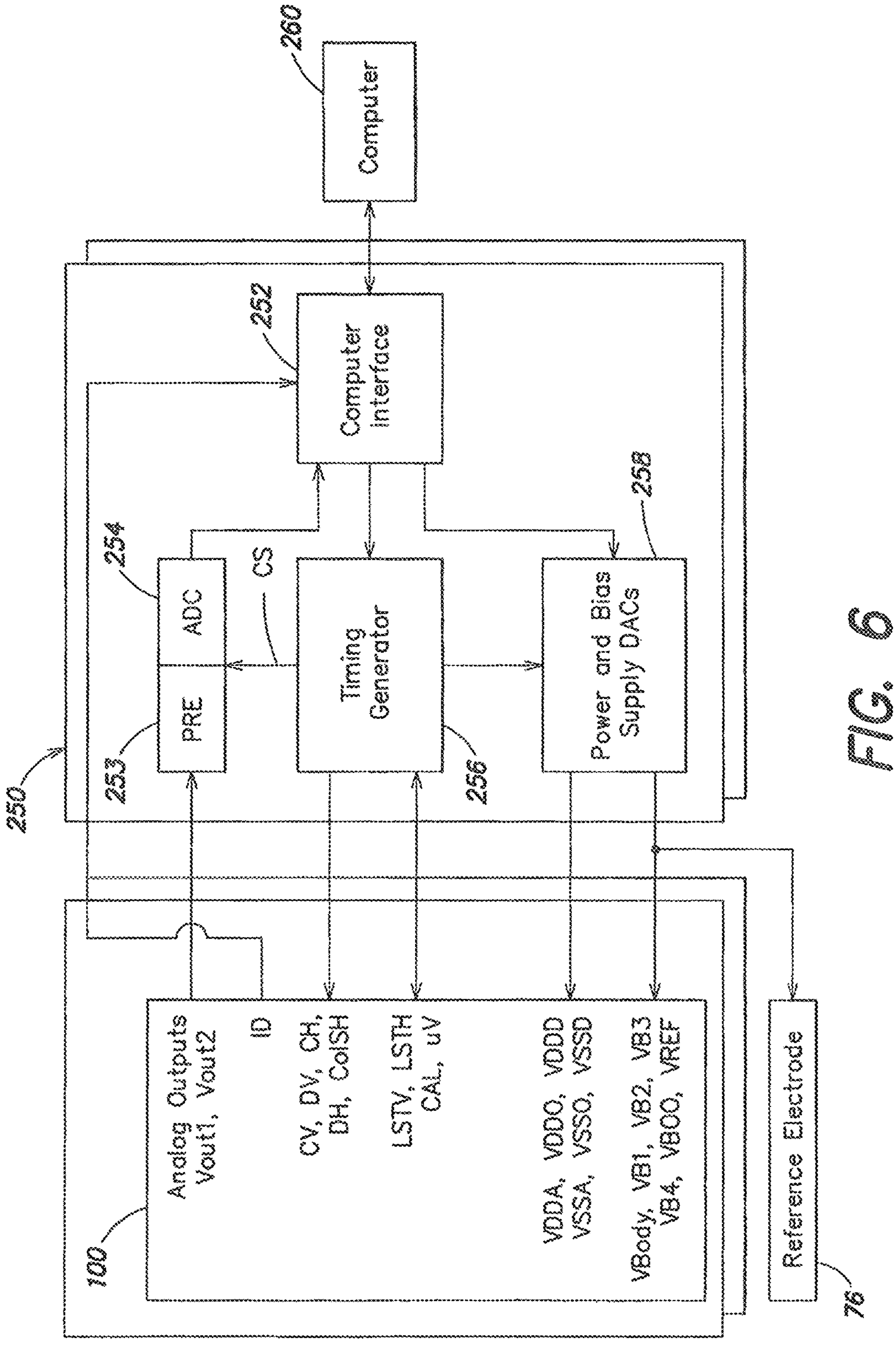
FIG. 6 is a block diagram of an embodiment of the electronic components of one embodiment of the invention.

A wide variety of on-chip architectures and circuit designs may be used for acquiring and processing output signals generated by sensors in arrays of the invention. Several approaches are disclosed in Rothberg et al., U.S. patent publications 2009/0026082 and 2009/0127589, which may be used with arrays of the present invention. For example, FIG. 6 illustrates a block diagram of the sensor array 100 coupled to an array controller 250, according to one inventive embodiment of the present disclosure. In various exemplary implementations, the array controller 250 may be fabricated as a "stand alone" controller, or as one or more computer compatible "cards" forming part of a computer 260 In one aspect, the functions of the array controller 250 may be controlled by the computer 260 through an interface block 252 (e.g., serial interface, via USB port or PCI bus, Ethernet connection, etc.). In one embodiment, all or a portion of the array controller 250 is fabricated as one or more printed circuit boards, and the array 100 is configured to plug into one of the printed circuit boards, similar to a conventional IC chip (e.g., the array 100 is configured as an ASIC that plugs into a chip socket, such as a zero-insertion-force or "ZIF" socket, of a printed circuit board). In one aspect of such an embodiment, an array 100 configured as an ASIC may include one or more pins/terminal connections dedicated to providing an identification code that may be accessed/read by the array controller 250 and/or passed on to the computer 260. Such an identification code may represent various attributes of the array 100 (e.g., size, number of pixels, number of output signals, various operating parameters such as supply and/or bias voltages, etc.) and may be processed to determine corresponding operating modes, parameters and or signals provided by the array controller 250 to ensure appropriate operation with any of a number of different types of arrays 100. In one exemplary implementation, an array 100 configured as an ASIC may be provided with three pins dedicated to an identification code, and during the manufacturing process the ASIC may be encoded to provide one of three possible voltage states at each of these three pins (i.e., a tri-state pin coding scheme) to be read by the array controller 250, thereby providing for unique array identification codes. In another aspect of this embodiment, all or portions of the array controller 250 may be implemented as a field programmable gate array (FPGA) configured to perform various array controller functions described in further detail below.

Generally, the array controller 250 provides various supply voltages and bias voltages to the array 100, as well as various signals relating to row and column selection, sampling of pixel outputs and data acquisition. In particular, the array controller 250 reads one or more analog output signals (e.g., $V_{out1}$ and $V_{out2}$) including multiplexed respective pixel voltage signals from the array 100 and then digitizes these respective pixel signals to provide measurement data to the computer 260, which in turn may store and/or process the data. In some implementations, the array controller 250 also may be configured to perform or facilitate various array calibration and diagnostic functions. Array controller 250 generally provides to the array 100 the analog supply voltage and ground (VDDA, VSSA), the digital supply voltage and ground (VDDD, VSSD), and the buffer output supply voltage and ground (VDDO, VSSO). In one exemplary implementation, each of the supply voltages VDDA, VDDD and VDDO is approximately 3.3 Volts. In another implementation, the supply voltages VDDA, VDDD and VDDO may be as low as approximately 1.8 Volts. As discussed above, in one aspect each of these power supply voltages is provided to the array 100 via separate conducting paths to facilitate noise isolation. In another aspect, these supply voltages may originate from respective power supplies/regulators, or one or more of these supply voltages may originate from a common source in a power supply 258 of the array controller 250. The power supply 258 also may provide the various bias voltages required for array operation (e.g., VBI, VB2, VB3, VB4, VBO0, $V_{BODY}$) and the reference voltage VREF used for array diagnostics and calibration.

In another aspect, the power supply 258 includes one or more digital-to-analog converters (DACs) that may be controlled by the computer 260 to allow any or all of the bias voltages, reference voltage, and supply voltages to be changed under software control (i.e., programmable bias settings). For example, a power supply 258 responsive to computer control (e.g., via software execution) may facilitate adjustment of one or more of the supply voltages (e.g., switching between 3.3 Volts and 1.8 Volts depending on chip type as represented by an identification code), and or adjustment of one or more of the bias voltages VBI and VB2 for pixel drain current, VB3 for column bus drive, VB4 for column amplifier bandwidth, and VBO0 for column output buffer current drive. In some aspects, one or more bias voltages may be adjusted to optimize settling times of signals from enabled pixels. Additionally, the common body voltage $V_{BODY}$ for all ISFETs of the array may be grounded during an optional post-fabrication UV irradiation treatment to reduce trapped charge, and then coupled to a higher voltage (e.g., VDDA) during diagnostic analysis, calibration, and normal operation of the array for measurement/data acquisition. Likewise, the reference voltage VREF may be varied to facilitate a variety of diagnostic and calibration functions.

As shown in FIG. 6, the reference electrode 76 which is typically employed in connection with an analyte solution to be measured by the array 100 may be coupled to the power supply 258 to provide a reference potential for the pixel output voltages. For example, in one implementation the reference electrode 76 may be coupled to a supply ground (e.g., the analog ground VSSA) to provide a reference for the pixel output voltages. In other exemplary implementations, the reference electrode voltage may be set by placing a solution/sample of interest having a known pH level in proximity to the sensor array 100 and adjusting the reference electrode voltage until the array output signals $V_{out1}$ and $V_{out2}$ provide pixel voltages at a desired reference level, from which subsequent changes in pixel voltages reflect local changes in pH with respect to the known reference pH level. In general, it should be appreciated that a voltage associated with the reference electrode 76 need not necessarily be identical to the reference voltage VREF discussed above (which may be employed for a variety of array diagnostic and calibration functions), although in some implementations the reference voltage VREF provided by the power supply 258 may be used to set the voltage of the reference electrode 76.

Regarding data acquisition from the array 100, in one embodiment the array controller 250 of FIG. 6 may include one or more preamplifiers 253 to further buffer one or more output signals (e.g., $V_{out1}$ and $V_{out2}$) from the sensor array and provide selectable gain. In one aspect, the array controller 250 may include one preamplifier for each output signal (e.g., two preamplifiers for two analog output signals). In other aspects, the preamplifiers may be configured to accept input voltages from 0.0 to 1.8 Volts or 0.0 to 3.3 Volts, may have programmable/computer selectable gains (e.g., 1, 2, 5, 10 and 20) and low noise outputs (e.g., <10 n V/sqrtHz), and may provide low pass filtering (e.g., bandwidths of 5 MHz and 25 MHz). With respect to noise reduction and increasing signal-to-noise ratio, in one implementation in which the array 100 is configured as an ASIC placed in a chip socket of a printed circuit board containing all or a portion of the array controller 250, filtering capacitors may be employed in proximity to the chip socket (e.g., the underside of a ZIF socket) to facilitate noise reduction. In yet another aspect, the preamplifiers may have a programmable/computer selectable offset for input and/or output voltage signals to set a nominal level for either to a desired range.

The array controller 250 of FIG. 6 also comprises one or more analog-to-digital converters 254 (ADCs) to convert the sensor array output signals $V_{out1}$ and $V_{out2}$ to digital outputs (e.g., 10-bit or 12-bit) so as to provide data to the computer 260. In one aspect, one ADC may be employed for each analog output of the sensor array, and each ADC may be coupled to the output of a corresponding preamplifier (if preamplifiers are employed in a given implementation). In another aspect, the ADC(s) may have a computer-selectable input range (e.g., 50 mV, 200 mV, 500 mV, IV) to facilitate compatibility with different ranges of array output signals and/or preamplifier parameters. In yet other aspects, the bandwidth of the ADC(s) may be greater than 60 MHz, and the data acquisition/conversion rate greater than 25 MHz (e.g., as high as 100 MHz or greater).

In the embodiment of FIG. 6, ADC acquisition timing and array row and column selection may be controlled by a timing generator 256. In particular, the timing generator provides the digital vertical data and clock signals (DV, CV) to control row selection, the digital horizontal data and clock signals (DH, CH) to control column selection, and the column sample and hold signal COL SH to sample respective pixel voltages for an enabled row. The timing generator 256 also provides a sampling clock signal CS to the ADC(s) 254 so as to appropriately sample and digitize consecutive pixel values in the data stream of a given array analog output signal (e.g., $V_{out1}$ and $V_{out2}$), as discussed further below in connection with FIG. 7. In some implementations, the timing generator 256 may be implemented by a microprocessor executing code and configured as a multichannel digital pattern generator to provide appropriately timed control signals. In one exemplary implementation, the timing generator 256 may be implemented as a field-programmable gate array (FPGA).

Figure 7:
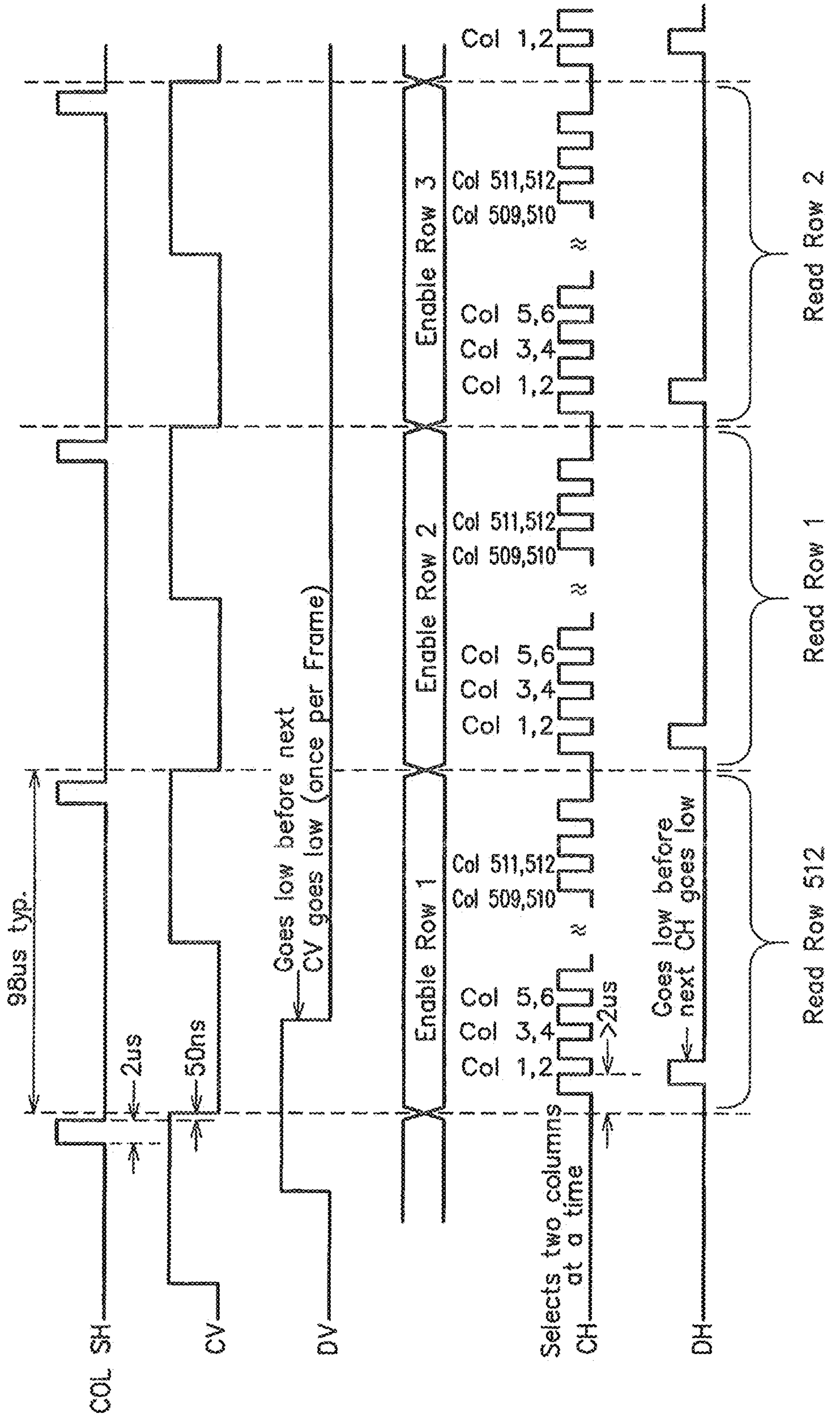
FIG. 7 is an exemplary timing diagram for components shown in FIG. 6.

FIG. 7 illustrates an exemplary timing diagram for various array control signals, as provided by the timing generator 256, to acquire pixel data from the sensor array 100. For purposes of the following discussion, a "frame" is defined as a data set that includes a value (e.g., pixel output signal or voltage $V_s$) for each pixel in the array, and a "frame rate" is defined as the rate at which successive frames may be acquired from the array. Thus, the frame rate corresponds essentially to a "pixel sampling rate" for each pixel of the array, as data from any given pixel is obtained at the frame rate.

In the example of FIG. 7, an exemplary frame rate of 20 frames/sec is chosen to illustrate operation of the array (i.e., row and column selection and signal acquisition); however, it should be appreciated that arrays and array controllers according to the present disclosure are not limited in this respect, as different frame rates, including lower frame rates (e.g., 1 to 10 frames/second) or higher frame rates (e.g., 25, 30, 40, 50, 60, 70 to 100 frames/sec., etc.), with arrays having the same or higher numbers of pixels, are possible. In some exemplary applications, a data set may be acquired that includes many frames over several seconds to conduct an experiment on a given analyte or analytes. Several such experiments may be performed in succession, in some cases with pauses in between to allow for data transfer/processing and/or washing of the sensor array ASIC and reagent preparation for a subsequent experiment.

For example, with respect to the method for detecting nucleotide incorporation, appropriate frame rates may be chosen to sufficiently sample the JSFET's output signal. In some exemplary implementations, a hydrogen ion signal may have a full-width at half-maximum (FWHM) on the order of approximately 1 second to approximately 2.5 seconds, depending on the number of nucleotide incorporation events. Given these exemplary values, a frame rate (or pixel sampling rate) of 20 Hz is sufficient to reliably resolve the signals in a given pixel's output signal. Again, the frame rates given in this example are provided primarily for purposes of illustration, and different frame rates may be involved in other implementations.

In one implementation, the array controller 250 controls the array 100 to enable rows successively, one at a time. For example, a first row of pixels is enabled via the row select signal $\overline{\text{RowSel1}}$. The enabled pixels are allowed to settle for some time period, after which the COL SH signal is asserted briefly to close the sample/hold switch in each column and store on the column's sample/hold capacitor $C_{sh}$ the voltage value output by the first pixel in the column. This voltage is then available as the column output voltage $V_{COLj}$ applied to one of the two (odd and even column) array output drivers. The COL SH signal is then de-asserted, thereby opening the sample/hold switches in each column and decoupling the column output buffer 111$_j$ from the column amplifiers 107A and 107B. Shortly thereafter, the second row of pixels is enabled via the row select signal $\overline{\text{RowSel2}}$. During the time period in which the second row of pixels is allowed to settle, the column select signals are generated two at a time (one odd and one even; odd column select signals are applied in succession to the odd output driver, even column select signals are applied in succession to the even output driver) to read the column output voltages associated with the first row. Thus, while a given row in the array is enabled and settling, the previous row is being read out, two columns at a time. By staggering row selection and sampling/readout (e.g., via different vertical and horizontal clock signals and column sample/hold), and by reading multiple columns at a time for a given row, a frame of data may be acquired from the array in a significantly streamlined manner.

FIG. 7 illustrates the timing details of the foregoing process for an exemplary frame rate of 20 frames/sec. In a 512×512 array, each row must be read out in approximately 98 microseconds, as indicated by the vertical delineations in FIG. 7. Accordingly, the vertical clock signal CV has a period of 98 microseconds (i.e., a clock frequency of over 10 kHz), with a new row being enabled on a trailing edge (negative transition) of the CV signal. The left side of FIG. 7 reflects the beginning of a new frame cycle, at which point the vertical data signal DV is asserted before a first trailing edge of the CV signal and de-asserted before the next trailing edge of the CV signal. Also, immediately before each trailing edge of the CV signal (i.e., new row enabled), the COL SH signal is asserted for 2 microseconds, leaving approximately 50 nanoseconds before the trailing edge of the CV signal.

In FIG. 7, the first occurrence of the COL SH signal is actually sampling the pixel values of row 512 of the 512×512 array. Thus, upon the first trailing edge of the CV signal, the first row is enabled and allowed to settle (for approximately 96 microseconds) until the second occurrence of the COL SH signal. During this settling time for the first row, the pixel values of row 512 are read out via the column select signals. Because two column select signals are generated simultaneously to read 512 columns, the horizontal clock signal CH must generate 256 cycles within this period, each trailing edge of the CH signal generating one odd and one even column select signal. As shown in FIG. 7, the first trailing edge of the CH signal in a given row is timed to occur two microseconds after the selection of the row (after deactivation of the COL SH signal) to allow for settling of the voltage values stored on the sample/hold capacitors $C_{sh}$ and provided by the column output buffers. It should be appreciated however that, in other implementations, the time period between the first trailing edge of the CH signal and a trailing edge (i.e., deactivation) of the COL SH signal may be significantly less than two microseconds, and in some cases as small as just over 50 nanoseconds. Also for each row, the horizontal data signal DH is asserted before the first trailing edge of the CH signal and de-asserted before the next trailing edge of the CH signal. The last two columns are selected before the occurrence of the COL SH signal which, as discussed above, occurs approximately two microseconds before the next row is enabled. Thus, in the above example, columns are read, two at a time, within a time period of approximately 94 microseconds (i.e., 98 microseconds per row, minus two microseconds at the beginning and end of each row). This results in a data rate for each of the array output signals $V_{out1}$ and $V_{out2}$ of approximately 2.7 MHz.

Noise coupled into the sample fluid by the sensors in every column of the array may be present in the output signals of a sensor. When a row is selected in the array, the drain terminal voltage shared between all of the ISFETs in a column moves up or down (as a necessary requirement of the source-and-drain follower). This changes the gate-to-drain capacitances of all of the unselected ISFETs in the column. In turn, this change in capacitance couples from the gate of every unselected ISFET into the fluid, ultimately manifesting itself as noise in the fluid (i.e., an incorrect charge, one not due to the chemical reaction being monitored). That is, any change in the shared drain terminal voltage can be regarded as injecting noise into the fluid by each and every unselected ISFET in the column. Hence, if the shared drain terminal voltage of the unselected ISFETs can be kept constant when selecting a row in the array, this mechanism of coupling noise into the fluid can be reduced or even effectively eliminated. When a row is selected in the array, the source terminal voltage of all of the unselected ISFETs in the column also changes. In turn, that changes the gate-to-source capacitance of all of these ISFETs in the column. This change in capacitance couples from the gate of every unselected ISFET into the fluid, again ultimately manifesting itself as noise in the fluid. That is, any change in the source terminal voltage of an unselected ISFET in the column can be regarded as an injection of noise into the fluid. Hence, if the source terminal voltage of the unselected ISFETs can be kept when selecting a row in the array, this mechanism of coupling noise into the fluid via can be reduced or even effectively eliminated.

A column buffer may be used with some passive pixel designs to alleviate the ISFET drain problem but not the ISFET source problem. Thus, a column buffer most likely is preferable to the above-illustrated source-and-drain follower. With the illustrated three-transistor passive pixels employing a source-and-drain follower arrangement, there are essentially two sense nodes, the ISFET source and drain terminals, By connecting the pixel to a column buffer and grounding the drain terminal of the ISFET, there will be only one sense node: the ISFET source terminal. So the drain problem is eliminated.

The above-described readout circuit, which comprises both sample-and-hold and multiplexer blocks, also has a gain that is less than the ideal value of unity. Furthermore, the sample and—hold block contributes a significant percentage of the overall chip noise, perhaps more than 25%. From switched-capacitor theory, the sample-and-hold "kT/C" noise is inversely proportional to capacitance. Hence, by choosing a larger capacitor, the sample-and-hold noise can be reduced. Another approach to reducing noise is to employ Correlated Double Sampling (CDS), where a second sample-and-hold and difference circuit is used to cancel out correlated noise. This approach is discussed at greater length, below.

Correlated Double Sampling (CDS) is a known technique for measuring electrical values such as voltages or currents that allows for removal of an undesired offset. The output of the sensor is measured twice: once in a known condition and once in an unknown condition. The value measured from the known condition is then subtracted from the unknown condition to generate a value with a known relation to the physical quantity being measured. The challenge here is how to be efficient in implementing CDS and how to address both correlated noise and the minimization of noise injection into the analyte fluid.

Figure 8A:
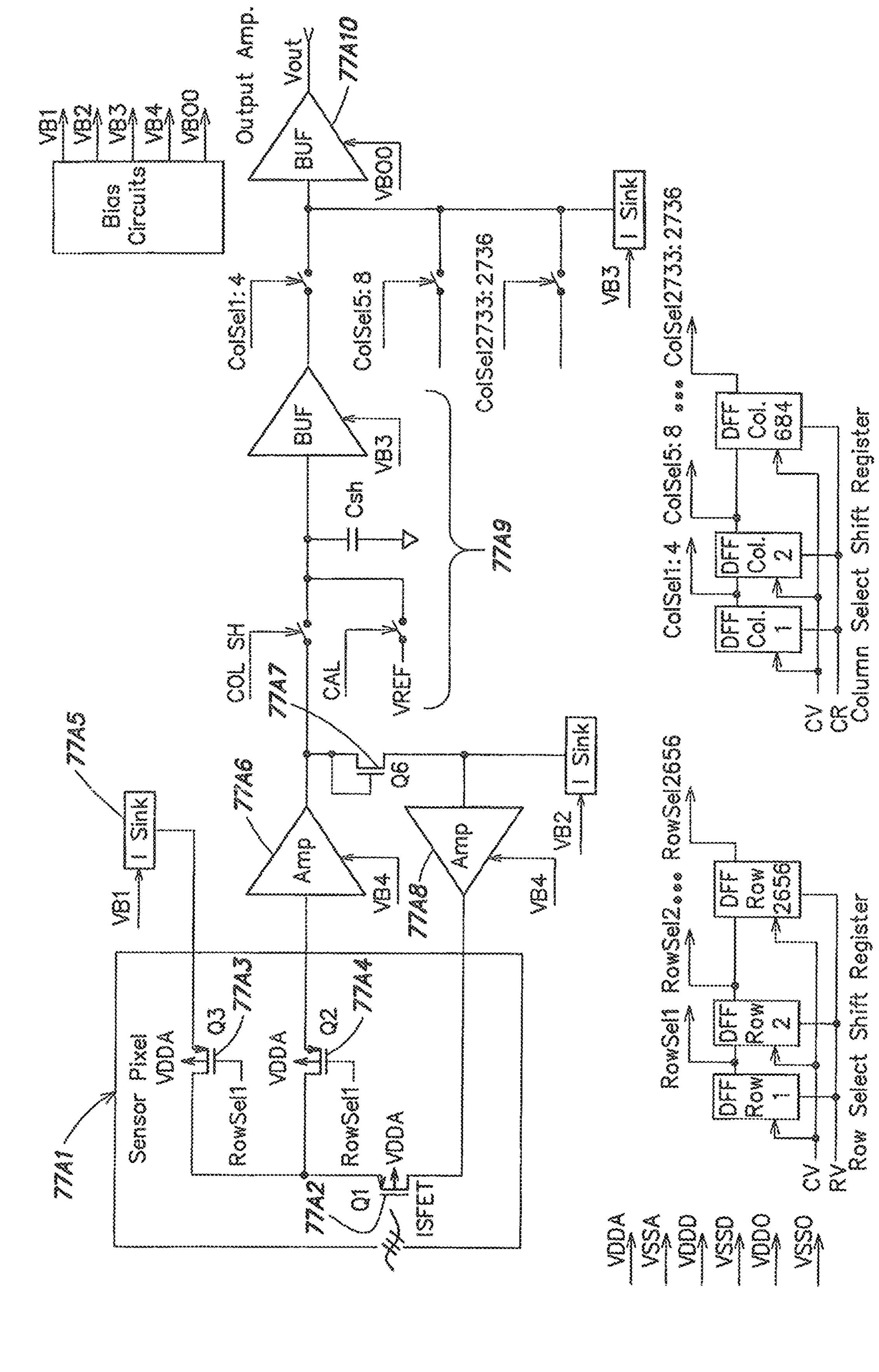
FIG. 8A is a high-level, partially block, partially circuit diagram showing a basic passive sensor pixel in which the voltage changes on the ISFET source and drain inject noise into the analyte, causing errors in the sensed values.

A starting point is the sensor pixel and its readout configuration as expressed in earlier parts of this application. Referring to FIG. 8A, the basic passive sensor pixel 77A1 is a three transistor arrangement of an ISFET 77A2 and a pair of row select transistors, 77A3 and 77A4 connected to the ISFET source. Transistor 77A3 is connected in turn to a current source or sink 77A5. A readout is obtained via transistor 77A4 which is connected to the input of sense amplifier 77A6. A diode-connected transistor 77A7 in series with another amplifier, 77A8, connects in a feedback loop from the output of the sense amplifier to the drain of the ISFET. The sense amplifier output is captured by a sample-and-hold circuit 77A9, which feeds an output amplifier 77A10.

Figure 8B:
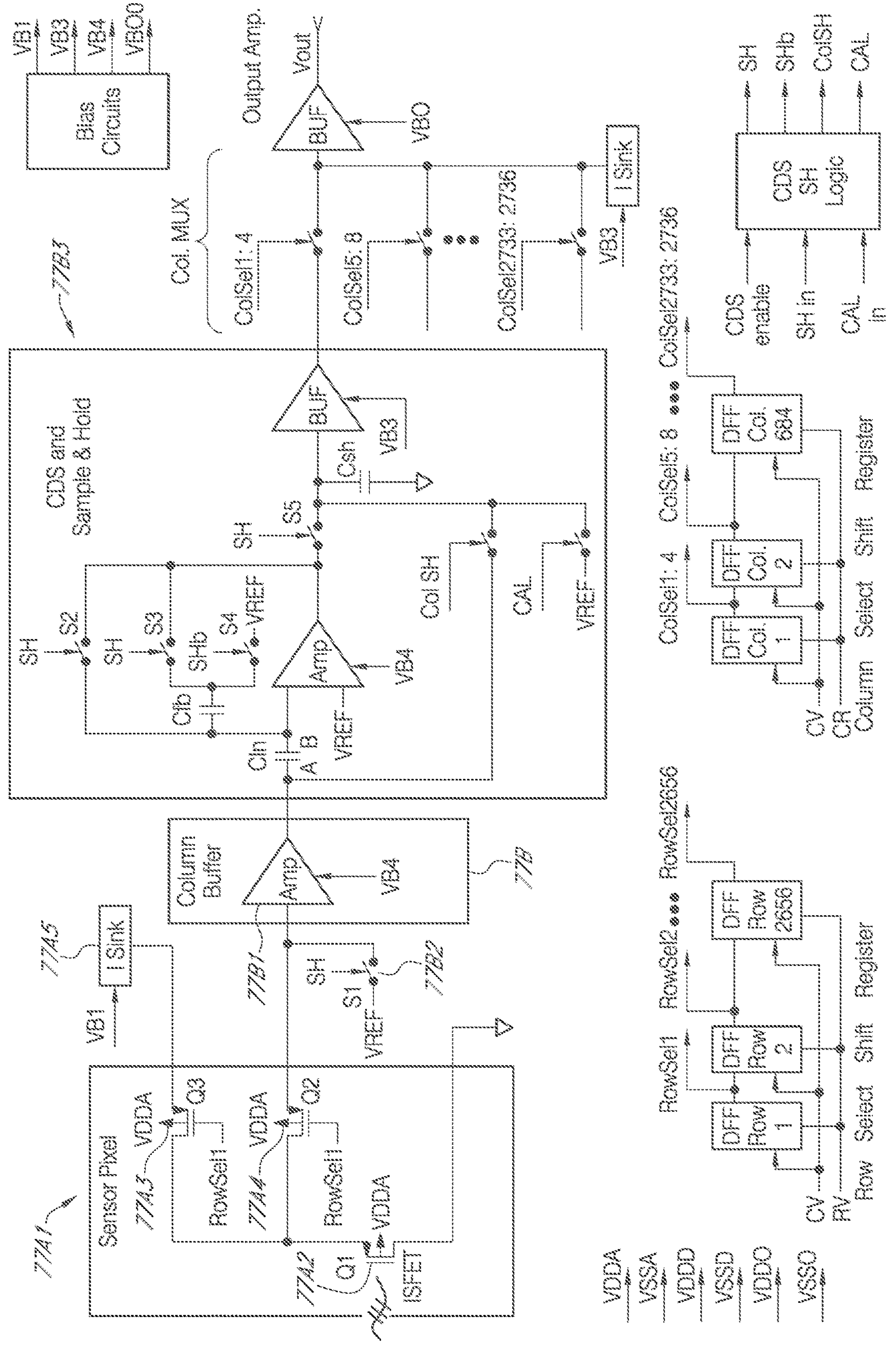
FIG. 8B is a high-level partially block, partially circuit diagram showing a basic passive sensor pixel in which the voltage changes on the ISFET drain are eliminated by tying it to ground, the pixel output is obtained via a column buffer, and CDS is employed on the output of the column buffer to reduce correlated noise.

As discussed above, the voltage changes on the ISFET source and drain inject noise into the analyte, causing errors in the sensed values. Two constructive modifications can reduce the noise level appreciably, as shown in FIG. 8B.

The first change is to alter the signals on the ISFET. The feedback loop to the drain of the ISFET is eliminated and the drain is connected to a stable voltage, such as ground. Column buffer 77B is connected to the emitter of transistor.

The second change is to include a circuit to perform CDS on the output of the column buffer. As mentioned above, CDS requires a first, reference value. This is obtained by connecting the input of column buffer 77B1 to a reference voltage via switch 77B2, during a first, or reference phase of a clock, indicated as the "SH" phase. A combined CDS and sample-and-hold circuit 77B3 then double samples the output of the column buffer, obtaining a reference sample and a sensed value, performs a subtraction, and supplies a resulting noise-reduced output value, since the same correlated noise appears in the reference sample and in the sensor output.

The operation of the CDS and sample-and-hold circuit 77B3 is straightforward. The circuit operates on a two-phase clock, the first phase being the SH phase and the second phase being the SHb phase. Typically, the phases will be symmetrical and thus inverted values of each other. The reference sample is obtained in the SH phase and places a charge (and thus a voltage) on capacitor Cin, which is subtracted from the output of the column buffer when the clock phase changes.

Figure 8C:
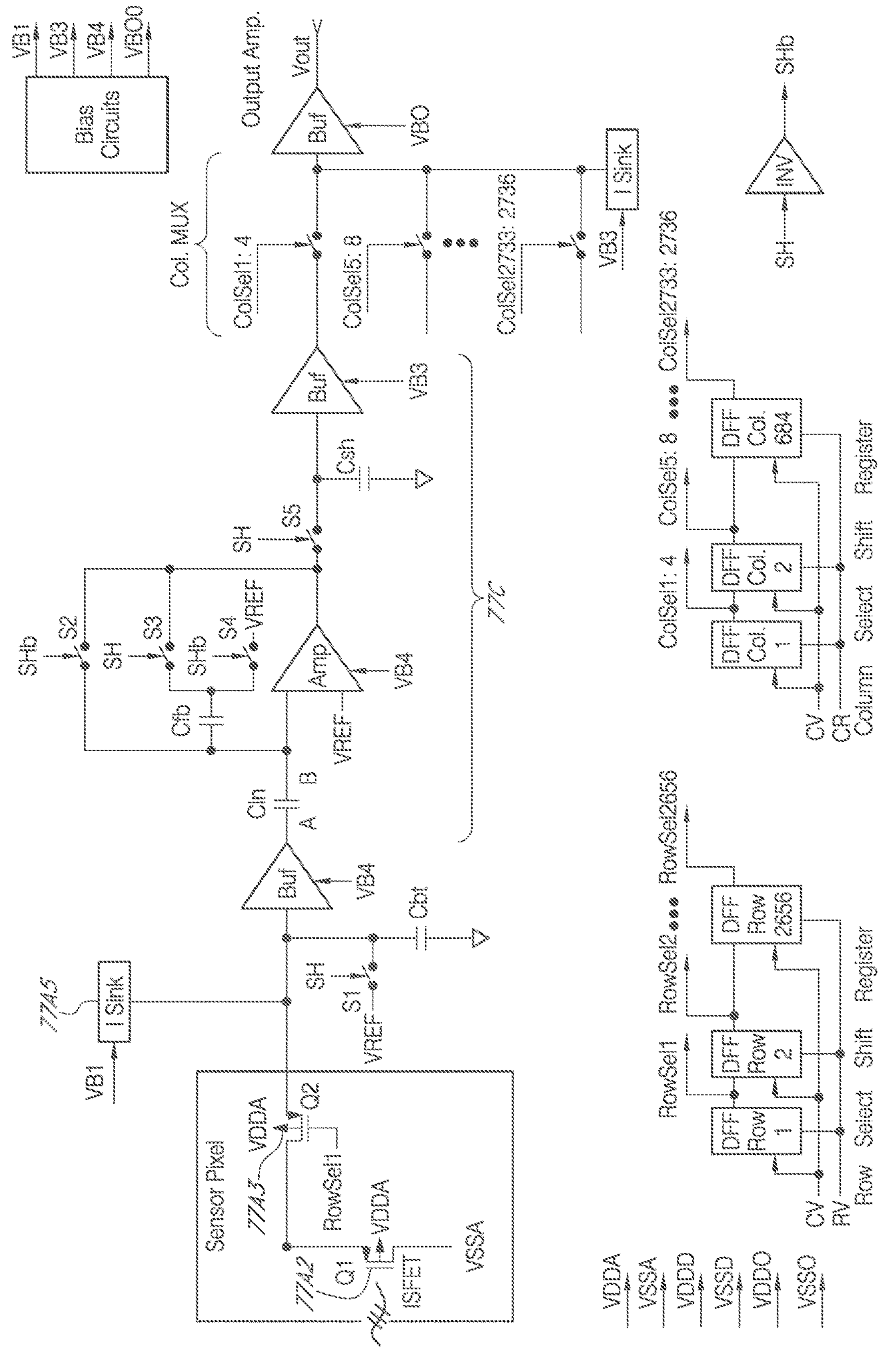
FIG. 8C is a high-level partially block, partially circuit diagram showing a two transistor passive sensor pixel in which the voltage changes on the ISFET drain and source are substantially eliminated, the pixel output is obtained via a buffer, and CDS is employed on the output of the column buffer to reduce correlated noise.

An alternative embodiment, still with a passive sensor pixel, is shown in FIG. 8C. The sensor pixel in this embodiment is a two-transistor circuit comprising ISFET whose drain is connected to a fixed supply voltage, VSSA. There is no transistor comparable to 77A4, and the pixel output is taken from the emitter of transistor 77A3, instead. The CDS and sample-and-hold circuit 77C has been simplified slightly, by the elimination of a feedback loop, but it serves the same function, in conjunction with the charge (voltage) stored on capacitor Cbt, of subtracting a reference value on capacitor Cin from the signal supplied by the sensor pixel.

Microwell Arrays

As discussed elsewhere, for many uses, such as in DNA sequencing, it is desirable to provide over the array of semiconductor sensors a corresponding array of microwells, each microwell being small enough preferably to receive only one DNA-loaded bead, in connection with which an underlying pixel in the array will provide a corresponding output signal.

The use of such a microwell array involves three stages of fabrication and preparation, each of which is discussed separately: (1) creating the array of microwells to result in a chip having a coat comprising a microwell array layer; (2) mounting of the coated chip to a fluidic interface; and in the case of DNA sequencing, (3) loading DNA-loaded bead or beads into the wells. It will be understood, of course, that in other applications, beads may be unnecessary or beads having different characteristics may be employed.

The systems described herein can include an array of microtluidic reaction chambers integrated with a semiconductor comprising an array of chemFETs. In some embodiments, the invention encompasses such an array. The reaction chambers may, for example, be formed in a glass, dielectric, photodefineable or etchable material. The glass material may be silicon dioxide.

Various aspects or embodiments of the invention involve an apparatus comprising an array of chemFET sensors overlayed with an array of reaction chambers wherein the bottom of a reaction chamber is in contact with (or capacitively coupled to) a chemFET sensor. In some embodiments, each reaction chamber bottom is in contact with a chemFET sensor, and preferably with a separate chemFET sensor. In some embodiments, less than all reaction chamber bottoms are in contact with a chemFET sensor. In some embodiments, each sensor in the array is in contact with a reaction chamber. In other embodiments, less than all sensors are in contact with a reaction chamber. The sensor (and/or reaction chamber) array may be comprised of 2, 3, 4, 5, 6, 7, 8, 9, 10, 15, 20, 30, 40, 50, 60, 60, 80, 90, 100, 200, 300, 400, 500, 1000, $10^4$, $10^5$, $10^6$, $10^7$, $10^8$, or more chemFET sensors (and/or reaction chambers). As used herein, it is intended that an array that comprises, as an example, 256 sensors or reaction chambers will contain 256 or more (i.e., at least 256) sensors or reaction chambers. It is further intended that aspects and embodiments described herein that "comprise" elements and/or steps also fully support and embrace aspects and embodiments that "consist of" or "consist essentially of" such elements and/or steps.

Various aspects and embodiments of the invention involve sensors (and/or reaction chambers) within an array that are spaced apart from each other at a center-to-center distance or spacing (or "pitch", as the terms are used interchangeably herein) that is in the range of 1-50 microns, 1-40 microns, 1-30 microns, 1-20 microns, 1-10 microns, or 5-10 microns, including equal to or less than about 9 microns, or equal to or less than about 5.1 microns, or 1-5 microns including equal to or less than about 2.8 microns. The center-to-center distance between adjacent reaction chambers in a reaction chamber array may be about 1-9 microns, or about 2-9 microns, or about 1 microns, about 2 microns, about 3 microns, about 4 microns, about 5 microns, about 6 microns, about 7 microns, about 8 microns, or about 9 microns.

In some embodiments, the reaction chamber has a volume of equal to or less than about 1 picoliter (pL), including less than 0.5 pL, less than 0.1 pL, less than 0.05 pL, less than 0.01 pL, less than 0.005 pL.

The reaction chambers may have a square cross section, for example, at their base or bottom. Examples include an 8 μm by 8 μm cross section, a 4 μm by 4 μm cross section, or a 1.5 μm by 1.5 μm cross section. Alternatively, they may have a rectangular cross section, for example, at their base or bottom. Examples include an 8 μm by 12 μm cross section, a 4 μm by 6 μm cross section, or a 1.5 μm by 2.25 μm cross section.

In another exemplary implementation, the invention encompasses a system comprising at least one two-dimensional array of reaction chambers, wherein each reaction chamber is coupled to a chemically-sensitive field effect transistor ("chemFET") and each reaction chamber is no greater than 10 $\mu m^3$ (i.e., 1 pL) in volume. Preferably, each reaction chamber is no greater than 0.34 pL, and more preferably no greater than 0.096 pL or even 0.012 pL in volume. A reaction chamber can optionally be $2^2$, $3^2$, $4^2$, $5^2$, $6^2$, $7^2$, $8^2$, $9^2$, or $10^2$ square microns in cross-sectional area at the top. Preferably, the array has at least $10^2$, $10^3$, $10^4$, $10^9$, $10^6$, $10^7$, $10^8$, $10^9$, or more reaction chambers. The reaction chambers may be capacitively coupled to the chemFETs, and preferably are capacitively coupled to the chemFETs. Such systems may be used for high-throughput sequencing of nucleic acids.

In some embodiments, the reaction chamber array (or equivalently, microwell array) comprises $10^2$, $10^3$, $10^4$, $10^9$, $10^6$, $10^7$ microwells or reaction chambers. In some embodiments, individual reaction chambers in the reaction chamber array are in contact with or capacitively coupled to at least one chemFET. In one embodiment, a reaction chamber of an array is in contact with or capacitively coupled to one chemFET or one ISFET. In some embodiments, the chemFET array may optionally comprise $10^2$, $10^3$, $10^4$, $10^5$, $10^6$, $10^7$ chemFETs.

In these and in other aspects and embodiments, the chemFET or ISFET arrays may comprise 256 or more chemFETs or ISFETs. The chemFETs or ISFETs of such arrays may have a center-to-center spacing (between adjacent chemFETs or ISFETs) of 1-10 microns. In some embodiments, the center-to-center spacing is about 9 microns, about 8 microns, about 7 microns, about 6 microns, about 5 microns, about 4 microns, about 3 microns, about 2 microns or about 1 micron. In particular embodiments, the center-to-center spacing is about 5.1 microns or about 2.8 microns.

In some embodiments, the bead is in a reaction chamber, and optionally the only bead in the reaction chamber. In some embodiments, the reaction chamber is in contact with or capacitively coupled to an ISFET. In some embodiments, the ISFET is in an ISFET array In some embodiments, the bead has a diameter of less than 6 microns, less than 3 microns, or about 1 micron. The bead may have a diameter of about 1 micron up to about 7 microns, or about 1 micron up to about 3 microns.

In some embodiments, the reaction chambers have a center-to-center distance of about 1 micron to about 10 microns. In some embodiments, the reaction chamber array comprises $10^2$, $10^3$, $10^4$, $10^5$, $10^6$ or $10^7$ reaction chambers.

In accordance with the invention, a dielectric layer on a gate of an ISFET is part of the ISFET. It is recognized that the charge in the reaction chamber builds up on one side of the dielectric and forms one plate of a capacitor and which has as its second plate the floating gate metal layer; thus, a reaction chamber is referred to as being capacitively coupled to the ISFET.

In some embodiments, the ISFET is in an ISFET array. The ISFET array may comprise $10^2$, $10^3$, $10^4$, $10^5$, $10^6$, $10^7$ ISFETS.

In some embodiments, the template nucleic acid is in a reaction chamber in contact with or capacitively coupled to the ISFET. In some embodiments, the reaction chamber is in a reaction chamber array. In some embodiments, the reaction chamber array comprises $10^2$, $10^3$, $10^4$, $10^5$, $10^6$ or $10^7$ reaction chambers.

The microwells may vary in size between arrays. The size of these microwells may be described in terms of a width (or diameter) to height ratio. In some embodiments, this ratio is I:1 to 2:1.5. The bead to well size (e.g., the bead diameter to well width, diameter, or height) is preferably in the range of 0.6-0.8.

The microwell size may be described in terms of cross section. The cross section may refer to a "slice" parallel to the depth (or height) of the well, or it may be a slice perpendicular to the depth (or height) of the well. The microwells may be square in cross-section, but they are not so limited. The dimensions at the bottom of a microwell (i.e., in a cross section that is perpendicular to the depth of the well) may be 1.5 μm by 1.5 μm, or it may be 1.5 μm by 2 μm. Suitable diameters include but are not limited to at or about 100 μm, 95 μm, 90 μm, 85 μm, 80 μm, 75 μm, 70 μm, 65 μm, 60 μm, 55 μm, 50 μm, 45 μm, 40 J.tm, 35 μm, 30 μm, 25 μm, 20 μm, 15 μm, 10 J.tm, 9 μm, 8 μm, 7 μm, 6 J.tm, 5 J.tm, 4 μm, 3 μm, 2 μm, 1 μm or less. In some particular embodiments, the diameters may be at or about 44 J.tm, 32 J.tm, 85 μm, 4 μm, or 1.5 μm. Suitable heights include but are not limited to at or about 100 μm, 95 μm, 90 μm, 85 μm, 80 μm, 75 J.tm, 70 μm, 65 μm, 60 μm, 55 μm, 50 μm, 45 μm, 40 μm, 35 μm, 30 μm, 25 μm, 20 μm, 15 μm, 10 μm, 9 μm, 8 μm, 7 μm, 6 μm, 5 μm, 4 μm, 3 μm, 2 μm, 1 μm or less. In some particular embodiments, the heights may be at or about 55 μm, 48 μm, 32 μm, 12 μm, 8 μm, 6 μm, 4 μm, 2.25 μm, 1.5 μm, or less. Various embodiments of the invention contemplate the combination of any of these diameters with any of these heights. In still other embodiments, the reaction well dimensions may be (diameter in μm by height in μm) 44 by 55, 32 by 32, 32 by 48, 8 by 8, 8 by 12, 4 by 4, 4 by 6, 1.5 by 1.5, or 1.5 by 2.25.

The reaction well volume may range (between arrays, and preferably not within a single array) based on the well dimensions. This volume may be at or about 100 picoliter (pL), 90, 80, 70, 60, 50, 40, 30, 20, 10, or fewer pL. In important embodiments, the well volume is less than 1 pL, including equal to or less than 0.5 pL, equal to or less than 0.1 pL, equal to or less than 0.05 pL, equal to or less than 0.01 pL, equal to or less than 0.005 pL, or equal to or less than 0.001 pL. The volume may be 0.001 to 0.9 pL, 0.001 to 0.5 pL, 0.001 to 0.1 pL, 0.001 to 0.05 pL, or 0.005 to 0.05 pL. In particular embodiments, the well volume is 75 pL, 34 pL, 23 pL, 0.54 pL, 0.36 pL, 0.07 pL, 0.045 pL, 0.0024 pL, or 0.004 pL. In some embodiments, each reaction chamber is no greater than about 0.39 pL in volume and about 49 $\mu m^2$ surface aperture, and more preferably has an aperture no greater than about 16 $\mu m^2$ and volume no greater than about 0.064 pL.

Thus, it is to be understood that various aspects and embodiments of the invention relate generally to large scale FET arrays for measuring one or more analytes or for measuring charge bound to the chemFET surface. It will be appreciated that chemFETs and more particularly ISFETs may be used to detect analytes and/or charge. An ISFET, as discussed above, is a particular type of chemFET that is configured for ion detection such as hydrogen ion (or proton) detection. Other types of chemFETs contemplated by the present disclosure include enzyme FETs (EnFETs) which employ enzymes to detect analytes. It should be appreciated, however, that the present disclosure is not limited to ISFETs and EnFETs, but more generally relates to any FET that is configured for some type of chemical sensitivity. As used herein, chemical sensitivity broadly encompasses sensitivity to any molecule of interest, including without limitation organic, inorganic, naturally occurring, non-naturally occurring, chemical and biological compounds, such as ions, small molecules, polymers such as nucleic acids, proteins, peptides, polysaccharides, and the like.

In some embodiments, the invention encompasses a sequencing apparatus comprising a dielectric layer overlying a chemFET, the dielectric layer having a recess laterally centered atop the chemFET. Preferably, the dielectric layer is formed of silicon dioxide.

After the semiconductor structures, as shown, are formed, the microwell structure is applied to the die. That is, the microwell structure can be formed right on the die or it may be formed separately and then mounted onto the die, either approach being acceptable. To form the microwell structure on the die, various processes may be used. For example, the entire die may be spin-coated with, for example, a negative photoresist such as Microchem's SU-8 2015 or a positive resist/polyimide such as HD Microsystems HD8820, to the desired height of the microwells. The desired height of the wells (e.g., about 4-12 μm in the example of one pixel per well, though not so limited as a general matter) in the photoresist layer(s) can be achieved by spinning the appropriate resist at predetermined rates (which can be found by reference to the literature and manufacturer specifications, or empirically), in one or more layers. (Well height typically may be selected in correspondence with the lateral dimension of the sensor pixel, preferably for a nominal 1:1-1.5:1 aspect ratio, height:width or diameter. Based on signal-to-noise considerations, there is a relationship between dimensions and the required data sampling rates to achieve a desired level of performance. Thus there are a number of factors that will go into selecting optimum parameters for a given application.) Alternatively, multiple layers of different photoresists may be applied or another form of dielectric material may be deposited. Various types of chemical vapor deposition may also be used to build up a layer of materials suitable for microwell formation therein.

Once the photoresist layer (the singular form "layer" is used to encompass multiple layers in the aggregate, as well) is in place, the individual wells (typically mapped to have either one or four ISFET sensors per well) may be generated by placing a mask (e.g., of chromium) over the resist-coated die and exposing the resist to cross-linking (typically UV) radiation. All resist exposed to the radiation (i.e., where the mask does not block the radiation) becomes cross-linked and as a result will form a permanent plastic layer bonded to the surface of the chip (die). Unreacted resist (i.e., resist in areas which are not exposed, due to the mask blocking the light from reaching the resist and preventing cross-linking) is removed by washing the chip in a suitable solvent (i.e., developer) such as propyleneglycolmethylethylacetate (PGMEA) or other appropriate solvent. The resultant structure defines the walls of the microwell array.

For example, contact lithography of various resolutions and with various etchants and developers may be employed. Both organic and inorganic materials may be used for the layer(s) in which the microwells are formed. The layer(s) may be etched on a chip having a dielectric layer over the pixel structures in the sensor array, such as a passivation layer, or the layer(s) may be formed separately and then applied over the sensor array. The specific choice or processes will depend on factors such as array size, well size, the fabrication facility that is available, acceptable costs, and the like.

Among the various organic materials which may be used in some embodiments to form the microwelllayer(s) are the above-mentioned SU-8 type of negative-acting photoresist, a conventional positive-acting photoresist and a positive-acting photodefineable polyimide. Each has its virtues and its drawbacks, well known to those familiar with the photolithographic art.

Naturally, in a production environment, modifications will be appropriate.

Contact lithography has its limitations and it may not be the production method of choice to produce the highest densities of wells—i.e., it may impose a higher than desired minimum pitch limit in the lateral directions. Other techniques, such as a deep UV step-and-repeat process, are capable of providing higher resolution lithography and can be used to produce small pitches and possibly smaller well diameters. Of course, for different desired specifications (e.g., numbers of sensors and wells per chip), different techniques may prove optimal. And pragmatic factors, such as the fabrication processes available to a manufacturer, may motivate the use of a specific fabrication method. While novel methods are discussed, various aspects of the invention are limited to use of these novel methods.

Preferably the CMOS wafer with the ISFET array will be planarized after the final metallization process. A chemical mechanical dielectric planarization prior to the silicon nitride passivation is suitable. This will allow subsequent lithographic steps to be done on very flat surfaces which are free of back-end CMOS topography.

By utilizing deep-UV step-and-repeat lithography systems, it is possible to resolve small features with superior resolution, registration, and repeatability. However, the high resolution and large numerical aperture (NA) of these systems precludes their having a large depth of focus. As such, it may be necessary, when using such a fabrication system, to use thinner photodefinable spin-on layers (i.e., resists on the order of 1-2 μm rather than the thicker layers used in contact lithography) to pattern transfer and then etch microwell features to underlying layer or layers. High resolution lithography can then be used to pattern the microwell features and conventional $SiO_2$ etch chemistries can be used—one each for the bondpad areas and then the microwell areas having selective etch stops; the etch stops then can be on aluminum bondpads and silicon nitride passivation (or the like), respectively. Alternatively, other suitable substitute pattern transfer and etch processes can be employed to render microwells of inorganic materials.

Another approach is to form the microwell structure in an organic material. For example, a dual-resist "soft-mask" process may be employed, whereby a thin high-resolution deep UV resist is used on top of a thicker organic material (e.g., cured polyimide or opposite-acting resist). The top resist layer is patterned. The pattern can be transferred using an oxygen plasma reactive ion etch process. This process sequence is sometimes referred to as the "portable conformable mask" (PCM) technique. See B. J. Lin et al., "Practicing the Novolac deep-UV portable conformable masking technique", Journal of Vacuum Science and Technology 19, No. 4, 1313-1319 (1981); and A. Cooper et al., "Optimization of a photosensitive spin-on dielectric process for copper inductor coil and interconnect protection in RF SoC devices.

Alternatively a "drill-focusing" technique may be employed, whereby several sequential step-and-repeat exposures are done at different focal depths to compensate for the limited depth of focus (DOE) of high-resolution steppers when patterning thick resist layers. This technique depends on the stepper NA and DOF as well as the contrast properties of the resist material.

Thus, microwells can be fabricated by any high aspect ratio photo-definable or etchable thin-film process, that can provide requisite thickness (e.g., about 4-10 μm). Among the materials believed to be suitable are photosensitive polymers, deposited silicon dioxide, nonphotosensitive polymer which can be etched using, for example, plasma etching processes, etc. In the silicon dioxide family, TEOS and silane nitrous oxide (SILOX) appear suitable. The final structures are similar but the various materials present differing surface compositions that may cause the target biology or chemistry to react differently.

When the microwell layer is formed, it may be necessary to provide an etch stop layer so that the etching process does not proceed further than desired. For example, there may be an underlying layer to be preserved, such as a low-K dielectric. The etch stop material should be selected according to the application. SiC and SiN materials may be suitable, but that is not meant to indicate that other materials may not be employed, instead. These etch-stop materials can also serve to enhance the surface chemistry which drives the ISFET sensor sensitivity, by choosing the etch-stop material to have an appropriate point of zero charge (PZC). Various metal oxides may be suitable addition to silicon dioxide and silicon nitride.

The PZCs for various metal oxides may be found in various texts, such as "Metal Oxides-Chemistry and Applications" by J. Fierro. We have learned that Ta20s may be preferred as an etch stop over $Al_2O_3$ because the PZC of $Al_2O_3$ is right at the pH being used (i.e., about 8.8) and, hence, right at the point of zero charge. In addition $Ta_2O_5$ has a higher sensitivity to pH (i.e., m V/pH), another important factor in the sensor performance. Optimizing these parameters may require judicious selection of passivation surface materials.

Using thin metal oxide materials for this purpose (i.e., as an etch stop layer) is difficult due to the fact of their being so thinly deposited (typically 200-SOOA). A post-microwell fabrication metal oxide deposition technique may allow placement of appropriate PZC metal oxide films at the bottom of the high aspect ratio microwells.

Electron-beam depositions of (a) reactively sputtered tantalum oxide, (b) nonreactive stoichiometric tantalum oxide, (c) tungsten oxide, or (d) Vanadium oxide may prove to have superior "down-in-well" coverage due to the superior directionality of the deposition process.

The array typically comprises at least 100 microfluidic wells, each of which is coupled to one or more chemFET sensors. Preferably, the wells are formed in at least one of a glass (e.g., $SiO_2$), a polymeric material, a photodefinable material or a reactively ion etchable thin film material. Preferably, the wells have a width to height ratio less than about 1:1. Preferably the sensor is a field effect transistor, and more preferably a chemFET. The chemFET may optionally be coupled to a PPi receptor. Preferably, each of the chemFETs occupies an area of the array that is $10^2$ microns or less.

In some embodiments, the invention encompasses a sequencing device comprising a semiconductor wafer device coupled to a dielectric layer such as a glass (e.g., $SiO_2$), polymeric, photodefinable or reactive ion etchable material in which reaction chambers are formed. Typically, the glass, dielectric, polymeric, photodefinable or reactive ion etchable material is integrated with the semiconductor wafer layer. In some instances, the glass, polymeric, photodefinable or reactive ion etchable layer is non-crystalline. In some instances, the glass may be $SiO_2$. The device can optionally further comprise a fluid delivery module of a suitable material such as a polymeric material, preferably an injection moldable material. More preferably, the polymeric layer is polycarbonate.

In some embodiments, the invention encompasses a method for manufacturing a sequencing device comprising: using photolithography, generating wells in a glass, dielectric, photodefinable or reactively ion etchable material on top of an array of transistors.

Yet another alternative when a CMOS or similar fabrication process is used for array fabrication is to form the microwells directly using the CMOS materials. That is, the CMOS top metallization layer forming the floating gates of the ISFET array usually is coated with a passivation layer that is about 1.3 μm thick. Microwells 1.3 μm deep can be formed by etching away the passivation material. For example, microwells having a 1:1 aspect ratio may be formed, 1.3 μm deep and 1.3 μm across at their tops. Modeling indicates that as the well size is reduced, in fact, the DNA concentration, and hence the SNR, increases. So, other factors being equal, such small wells may prove desirable.

Flow Cells and Fluidics System

A complete system for using the sensor array will include suitable fluid sources, valving and a controller for operating the valving to low reagents and washes over the microarray or sensor array, depending on the application. These elements are readily assembled from off-the-shelf components, with and the controller may readily be programmed to perform a desired experiment.

It should be understood that the readout at the chemFET may be current or voltage (and change thereof) and that any particular reference to either readout is intended for simplicity and not to the exclusion of the other readout. Therefore any reference in the following text to either current or voltage detection at the chemFET should be understood to contemplate and apply equally to the other readout as well. In important embodiments, the readout reflects a rapid, transient change in concentration of an analyte. The concentration of more than one analyte may be detected at different times. In some instances, such measurements are to be contrasted with methods that focus on steady state concentration measurements.

The process of using the assembly of an array of sensors on a chip combined with an array of microwells to sequence the DNA in a sample is referred to as an "experiment." Executing an experiment requires loading the wells with the DNA-bound beads and the flowing of several different fluid solutions (i.e., reagents and washes) across the wells. A fluid delivery system (e.g., valves, conduits, pressure source(s), etc.) coupled with a fluidic interface is needed which flows the various solutions across the wells in a controlled even flow with acceptably small dead volumes and small cross contamination between sequential solutions. Ideally, the fluidic interface to the chip (sometimes referred to as a "flow cell") would cause the fluid to reach all microwells at the same time. To maximize array speed, it is necessary that the array outputs be available at as close to the same time as possible. The ideal clearly is not possible, but it is desirable to minimize the differentials, or skews, of the arrival times of an introduced fluid, at the various wells, in order to maximize the overall speed of acquisition of all the signals from the array.

Flow cell designs of many configurations are possible; thus the system and methods presented herein are not dependent on use of a specific flow cell configuration. It is desirable, though, that a suitable flow cell substantially conform to the following set of objectives:

- have connections suitable for interconnecting with a fluidics delivery system—e.g., via appropriately-sized tubing;
- have appropriate head space above wells;
- minimize dead volumes encountered by fluids;
- minimize small spaces in contact with liquid but not quickly swept clean by flow of a wash fluid through the flow cell (to minimize cross contamination);
- be configured to achieve uniform transit time of the flow over the array;
- generate or propagate minimal bubbles in the flow over the wells;
- be adaptable to placement of a removable reference electrode inside or as close to the flow chamber as possible;
- facilitate easy loading of beads;
- be manufacturable at acceptable cost; and
- be easily assembled and attached to the chip package.

Satisfaction of these criteria so far as possible will contribute to system performance positively. For example, minimization of bubbles is important so that signals from the array truly indicate the reaction in a well rather than being spurious noise.

Each of several example designs will be discussed, meeting these criteria in differing ways and degrees. In each instance, one typically may choose to implement the design in one of two ways: either by attaching the flow cell to a frame and gluing the frame (or otherwise attaching it) to the chip or by integrating the frame into the flow cell structure and attaching this unified assembly to the chip. Further, designs may be categorized by the way the reference electrode is integrated into the arrangement. Depending on the design, the reference electrode may be integrated into the flow cell (e.g., form part of the ceiling of the flow chamber) or be in the flow path (typically to the outlet or downstream side of the flow path, after the sensor array).

Figure 9:
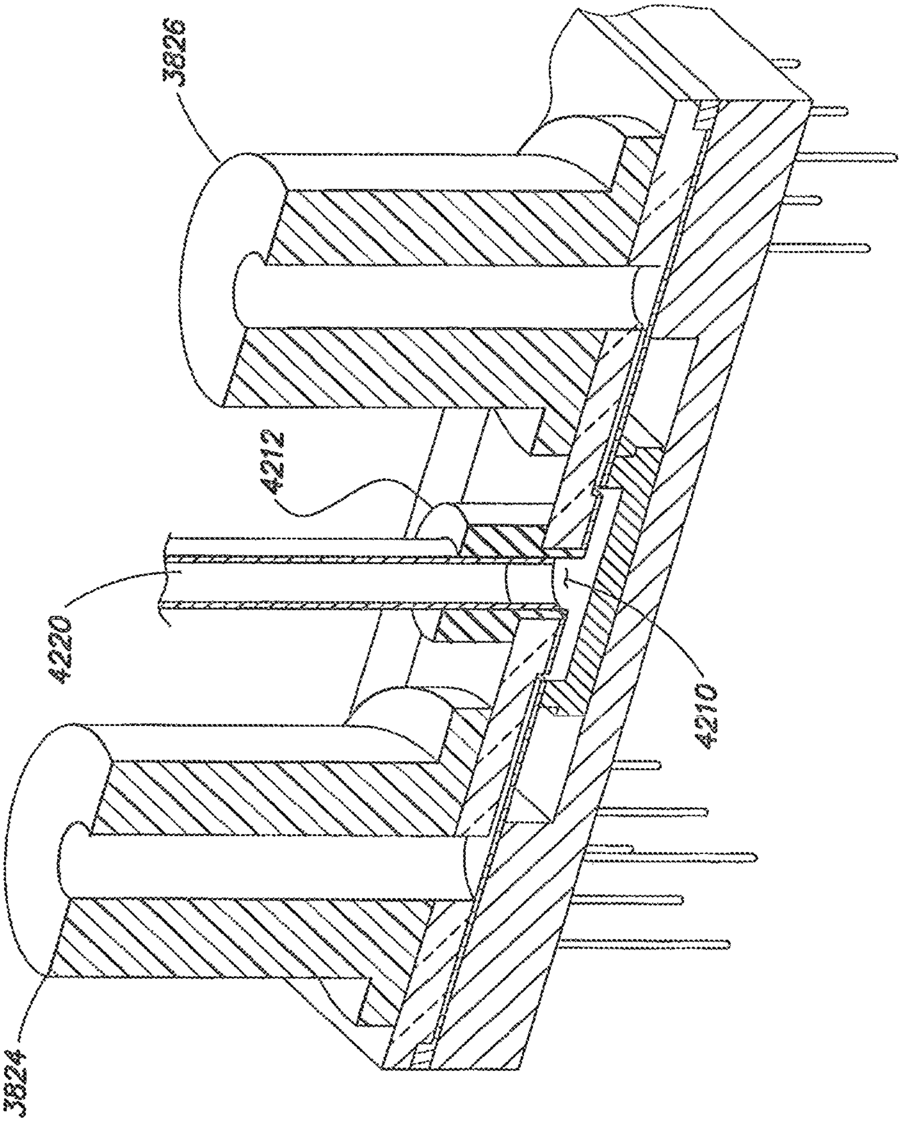
FIG. 9 is a cross-sectional view of a flow cell.

An example of a suitable experiment apparatus 3410 incorporating such a fluidic interface is shown in FIG. 9, the manufacture and construction of which will be discussed in greater detail below. The apparatus comprises a semiconductor chip 3412 (indicated generally, though hidden) on or in which the arrays of wells and sensors are formed, and a fluidics assembly 3414 on top of the chip and delivering the sample to the chip for reading. The fluidics assembly includes a portion 3416 for introducing fluid containing the sample, a portion 3418 for allowing the fluid to be piped out, and a flow chamber portion 3420 for allowing the fluid to flow from inlet to outlet and along the way interact with the material in the wells. Those three portions are unified by an interface comprising a glass slide 3422 (e.g., Erie Microarray Cat #C22-5128-M20 from Erie Scientific Company, Portsmouth, N.H., cut in thirds, each to be of size about 25 mm×25 mm).

Mounted on the top face of the glass slide are two fittings, 3424 and 3426, such as nanoport fittings Part #N-333 from Upchurch Scientific of Oak Harbor, Wash. One port (e.g., 3424) serves as an inlet delivering liquids from the pumpinglvalving system described below but not shown here. The second port (e.g., 3426) is the outlet which pipes the liquids to waste. Each port connects to a conduit 3428, 3432 such as flexible tubing of appropriate inner diameter. The nanoports are mounted such that the tubing can penetrate corresponding holes in the glass slide. The tube apertures should be flush with the bottom surface of the slide.

On the bottom of the glass slide, flow chamber 3420 may comprise various structures for promoting a substantially laminar flow across the microwell array. For example, a series of microfluidic channels fanning out from the inlet pipe to the edge of the flow chamber may be patterned by contact lithography using positive photoresists such as SU-8 photoresist from MicroChem Corp. of Newton, Mass. Other structures will be discussed below.

The chip 3412 will in turn be mounted to a carrier 3430, for packaging and connection to connector pins 3432.

Achieving a uniform flow front and eliminating problematic flow path areas is desirable for a number of reasons. One reason is that very fast transition of fluid interfaces within the system's flow cell is desired for many applications, particularly gene sequencing. In other words, an incoming fluid must completely displace the previous fluid in a short period of time. Uneven fluid velocities and diffusion within the flow cell, as well as problematic flow paths, can compete with this requirement. Simple flow through a conduit of rectangular cross section can exhibit considerable disparity of fluid velocity from regions near the center of the flow volume to those adjacent the sidewalls, one sidewall being the top surface of the microwell layer and the fluid in the wells. Such disparity leads to spatially and temporally large concentration gradients between the two traveling fluids. Further, bubbles are likely to be trapped or created in stagnant areas like sharp corners interior the flow cell. (The surface energy (hydrophilic vs. hydrophobic) can significantly affect bubble retention. Avoidance of surface contamination during processing and use of a surface treatment to create a more hydrophilic surface should be considered if the as-molded surface is too hydrophobic.) Of course, the physical arrangement of the flow chamber is probably the factor which most influences the degree of uniformity achievable for the flow front.

In all cases, attention should be given to assuring a thorough washing of the entire flow chamber, along with the microwells, between reagent cycles. Flow disturbances may exacerbate the challenge of fully cleaning out the flow chamber.

Flow disturbances may also induce or multiply bubbles in the fluid. A bubble may prevent the fluid from reaching a microwell, or delay its introduction to the microwell, introducing error into the microwell reading or making the output from that microwell useless in the processing of outputs from the array. Thus, care should be taken in selecting configurations and dimensions for the flow disruptor elements to manage these potential adverse factors. For example, a tradeoff may be made between the heights of the disruptor elements and the velocity profile change that is desired.

The flow cell, as stated elsewhere, may be fabricated of many different materials. Injection molded polycarbonate appears to be quite suitable. A conductive metal (e.g., gold) may be deposited using an adhesion layer (e.g., chrome) to the underside of the flow cell roof (the ceiling of the flow chamber). Appropriate low-temperature thin-film deposition techniques preferably are employed in the deposition of the metal reference electrode due to the materials (e.g., polycarbonate) and large step coverage topography at the bottom-side of the fluidic cell (i.e., the frame surround of ISFET array). One possible approach would be to use electron-beam evaporation in a planetary system.

Once assembly is complete—conductive epoxy (e.g., Epo-Tek H20E or similar) may be dispensed on the seal ring with the flow cell aligned, placed, pressed and cured—the ISFET flow cell is ready for operation with the reference potential being applied to the assigned pin of the package.

In some embodiments, the invention encompasses an apparatus for detection of pH comprising a laminar fluid flow system. Preferably, the apparatus is used for sequencing a plurality of nucleic acid templates present in an array.

The apparatus typically includes a fluidics assembly comprising a member comprising one or more apertures for non-mechanically directing a fluid to flow to an array of at least 100 K (100 thousand), 500 K (500 thousand), or 1 M (1 million) microfluidic reaction chambers such that the fluid reaches all of the microfluidic reaction chambers at the same time or substantially the same time. Typically, the fluid flow is parallel to the sensor surface. Typically, the assembly has a Reynolds number of less than 1000, 500, 200, 100, 50, 20, or 10. Preferably, the member further comprises a first aperture for directing fluid towards the sensor array and a second aperture for directing fluid away from the sensor array.

In some embodiments, the invention encompasses a method for directing a fluid to a sensor array comprising: providing a fluidics assembly comprising an aperture fluidly coupling a fluid source to the sensor array; and non-mechanically directing a fluid to the sensor array. By "non-mechanically" it is meant that the fluid is moved under pressure from a gaseous pressure source, as opposed to a mechanical pump.

In some embodiments, the invention encompasses an array of wells, each of which is coupled to a lid having an inlet port and an outlet port and a fluid delivery system for delivering and removing fluid from said inlet and outlet ports non-mechanically.

In some embodiments, the invention encompasses a method for sequencing a biological polymer such as a nucleic acid utilizing the above-described apparatus, comprising: directing a fluid comprising a monomer to an array of reaction chambers wherein the fluid has a fluid flow Reynolds number of at most 2000, 1000, 200, 100, 50, or 20. The method may optionally further comprise detecting a pH or a change in pH from each said reaction chamber. This is typically detected by ion diffusion to the sensor surface.

There are various other ways of providing a fluidics assembly for delivering an appropriate fluid flow across the microwell and sensor array assembly, and the forgoing examples are thus not intended to be exhaustive.

pH-Based Nucleic Acid Sequencing

Apparatus of the invention may be adapted to detecting hydrogen ions released by nucleotide incorporation, which detection process is disclosed as a DNA sequencing method in Rothberg et al., U.S. patent publications 2009/0026082 and 2009/0127589. It is important in these and various other aspects to detect as many released hydrogen ions as possible in order to achieve as high a signal (and/or a signal to noise ratio) as possible. Strategies for increasing the number of released protons that are ultimately detected by the chemFET surface include without limitation limiting interaction of released protons with reactive groups in the well, choosing a material from which to manufacture the well in the first instance that is relatively inert to protons, preventing released protons from exiting the well prior to detection at the chemFET, and increasing the copy number of templates per well (in order to amplify the signal from each nucleotide incorporation), among others.

In one aspect, the invention provides arrays and devices with reduced buffering capacity for monitoring and/or measuring hydrogen ion changes (or pH changes) more accurately. As an example, the invention provides apparatus and devices for monitoring pH changes in polymerase extension reactions in an environment with no or limited buffering capacity. Examples of a reduced buffering environment include environments that lack pH buffering components in the sample fluid and/or reaction mixtures; environments in which surfaces of array components in contact with sample fluid and/or reaction mixtures have little or no buffering capacity; and environments in which pH changes on the order of 0.01, 0.05, 0.1, 0.2, 0.3, 0.4, 0.5, 0.6. 0.7, 0.8, 0.9, or 1.0 pH units are detectable for example via a chemFET and more particularly an ISFET as described herein.

The buffering inhibitor may also be a phospholipid. The phospholipids may be naturally occurring or non-naturally occurring phospholipids. Examples of phospholipids to be used as buffering inhibitors include but are not limited to phosphatidylcholine, hosphatidylethanolamine, phosphatidylglycerol, and phosphatidylserine. In some embodiments, phospholipids may be coated on the chemFET surface (or reaction chamber surface). Such coating may be covalent or noncovalent. In other embodiments, the phospholipids exist in solution.

Some instances of the invention employ an environment, including a reaction solution, that is minimally buffered, if at all. Buffering can be contributed by the components of the solution or by the solid supports in contact with such solution. A solution having no or low buffering capacity (or activity) is one in which changes in hydrogen ion concentration on the order of at least about +/−0.005 pH units, at least about +/−0.01, at least about +/−0.015, at least about +/−0.02, at least about +/−0.03, at least about +/−0.04, at least about +/−0.05, at least about +/−0.10, at least about +/−0.15, at least about +/−0.20, at least about +/−0.25, at least about +/−0.30, at least about +/−0.35, at least about +/−0.45, at least about +/−0.50, or more are detectable (e.g., using the chemFET sensors described herein). In some embodiments, the pH change per nucleotide incorporation is on the order of about 0.005. In some embodiments, the pH change per nucleotide incorporation is a decrease in pH. Reaction solutions that have no or low buffering capacity may contain no or very low concentrations of buffer, or may use weak buffers.

Concatemerized Templates

Increasing the number of templates or primers (i.e., copy number) results in a greater number of nucleotide incorporations per sensor and/or per reaction chamber, thereby leading to a higher signal and thus signal to noise ratio. Copy number can be increased for example by using templates that are concatemers (i.e., nucleic acids comprising multiple, tandemly arranged, copies of the nucleic acid to be sequenced), by increasing the number of nucleic acids on or in beads up to and including saturating such beads, and by attaching templates or primers to beads or to the sensor surface in ways that reduce steric hindrance and/or ensure template attachment (e.g., by covalently attaching templates), among other things. Concatemer templates may be immobilized on or in beads or on other solid supports such as the sensor surface, although in some embodiments concatemers templates may be present in a reaction chamber without immobilization. For example, the templates (or complexes comprising templates and primers) may be covalently or non-covalently attached to the chemFET surface and their sequencing may involve detection of released hydrogen ions and/or addition of negative charge to the chemFET surface upon a nucleotide incorporation event. The latter detection scheme may be performed in a buffered environment or solution (i.e., any changes in pH will not be detected by the chemFET and thus such changes will not interfere with detection of negative charge addition to the chemFET surface).

RCA or CCR amplification methods generate concatemers of template nucleic acids that comprise tens, hundreds, thousands or more tandemly arranged copies of the template. Such concatemers may still be referred to herein as template nucleic acids, although they may contain multiple copies of starting template nucleic acids. In some embodiments, they may also be preferred to as amplified template nucleic acids. Alternatively, they may be referred to herein as comprising multiple copies of target nucleic acid fragment. Concatemers may contain 2, 3, 4, 5, 6, 7, 8, 9, 10, 20, 30, 40, 50, 60, 70, 80, 90, 100, 500, 1000, or more copies of the starting nucleic acid. They may contain $10$-$10^2$, $10^2$-$10^3$, $10^3$-$10^4$, $10^3$-$10^5$, or more copies of the starting nucleic acid. Concatemers generated using these or other methods (such as for example DNA nanoballs) can be used in the sequencing-by-synthesis methods described herein. The concatemers may be generated in vitro apart from the array and then placed into reaction chambers of the array or they may be generated in the reaction chambers. One or more inside walls of the reaction chamber may be treated to enhance attachment and retention of the concatemers, although this is not required. In some embodiments of the invention, if the concatemers are attached to an inside wall of the reaction chamber, such as the chemFET surface, then nucleotide incorporation at least in the context of a sequencing-by-synthesis reaction may be detected by a change in charge at the chemFET surface, as an alternative to or in addition to the detection of released hydrogen ions as discussed herein. If the concatemers are deposited onto a chemFET surface and/or into a reaction chamber, sequencing-by-synthesis can occur through detection of released hydrogen ions as discussed herein. The invention embraces the use of other approaches for generating concatemerized templates. One such approach is a PCR described by Stemmer et al. in U.S. Pat. No. 5,834,252, and the description of this approach is incorporated by reference herein.

Important aspects of the invention contemplate sequencing a plurality of different template nucleic acids simultaneously. This may be accomplished using the sensor arrays described herein. In one embodiment, the sensor arrays are overlayed (and/or integral with) an array of microwells (or reaction chambers or wells, as those terms are used interchangeably herein), with the proviso that there be at least one sensor per microwell. Present in a plurality of microwells is a population of identical copies of a template nucleic acid. There is no requirement that any two microwells carry identical template nucleic acids, although in some instances such templates may share overlapping sequence. Thus, each microwell comprises a plurality of identical copies of a template nucleic acid, and the templates between microwells may be different.

It is to be understood therefore that the invention contemplates a sequencing apparatus for sequencing unlabeled nucleic acid acids, optionally using unlabeled nucleotides, without optical detection and comprising an array of at least 100 reaction chambers. In some embodiments, the array comprises $10^3$, $10^4$, $10^5$, $10^6$, $10^7$ or more reaction chambers. The pitch (or center-to-center distance between adjacent reaction chambers) is on the order of about 1-10 microns, including 1-9 microns, 1-8 microns, 1-7 microns, 1-6 microns, 1-5 microns, 1-4 microns, 1-3 microns, or 1-2 microns.

In various aspects and embodiments of the invention, the nucleic acid loaded beads, of which there may be tens, hundreds, thousands, or more, first enter the flow cell and then individual beads enter individual wells. The beads may enter the wells passively or otherwise. For example, the beads may enter the wells through gravity without any applied external force. The beads may enter the wells through an applied external force including but not limited to a magnetic force or a centrifugal force. In some embodiments, if an external force is applied, it is applied in a direction that is parallel to the well height/depth rather than transverse to the well height/depth, with the aim being to "capture" as many beads as possible. Preferably, the wells (or well arrays) are not agitated, as for example may occur through an applied external force that is perpendicular to the well height/depth. Moreover, once the wells are so loaded, they are not subjected to any other force that could dislodge the beads from the wells.

The Examples provide a brief description of an exemplary bead loading protocol in the context of magnetic beads. It is to be understood that a similar approach could be used to load other bead types. The protocol has been demonstrated to reduce the likelihood and incidence of trapped air in the wells of the flow chamber, uniformly distribute nucleic acid loaded beads in the totality of wells of the flow chamber, and avoid the presence and/or accumulation of excess beads in the flow chamber.

In various instances, the invention contemplates that each well in the flow chamber contain only one nucleic acid loaded bead. This is because the presence of two beads per well will yield unusable sequencing information derived from two different template nucleic acids.

As part of the sequencing reaction, a dNTP will be ligated to (or "incorporated into" as used herein) the 3' of the newly synthesized strand (or the 3' end of the sequencing primer in the case of the first incorporated dNTP) if its complementary nucleotide is present at that same location on the template nucleic acid. Incorporation of the introduced dNTP (and concomitant release of PPi) therefore indicates the identity of the corresponding nucleotide in the template nucleic acid. If no dNTP has been incorporated, no hydrogens are released and no signal is detected at the ChemFET surface. One can therefore conclude that the complementary nucleotide was not present in the template at that location. If the introduced dNTP has been incorporated into the newly synthesized strand, then the chemFET will detect a signal. The signal intensity and/or area under the curve is a function of the number of nucleotides incorporated (for example, as may occur in a homopolymer stretch in the template. The result is that no sequence information is lost through the sequencing of a homopolymer stretch (e.g., poly A, poly T, poly C, or poly G) in the template.

Example 1

On-Chip Polymerase Extension Detected by pH Shift on an ISFET Array.

Figure 10A:
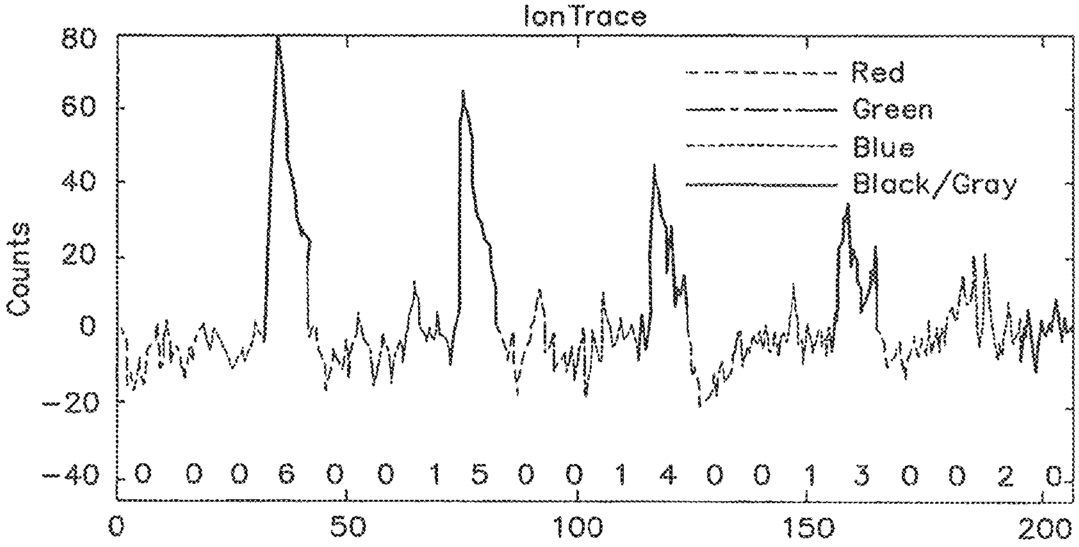
FIGS. 10A and B are graphs showing a trace from an ISFET device (A) and a nucleotide readout (B) from a sequencing reaction of a 23-mer synthetic oligonucleotide.
Figure 10B:
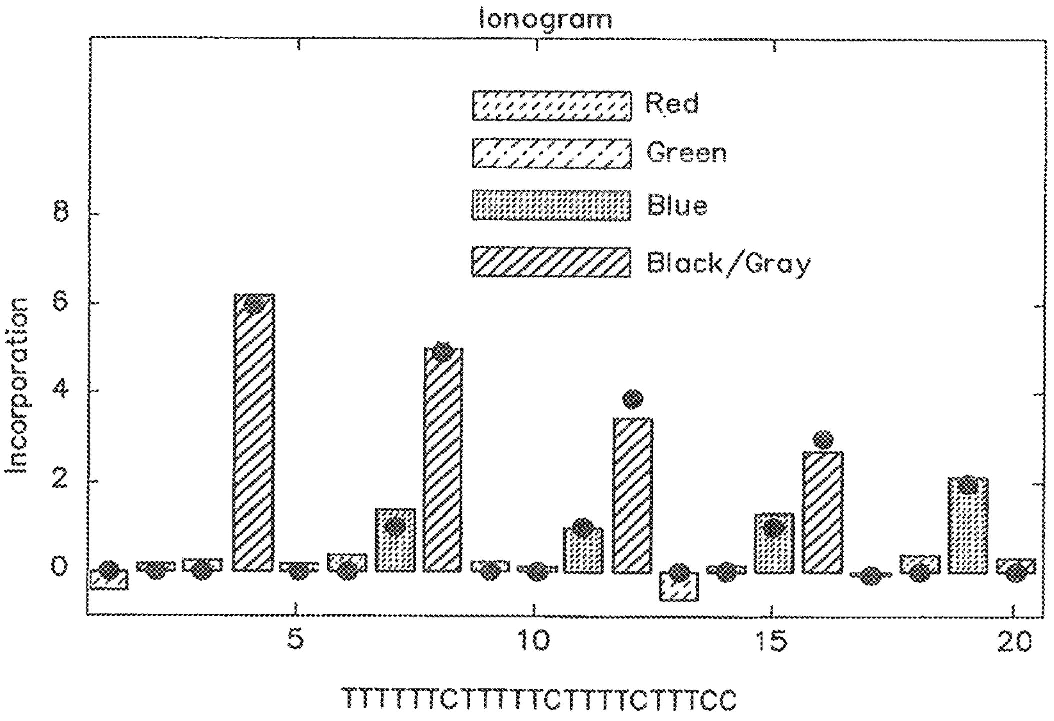

Streptavidin-coated 2.8 micron beads carrying biotinylated synthetic template to which sequencing primers and T4 DNA polymerase are bound were subjected to three sequential flows of each of the four nucleotides. Each nucleotide cycle consisted of flows of dATP, dCTP, dGTP and dTTP, each interspersed with a wash flow of buffer only. Flows from the first cycle are shown in blue, flows from the second cycle in red, and the third cycle in yellow. As shown in FIG. 10A, signal generated for both of the two dATP flows were very similar. FIG. 10B shows that the first (blue) trace of dCTP is higher than the dCTP flows from subsequent cycles, corresponding to the flow in which the polymerase should incorporate a single nucleotide per template molecule. FIG. 10C shows that the first (blue) trace of dGTP is approximately 6 counts higher (peak-to-peak) than the dGTP flows from subsequent cycles, corresponding to the flow in which the polymerase should incorporate a string of 10 nucleotides per template molecule. FIG. 10D shows that the first (blue) trace of dTTP is also approximately 6 counts higher (peak-to-peak) than the dTTP flows from subsequent cycles, corresponding to the flow in which the polymerase should incorporate 10 nucleotides per template molecule.

Example 2

Sequencing in a Closed System and Data Manipulation

Sequence has been obtained from a 23-mer synthetic oligonucleotide and a 25-mer PCR product oligonucleotide. The oligonucleotides were attached to beads which were then loaded into individual wells on a chip having 1.55 million sensors in a 1348×1152 array having a 5.1 micron pitch (38400 sensors per $mm^2$). About 1 million copies of the synthetic oligonucleotide were loaded per bead, and about 300000 to 600000 copies of the PCR product were loaded per bead. A cycle of 4 nucleotides through and over the array was 2 minutes long. Nucleotides were used at a concentration of 50 micromolar each. Polymerase was the only enzyme used in the process. Data were collected at 32 frames per second.

Figure 11A:
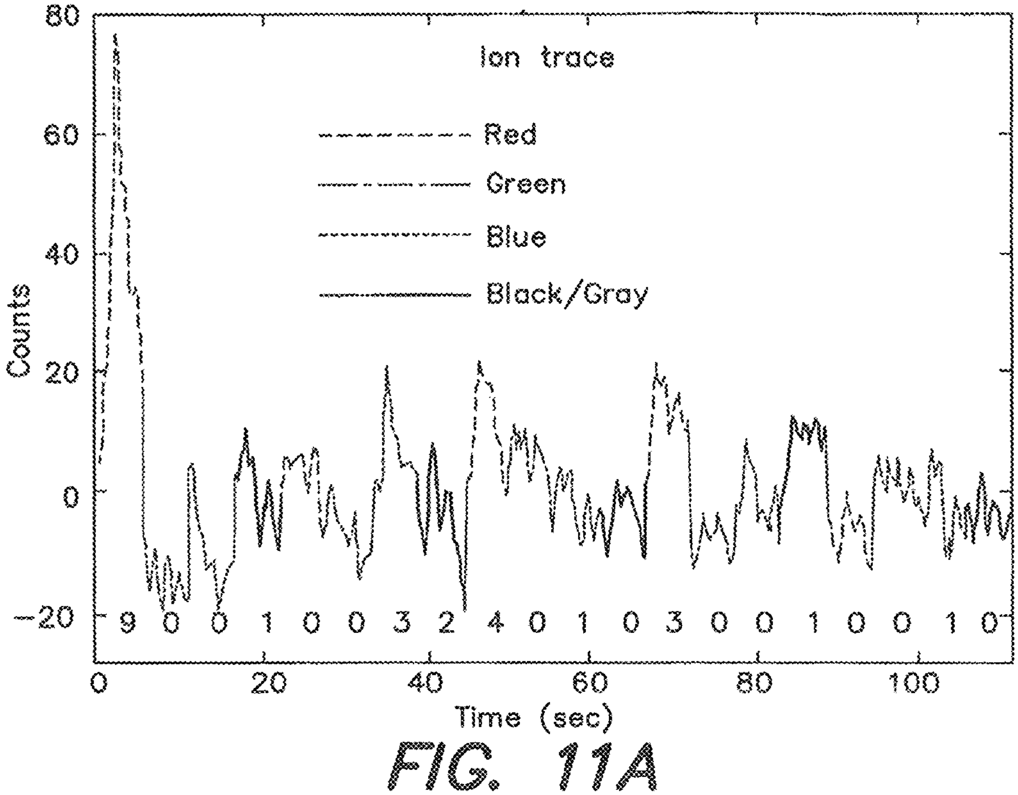
FIGS. 11A and B are graphs showing a trace from an ISFET device (A) and a nucleotide readout (B) from a sequencing reaction of a 25-mer PCR product.

FIG. 11A depicts the raw data measured directly from an ISFET for the synthetic oligonucleotide. One millivolt is equivalent to 68 counts. The data are sampled at each sensor on the chip (1550200 sensors on a 314 chip) many times per second. The Figure is color-coded for each nucleotide flow. With each nucleotide flow, several seconds of imaging occur. The graph depicts the concatenation of those individual measurements taken during each flow. The Y axis is in raw counts, and the X axis is in seconds. Superimposed just above the X axis are the expected incorporations at each flow.

Figure 11B:
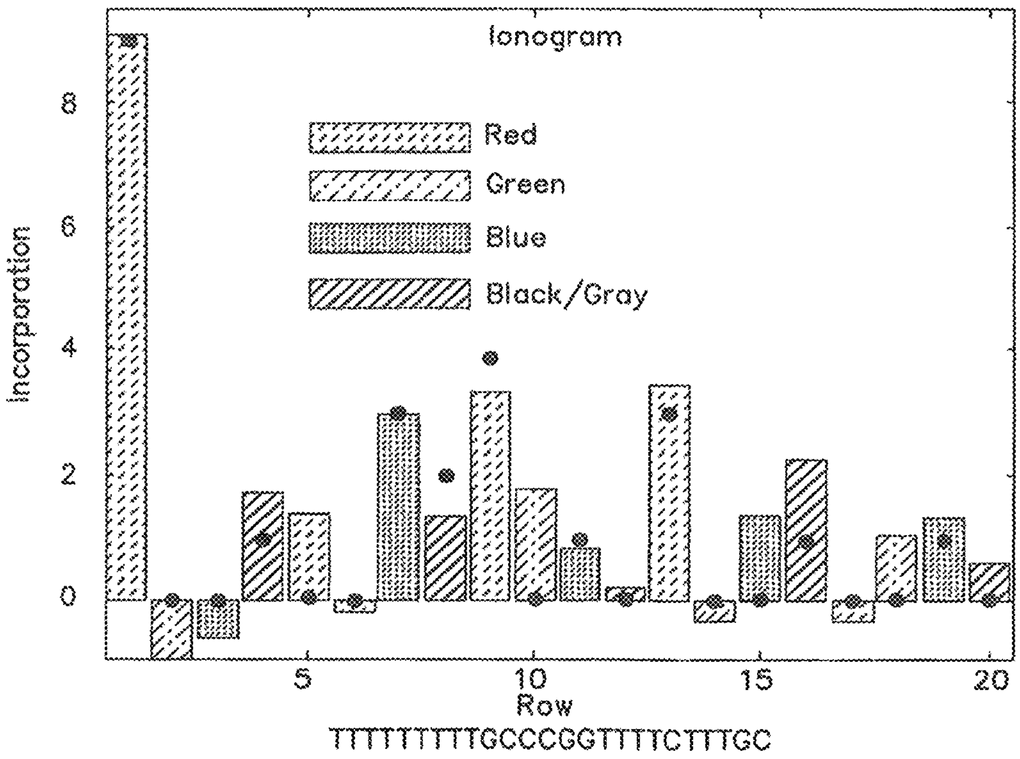

FIG. 11 B depicts the integrated value for each nucleotide flow, normalized to the template being sequenced. The integrated value is taken from the raw trace measurements shown in FIG. 11 A, and the integral bounds have been chosen to maximize signal to noise ratio. The results have been normalized to the signal per base incorporation, and graphed per nucleotide flow. The Y axis is incorporation count, and the X axis is nucleotide flow number, alternating through TACG.

What is claimed is:

1. A method for analyzing a sample on a sensor array, comprising:

generating a sensor signal from a chemically-sensitive field effect transistor (chemFET) sensor in response to a reaction occurring in a reaction well capacitively coupled to the chemFET sensor;

coupling a reference signal from a reference circuit directly to a column buffer input of a column buffer connected to a circuit node via a reference circuit switch coupled to the circuit node in response to a timing signal during a first time interval to provide a reference sample via the column buffer to a sampling circuit;

coupling the sensor signal to the column buffer via a row select switch between the chemFET sensor and the circuit node; the row select switch coupling a terminal of the chemFET sensor to the column buffer during a second time interval; and producing an output signal of the chemFET sensor in the sampling circuit as a function of the reference sample obtained during the first interval and a sensed sample of the sensor signal obtained during the second interval, wherein the output signal of the chemFET sensor indicates a characteristic of the reaction.

2. The method of claim 1, wherein the characteristic of the reaction is related to a concentration of a charged species in a sample fluid.

3. The method of claim 1, wherein the reaction occurring within the reaction well is a nucleic acid sequencing reaction.

4. The method of claim 3, wherein the characteristic of the reaction is related to a concentration of hydrogen ions.

5. The method of claim 1, wherein the reference signal is a reference voltage.

6. The method of claim 1, wherein producing an output signal further comprises:

storing the output signal of the chemFET sensor in a difference circuit of the sampling circuit; and coupling the difference circuit to a column output circuit node.

7. The method of claim 1, wherein producing an output signal comprises producing a noise-reduced output signal of the chemFET sensor.

* * * * *